(12) United States Patent
Auriault et al.

(10) Patent No.: US 9,986,721 B2
(45) Date of Patent: *Jun. 5, 2018

(54) TRANSGENIC MICE HAVING A HUMAN MAJOR HISTOCOMPATIBILITY COMPLEX (MHC) PHENOTYPE, EXPERIMENTAL USES AND APPLICATIONS

(75) Inventors: Claude Auriault, Juan les Pins (FR); Véronique Pancre, Orchies (FR); Yu-Chun Lone, Paris (FR); Anthony Pajot, Paris (FR); François Lemonnier, Bourg la Reine (FR)

(73) Assignees: INSTITUT PASTEUR, Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 190 days.
This patent is subject to a terminal disclaimer.

(21) Appl. No.: 13/551,137

(22) Filed: Jul. 17, 2012

(65) Prior Publication Data
US 2017/0079253 A1 Mar. 23, 2017

Related U.S. Application Data

(63) Continuation of application No. 10/566,386, filed as application No. PCT/IB2004/002374 on Jul. 5, 2004, now abandoned.

(60) Provisional application No. 60/490,945, filed on Jul. 30, 2003.

(51) Int. Cl.
| | |
|---|---|
| *G01N 33/00* | (2006.01) |
| *A01K 67/00* | (2006.01) |
| *A01K 67/027* | (2006.01) |
| *A61K 49/00* | (2006.01) |
| *C07K 14/74* | (2006.01) |
| *C12N 15/85* | (2006.01) |
| *C12N 15/00* | (2006.01) |

(52) U.S. Cl.
CPC ...... *A01K 67/0278* (2013.01); *A01K 67/0275* (2013.01); *A01K 67/0276* (2013.01); *A61K 49/0008* (2013.01); *C07K 14/70539* (2013.01); *C12N 15/8509* (2013.01); *A01K 2207/15* (2013.01); *A01K 2217/00* (2013.01); *A01K 2217/05* (2013.01); *A01K 2217/052* (2013.01); *A01K 2217/054* (2013.01); *A01K 2217/075* (2013.01); *A01K 2227/105* (2013.01); *A01K 2267/03* (2013.01)

(58) Field of Classification Search
CPC ............ A01K 2207/15; A01K 2217/00; A01K 2217/05; A01K 2217/052; A01K 2217/054; A01K 2217/075; A01K 2227/105; A01K 2267/03; A01K 67/0275; A01K 67/0276; A01K 67/0278; A61K 49/0008; C07K 14/70539; C12N 15/8509
USPC ........................................................... 800/3
See application file for complete search history.

(56) References Cited

U.S. PATENT DOCUMENTS

| 2003/0101465 A1 | 5/2003 | Lawman et al. |
| 2005/0114910 A1 | 5/2005 | Lone et al. |

FOREIGN PATENT DOCUMENTS

| EP | 1 529 536 A1 | 5/2005 |
| WO | WO 2000/025725 | 5/2000 |
| WO | WO/02/059263 A2 * | 8/2002 |
| WO | WO 03/006639 A1 | 1/2003 |
| WO | WO 2003/006639 A1 | 1/2003 |
| WO | WO 02/059263 A2 | 8/2003 |
| WO | WO 2002/059263 A2 | 8/2003 |

OTHER PUBLICATIONS

Ben-Mohamed et al., 2000, Human. Immunol. 61: 764-779.*
Steinmetz et al 1993, Bioessays 15:613-615.*
Loirat et al 2000, J. immunology 165:4748-4755.*
Carmon, Lior, et al., "Novel Breast-Tumor-Associated MUC1 Peptides: Characterization in $D^b$-/- x ß Microglobulin (ß2m) Null Mice Transgenic for a Chimeric HLA-A2.1/$D^b$-ß2 Microglobulin Single Chain," *International Journal of Cancer*, vol. 85, pp. 391-397 (2000).
Hill, Adrian V.A., The Immunogenetics of Human Infectious Diseases, *Annual Review of Immunology*, vol. 16, pp. 593-616 (1998).
International Search Report dated Nov. 6, 2007 for PCT/IB2006/003967.
Abel Ureta-Vidal et al., Phenotypical and Functional Characterization of the $CD8^+$ T Cell Repertoire of *HLA-A2.1* Transgenic, $H$-$2K^{bo}D^{bo}$ Double Knockout Mice, Journal of Immunology, 1999, American Association of Immunologists, pp. 2555-2560.
Benet, Ariadna et al., "Diversity of Plasmodium falciparum vaccine candidate merizoite surface protein 4 (MSP4) in a natural population," *Molecular and Biochemical Parasitology*, Apr. 2004, vol. 134, No. 2, pp. 275-280, XP002447417.
Carmon, Lior, et al., "Novel Breast-Tumor-Associated MUC1 Peptides: Characterization in $D^b$-/- x ß Microglobulin (ß2m) Null Mice Transgenic for a Chimeric HLA-A2.1/$D^b$-ß2 Microglobulin Single Chain," *International Journal of Cancer* , vol. 85, pp. 391-397 (2000).
Elliott, Suzanne L., et al., "Peptide based cytotoxic T-cell vaccines; delivery of multiple epitopes. help, memory and problems," *Vaccine*, vol. 17, pp. 2009-2019 (1999).
Hill, Adrian V.A, The Immunogenetics of Human Infectious *Annual Review of Immunology*, vol. 16, pp. 593-616 (1998).
Hüseyin Firat et al., Comparative analysis of the $CD8^{30}$ T cell repertoires of *H-2* class I wild-type/*HLA-A2.1 H-2*and H-2 class I knockout/*HLA-A2.1* transgenic mice, 2002 the Japanese Society for Immunology, International Immunology, vol. 14, No. 8, pp. 925-934.

(Continued)

*Primary Examiner* — Christopher M Babic
*Assistant Examiner* — Kelaginamane Hiriyanna
(74) *Attorney, Agent, or Firm* — Finnegan, Henderson, Farabow, Garrett & Dunner L.L.P.

(57) ABSTRACT

The present invention relates to transgenic mice and isolated transgenic mouse cells, the mice and mouse cells comprising a disrupted H2 class I gene, a disrupted H2 class II gene, a functional HLA class I transgene, and a functional HLA class II transgene. In embodiments, the transgenic mouse or mouse cells are deficient for both H2 class I and class II molecules, wherein the transgenic mouse comprises a functional HLA class I transgene and a functional HLA class II transgene. In embodiments, the transgenic mouse or mouse cell has the genotype HLA-A2$^+$HLA-DR1$^+$β2m°IAβ°. The invention also relates to methods of using a transgenic mouse of the invention.

4 Claims, 10 Drawing Sheets

(56) References Cited

OTHER PUBLICATIONS

Kumar, Sanjai et al., "A multilateral effort to develop DNA vaccines against falciparum malaria," *Trends in Parasitology, Elsevier Current Trends*, vol. 18, No. 3, Mar. 2002, pp. 129-135, XP009072327.
Marshal, V. M. et al., "Close linkage of three merozoite surface protein genes on chromosome 2 of Plasmodium falciparum," *Molecular and Biochemical Parasitology, Elsevier Science Publishers*, Amsterdam, NL, vol. 94, 1998, pp. 13-25, XP002283184.
Pang, A. L. Y. et al.. "In vivo Expression and Immunological Studies of the 42-Kilodalton Carboxyl-terminal Processing fragment of Plasmodium falciparum Merozoite Surface Protein 1 in the Baculovirus-Silkworm System," *Infection and Immunity, American Society for Microbiology*, Washington, DC, US, vol. 70, No. 6. Jun. 2002, pp. 2772-2779, XP009054982.
Pascolo, Steve, et al., "HLA-A2.1-restricted Education and Cytolytic Activity of $CD8^+$T.Lymphocytes from ß2m) HLA-A2.1 Monochain Transgenic H-$2D^b$ ß2m Double Knockout Mice," *Journal of Experimental Medicine*, vol. 185, No. 12, pp. 2043-2051 (1997).
Pierre-Simon Rohrlich et al., HLA-B*0702 transgenic, $H$-$2K^bD^b$ double-knockout mice: phenotypical and functional characterization in response to influenza virus, 2003 the Japanese Society for Immunology, International Immunology, vol. 15, No. 6, pp. 765-772.
Polson, H. E. J. et al., "Gene polymorphism of Plasmodium falciparum merozoite surface proteins 4 and 5," *Molecular and Biochemical Parasitology, Elsevier Science Publishers*, Amsterdam, NL, vol. 142, No. 1, Jul. 2005, pp. 110-115, XP004944358.
S. Cheng et al., Characterization of HLA DR2 and DQ8 transgenic mouse with a new engineered mouse class II deletion, which lacks all endogenous class II genes, Journal of Autoimmunity 21 (2003) 195-199.
Vitiello Antonella et al., "Development of a Lipopeptide-based Therapeutic Vaccine to Treat Chronic HBC Infection," *Journal of Clinical Investigation*, vol. 95, pp. 341-349 (1995).
Vitiello, Antonella, et al., "Analysis of the HLA-restrict Influenza-specific Cytotoxic T Lymphocyte Response in Transgenic Mice Carrying a Chimeric Human-Mouse Class I Major Histocompatibility Complex," *Journal of Experimental Medicine*, vol. 173, No. 4, pp. 1007-1015 (1991).
Wang, Lina et al., "Structural and antigenic properties of merozoite surface protein 4 of Plasmodium falciparum," *Infection and Immunity*, vol. 67, No. 5, May 1999, pp. 2193-2200, XP002447378.
Wang, L. et al., "Differences in epitope recognition, isotype and titer of antisera to Plasmodium falciparum merozoite surface protein 4 raised by different modes of DNA or protein immunization," *Vaccine, Butterworth Scientific*, Guildford, GB, vol. 19, No. 7-8, Nov. 22, 2000, pp. 816-824, XP004225400.
Wu, Tieqiao et al., "Lack of sequence diversity in the gene encoding merozoite surface protein 5 of Plasmodium falciparum," *Molecular and Biochemical Parasitology*, vol. 103, No. 2, Oct. 15, 1999, pp. 243-250, XP002455544.
Alexander, Jeff, et al., "Derivation of HLA-A11/$K^b$ Transgenic Mice," *Journal of Immunology*, vol. 159, No. 10, pp. 4753-4761 (1997).
Baker, Alexander G.H., et al., "Analogus of CTL Epitopes MHC Class-I Binding Capacity Elicit Anti-Melanoma CTL Recognizing the Wild-Type Epitope," *Journal of Cancer*, vol. 70, pp. 302-309 (1997).
Barra, Claude, et al., "Abrogation of H-2-Restricted CTL Responses and Efficient Recognition of HLA-A3 Molecules in DBA/2 HLA/A24 Responder Mice," *Journal of Immunology*, vol. 150, No. 9, pp. 3681-3689 (1993).
Benmohamed, Lbachir, et al., "Induction of CTL Response by a Minimal Epitope Vaccine in HLA A*0201/DR1 Transgenic Mice: Dependence on HLA Class II Restricted $T_H$ Response," *Human Immunology*, vol. 61, No. 8, pp. 764-779 (2000).
Carmon, Lior, et al., "Novel Breast-Tumor-Associated MUC1 Peptides: Characterization in $D^b$ -/- x ß Microglobulin (ß2m) Null Mice Transgenic for a Chimeric HLA-A2.1/$D^b$-ß2 Microglobulin Single Chain," *International Journal of Cancer*, vol. 85, pp. 391-397 (2000).
Elliott, Suzanne L., et al., "Peptide based cytotoxic T-cell vaccines; delivery of multiple epitopes, help, memory and problems," *Vaccine*, vol. 17, pp. 2009-2019 (1999).
Epstein, Helen, et al., "Expression and Function of HLA-A2.1 in Transgenic Mice," European *Journal of Immunology*, vol. 7, pp. 1575-1583 (1989).
Hill Adrian V.A., The Immunogenetics of Human Infectious Diseases, *Annual Review of Immunology*, vol. 16, pp. 593-616 (1998).
Le, Al-Xuan T., "Cytotoxic T Cell Responses in HLA-A2.1 Transgenic Mice," *J. of Immunology*, vol. 142, No. 4, pp. 1366-1371 (1989).
Lustgarten, Joseph et al., "Identification of Her-2/Neu CTL Epitopes Using Double Transgenic Mice Expressing HLA-A-2.1 and Human CD.8," *Human Immunology*, vol. 52, No. 2, pp. 109-118 (1997).
Madson, Lars et al., "Mice lacking all conventional MHC class II genes," *Proceedings of the National Academy of Sciences*, vol. 96, pp. 10338-10343 (1999).
Nishimura, Yasuharu et al., "Expression of the Human MHC, HLA-DQW6 Genes Alters the Immune Response in C57BL/6 Mice," *Journal of Immunology*, vol. 145, No. 1, pp. 353-360 (1990).
Pajot, Anthony et al., "A mouse model of human adaptive immune functions: HLA-A2.1-/HLA-DR1-transgenic H-2 class I-/class II-knockout mice," *European Journal of Immunology*, vol. 34, No. 11, pp. 3060-3069 (2004).
Pajot, Anthony et al., Comparison of HLA-DRI transgenic mice deficient for murine MHC class II and HLA-DRI transgenic mice expressing endogenous murine MHC class II molecules, *International Immunology*, vol. 16, No. 9, pp. 1275-1282 (2004).
Pascolo, Steve, et al., "HLA-A2.1-restricted Education and Cytolytic Activity of $CD8^+$ T.Lymphocytes from ß2m) HLA-A2.1 Monochain Transgenic H-$2D^b$ ß2m Double Knockout Mice," *Journal of Experimental Medicine*, vol. 185, No. 12, pp. 2043-2051 (1997).
Steinmetz, Michael et al., "Recent experiments with MHC knockout mice: More questions than answers," *BioEssays*, vol. 15, No. 9, pp. 613-615 (1993).
Vitiello, Antonella et al., "Development of a Lipopeptide-based Therapeutic Vaccine to Treat Chronic HBC Infection," *Journal of Clinical Investigation*, vol. 95, pp. 341-349 (1995).
Vitiello, Antonella, et al., "Analysis of the HLA-restricted Influenza-specific Cytotoxic T Lymphocyte Response in Transgenic Mice Carrying a Chimeric Human-Mouse Class I Major Histocompatibility Complex," *Journal of Experimental Medicine*, vol. 173, No. 4, pp. 1007-1015 (1991).
Wentworth, Peggy A., et al., "Differences and similarities in the A2-1 restricted cytotoxic T Cell repertoire in humans and human leukocyte antigen-transgenic mice," *European Journal of Immunology*, vol. 29, No. 1 pp. 97-100 (1996).

\* cited by examiner

FIGURE 6

HLA-A2+DR1+CI-CII-T CD4 proliferative response to HLA-DR1 restricted epitopes following immunization with pcmv S2-S

HLA-A2+ DR1+ CI- CII- mice T CD8 cytotoxic response to the HLA-A2 restricted HBS (348-357) peptide following an immunization with pcmv S2/S

SEQUENCE LISTING

```
<160> NUMBER OF SEQ ID NOS: 20

<210> SEQ ID NO 1
<211> LENGTH: 4547
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1
gaattcttag gtttaaatac attgttttat ggattttaat acatccatct acagagccta      60
gcagggtgtc cttggcagtt gtcttttaat acctcatgtg ggtctgccta aaaactaatt     120
ttttatgtta atcaggttta aaaaatacta agtgttccta taaatatac acaacactta      180 gaagtggata cttcctaaaa acaggcagtg catgagcact agtgaggggc attgtgagtg     240
cattgaacag ttgcaacttt gaggtgaata aagcctgtaa tcgcttctgg ttgcaacata     300
taggaacaca gtcgctactt tgtattgagg agatgtcctg gactcacaca gaaactcaga     360
gctatggaat gatggtaaat ttaaaatact acaaccagga gtcacagata cattgtctgg     420
gaaactgcaa cttagtagct ttgtgagtcc tgttgtaagg cttttggaca catttataca     480 tcaagggct aaagtcacat ttttaccta ttagattcct gatcattcag gggttaccaa      540
gattctgcta cccactgtag ttaataaaca aagagcaaat tggtctctat tctgtctcat     600
gcactcaggc gcaactcttc ccgattaaaa acaaaaacaa caacaacaaa aatctacacc     660
tccattccca gagcaagctt actctctggc accaaactcc atgggatgat ttttcttcta     720
```

```
gaagagtcca ggtggacagg taaggagtgg gagtcaggga gtccagttca gggacagaga    780
ttacgggata aaaagtgaaa ggagagggac ggggcccatg ccgagggttt ctcccttgtt    840
tctcagacag ctcttgggcc aagactcagg gagacattga gacagagcgc ttggcacaga    900
agcagagggg tcagggcgaa gtcccagggc cccaggcgtg gctctcaggg tctcaggccc    960
cgaaggcggt gtatggattg gggagtccca gccttgggga ttccccaact ccgcagtttc   1020
ttttctccct ctcccaacct atgtagggtc cttcttcctg gatactcacg acgcggaccc   1080
agttctcact cccattgggt gtcgggtttc cagagaagcc aatcagtgtc gtcgcggtcg   1140
cggttctaaa gtccgcacgc acccaccggg actcagattc tccccagacg ccgaggatgg   1200
ccgtcatggc gccccgaacc ctcgtcctgc tactctcggg ggctctggcc ctgacccaga   1260
cctgggcgat ccagcgtact ccaaagattc aggtttactc acgtcatcca gcagagaatg   1320
gaaagtcaaa tttcctgaat tgctatgtgt ctgggtttca tccatccgac attgaagttg   1380
acttactgaa gaatggagag agaattgaaa aagtgggagca ttcagacttg tctttcagca   1440
aggactggtc tttctatctc ttgtactaca ctgaattcac ccccactgaa aaagatgagt   1500
atgcctgccg tgtgaaccat gtgactttgt cacagcccaa gatagttaag tgggatcgag   1560
acatgggagg tggcggatcc ggcggaggcg gctcggtgg cggcggctct ggatctcact   1620
ccatgaggta tttcttcaca tccgtgtccc ggcccggccg cggggagccc cgcttcatcg   1680
cagtgggcta cgtggacgac acgcagttcg tgcggttcga cagcgacgcc gcgagccaga   1740
ggatggagcc gcgggcgccg tggatagagc aggagggtcc ggagtattgg gacggggaga   1800
cacggaaagt gaaggcccac tcacagactc accgagtgga cctggggacc ctgcgcggct   1860
actacaacca gagcgaggcc ggtgagtgac cccggcccgg ggcgcaggtc acgacctctc   1920
atcccccacg gacgggccag gtcgcccaca gtctccgggt ccgagatccg ccccgaagcc   1980
gcggaccccc gagacccttg ccccgggaga ggcccaggcg cctttacccg gtttcatttt   2040
cagtttaggc caaaaatccc cccaggttgg tcggggcggg gcggggctcg ggggaccggg   2100
ctgaccgcgg ggtccgggcc aggttctcac accgtccaga ggatgtatgg ctgcgacgtg   2160
gggtcggact ggcgcttcct ccgcgggtac caccagtacg cctacgacgg caaggattac   2220
atcgccctga agaggaccct gcgctcttgg accgcggcgg acatggcagc tcagaccacc   2280
aagcacaagt gggaggcggc ccatgtggcg gagcagttga gagcctacct ggagggcacg   2340
tgcgtggagt ggctccgcag atacctggag aacgggaagg agacgctgca gcgcacgggt   2400 accagggggcc acggggcgcc tccctgatcg cctgtagatc ctgtgtgaca tacctgtacc   2460
ttgtcctcca gagtcagggg ctgggagtca ttttctctgg ctacagactt tgtgatggct   2520
gttcactcgg actgacagtt aacgttggtc agcaagatga ccacaatggt tgagtctcag   2580
tggtgggacc cttccagtag catatgcccc taattttgat atgaactcaa acagatatta   2640
aattacttat tttccattcc ctattccatt ctgtgactat ctctctcatg ctattgaaca   2700
tcacataagg atggccatgt tcacccactg gctcatgtgg attccctctt agcttctttg   2760
tcccaaaaga aaatgtgcag tcctgtgctg aggggaccag ctctgctttt ggtcactagt   2820
gcaatgacag tgtagtgtca aatagacaca tagttcactc tcatcattga tttaactgag   2880
tcttgtgtag atttcagttt gtcttgttaa ttgtggaatt tcttaaatct tccacacaga   2940
ttccccaaag gcacatgtga cccatcaccc cagatctaaa ggtgaagtca ccctgaggtg   3000
ctgggccctg ggcttctacc ctgctgacat caccctgacc tggcagttga atggggagga   3060
```

| | |
|---|---:|
| gctgacccag gacatggagc ttgtggagac caggcctgca ggggatggaa ccttccagaa | 3120 |
| gtgggcatct gtggtggtgc ctcttgggaa ggagcagaat tacacatgcc gtgtgtacca | 3180 |
| tgagggctg cctgagcccc tcaccctgag atggggtaag gagggtgtgg gtgcagagct | 3240 |
| ggggtcaggg aaagctggag ccctctgcag accctgagct ggtcagggat gagagctggg | 3300 |
| gtcataaccc tcaccttcat ttcctgtacc tgtccttccc agagcctcct ccgtccactg | 3360 |
| actcttacat ggtgatcgtt gctgttctgg gtgtccttgg agctatggcc atcattggag | 3420 |
| ctgtggtggc ttttgtgatg aagagaagga gaaacacagg taagaaaggg cagggtctga | 3480 |
| gttttctctc agcctccttt agaagtgtgc tctgctcatt aatggggaac acagccacac | 3540 |
| cccacattgc tactgtctct aactgggtct gctgtcagtt ctgggaattt ccagtgtcaa | 3600 |
| gatcttcctt gaactctcac agcttttctt ttcacaggtg gaaaaggagg ggactatgct | 3660 |
| ctggctccag gttagtgtgg ggacaggatc gtctggggga cattggagtg aagttggaga | 3720 |
| tgatgggagc tctgggaatc cataatagct cctccagaga aatcttctag gggcctgagt | 3780 |
| tgtgccatga agtgaataca ttcatgtaca tatgcatata catttgtttt gttttacccct | 3840 |
| aggctcccag agctctgaaa tgtctctccg agattgtaaa ggtgacactc tagggtctga | 3900 |
| ttggggaggg gcaatgtgga catgattggg tttcaggac tcccagaatc tcctgagagt | 3960 |
| gagtggtggg ttgctggaat gttgtcttca cagtgatggt tcatgactct cattctctag | 4020 |
| cgtgaagaca gctgcctgga ctgtactgag tgacagacga tgtgttcagg tctctcctgt | 4080 |
| gacatccaga gccctcagtt ctctttacac aacattgtct gatgttccct gtgagcttgg | 4140 |
| gttcagtgtg aagaactgtg gagcccagcc tgccctgcac accaggaccc tatccctgca | 4200 |
| ctgccctgtg ttcccttcca tagccaacct tgctgctcca gccaaacact ggggacatc | 4260 |
| tgcatcctgt aagctccatg ctaccctgag ctgcagctcc tcacttccac actgagaata | 4320 |
| ataatttgaa tgtgggtggc tggagagatg gctcagcgct gactgctctt ccaaaggtcc | 4380 |
| tgagttcaaa tcccagcaac cacatggtgg ctcacaacca tctgtaatgg gatctaacac | 4440 |
| cctcttctgc agtgtctgaa gacagctaca gtgtacttac atataataat aaataagtct | 4500 |
| ttaaaaaata atttgaaagt gacccttgat tgttaacatc ttgatct | 4547 |

<210> SEQ ID NO 2
<211> LENGTH: 29133
<212> TYPE: DNA
<213> ORGANISM: Homo sapiens

<400> SEQUENCE: 2

| | |
|---|---:|
| aaaaaattaa gtatataaag tttaaaaagt tagagtaagc taaggttaat tattgtagaa | 60 |
| aaacattttt cataaattta atgttgtctt agttacagta tttataaagt ctacagtaat | 120 |
| gtatagtaat gccttaggcc ctcgcattca ctcaccactc actcactgac tcatcagggc | 180 |
| aacttccagt cctgcaagct ccattcatgg taagtgtcct agaaagatct accatttaaa | 240 |
| aatctttcat atggtatttt caccacacct tttgtatgtt tagatacata aacagttagc | 300 |
| attgtgttac aattaccaat agtattcaat acagtcacat gctgtacagg tttgtcgcct | 360 |
| aggggtaata gggtgtacca tatagcctaa atgtatagta ggctataaca tctagtttgc | 420 |
| gtaaggacac tctgtgatgt tcacacaaag atgaaatcac ctaatgacac atttcttaga | 480 |
| gcttgtccct ttagctaagt gatgcatgac ttcagttttg ccccattcct agagcatagt | 540 |
| cctcaatgac tttcaatgaa aaacccgata gctttcatct tctcaatcct gaagagctga | 600 |
| aggagattta ggctgaactt aaagaaattt tcagcttagc tcattagtct tctactccat | 660 |

```
acatcttcaa catttaacaa gtgttttgaa aaagacacct acaaagtgct tgaagtcatc    720
aactctcaaa tcttgtcatt gcagcaccac gtcaaatgac aaaacacttg ctattttctt    780
agtccactgg aggagcctat tgtcagaggc caaacctgga ttattagctc caaacaagca    840
ctcagatcag taagtgtcct caggtgataa gtggttgttg ctacttggca tcaattcacc    900
agttcttctg aaacttacgt ctgttttgtt ttagggccct tatcaatggt aggtctttgt    960
ttcctcaaca ccactggaca gtgaaagatt ttgcactgcc tttcagaagt tgacacttta   1020
gttttttgtt ttaccttcta ccgtagcatc agaagttaac caacgtgttt tgaagaaacc   1080
agagtgtttg agatgcctca gttttctagt tacatcacac tggccccata attgctgctg   1140
atttctttct tacagcagaa aactgtagga aaattgtagc agaaaacttt tctacagcag   1200
aaaacggtag cagaaaaatg gcactaaaac gcagcgtaca cttgcaaaca gcaaatgcta   1260
ccaagagaaa cagtgatgtc caaacgtcag cttacatttg catggttctt ctttggaatt   1320
tttattcatc tagtcctatt tactttctta gctaaacaat gcttttttaaa aatataccta   1380 taaaatttta tcctattttt gtagttgttg ccagtgggac aatttgtcct actgtgaccc   1440
taatgcatct tatactgtgg tggaaaaaag aataagattt taaattgtgc tttctgaaaa   1500
actggatata gaaacagaca atggccagac catatataaa aataggcctg gctgggcacg   1560
gtggctcacg cctgtaatcc cagcactttg ggaggccaag gcggatggat catgaggtca   1620
agagatcgag accatcctgg ccaacatggt gaaacccctg cctctactaa aaatacaaat   1680
ttagctgggc atggtggcgc gcagctgtag tcccagctac tcgggaggct gaggcaggaa   1740
aatcacttga gcccaggagg tggaggttgc agtgagctga gatcgtgcca ctgcactcca   1800
gcctggcgac agagcaagac tccatctaag aaaaaaaaaa aaaaaataga cctttgaccc   1860
acagcctaca gcagcctgcc tggggaacca attcccttat cttcaataaa caatccagca   1920
aggtagtctg cttaagtccg acttgcagga agtcagattg ctgtctctag taacaatcca   1980
ggaggctaaa taataacttt tataacaatt gttttaaaat ggccaggact tgattaataa   2040
ctgacagttc ccccaatatt tgtgcctgct tccaacttag gaccaaccag ggaaagctaa   2100
atatgcatcc tacccaatta cataggatac tccacttcta gttaccccct aagcattccc   2160
catgccaaca gcctccaatc aggtcctttt taaccactat aaagtttcct acttctttgc   2220
ctgtctttga gtctctgcca aaatgcaaaa gatggtggct gactcctttg ttatagcaat   2280
ttgtgaataa tttttgctct tttcatttgg ttgatcttca tgtattttca cattattaag   2340
ctttatataa attaaaatcc aagaggctaa catttaatta atgacattta agatcttcta   2400
tatcggataa tgctatacat tatattaggt ttaatatttc tattaaatat agatttagta   2460
aattactaaa aatgctaaaa attcatcaaa tatatatgta agtacaaata aggaaaatgc   2520
aaagagagat attagaaagg ggtaatatat tcaggaataa atattcaaga tattttaagt   2580
tggagatatt gtctgttggt actaaatcaa tttcccccctg ttttgtgctt ttttccatat   2640 cacttgggt tgaagcctgg acaccacttc ttccagagtc cctttcttag gaaggcactc   2700
acttgcgatt agaaggcagt ggaaaattgc tgtcattctg cttctgacag caagtagcag   2760
cagctgccag gagtgtgggt ttgtttagtg ctgcagggcc aatagtagct tcctgcagtt   2820
cctgaccttt ggaagcacaa ttttgctttt tctgtcctta caaaacttt gcaatgcact   2880 tcactgtatt acatctctct gggcttaaaa taccttgagt gtgttttttc cccccttgtaa  2940 atctgggcta gactgaataa tcttgtaagt atgtaaatat aagcaactat tttaaaataa   3000
```

```
cctgggtttt taaatgtaat acagatgctc ttcaacttat gatggggtta actcccaata    3060
aatccagtgt aaattgaaaa tattgtgagt tgaaagtgta gagtataagt tgttcacctt    3120
catgatcatg tggctgaggc tgcctggcat tgtgaaagag tatcttactg agtatcgctg    3180
gtctggaata agatcaaaat ttaaagtatg gtttatacag aatggatatt gcttttacac    3240
cattgaaaag tcaaaaattc ctaagtcaaa ccatcttaag tcaggtgtgt ctgtagtttt    3300
aaaaaaatta caaataaaga atatccagtg ttgttgggag tgcagagaag atttacaagg    3360
taaacattga tttgtttaaa gtttgagaga aaaaattaga taatatgctt tatgattttt    3420
aaatgttaat ttcaaagtaa ttatacattc acaggagttg atgaaaatag tacagagagg    3480
tcccttgtac ccttcaccca gtttccccca atggttacat catacataac tatagcacaa    3540
tatcgaaaca aggaaatcga cactgataca atgtatttgc agttttctac tttatcacat    3600
gtgtagattc atgtaaccac cactgtgatc aaaatacaga actatattcc atcaccacaa    3660
agatcttcct catgccactc gccctcctta agagtcacac cattccccca cccccaccat    3720
ccctacactg tgccaaccac taatttgatt ttcatctgta taattttatc atttagaaaa    3780
tgttatataa atggaattat actatatgtg accttccgag actggcattt tgtactcaga    3840
ataatgccct tgggatctgt attaggtgct ccagagcggt tgtactaaca ggatatgtat    3900
atatagaaag atatttcttt taaagaattt gctcacatga ttgtggaagc ttactgagtc    3960
caaattctga tggaagaggc cagcagtgga ggagactggg acagagttgc agtttgagcc    4020
caaaggtagt ctgctgtgga accaggaaga gccaggattg cagatggagt ctgaggcaat    4080
ctgttggaga gttccctctt atgctagtca ggcattcaac tgattaaatg aggggaaccc    4140
agttatggag ggcaatgtac tttacttaaa atctactgac ttaaatatgt aactctcacc    4200
ccaaaactgc cagattatgt gaaattccat gtcctctact tggctccatt gacactcaga    4260
tggagtagat taaacaacag acatttactg aaagtcctca cttaacatca tcaataggtt    4320
cttagaagct gtgactttaa gcaaaatgac atataataaa actaatttga ccataggcta    4380
attcagcgat ccccaacatt tttggcacca gggactggtt ttgtggaaga aaattttgcc    4440
atggatgggg gttggggact agcggtggca gggagtggga tggcacaacc tagatccctc    4500
gcatgggcag tccacaatac agttcacaaa ggtttgcact cctgtgagaa tccaatgcct    4560
ctgccgatct gacagcaggc cattagtggt ctgtggccca ggggttggga acccctgggc    4620
taattgatgc gaacaagatt taagttccta tggcttattt ctggtcacaa acacatcacc    4680
aaactcctaa ataaagactc agaacacttc taatattaaa cattaaaata aatgggaact    4740
atatatacat ttaaggtagg tttataataa caagtaagat aattaattat ccagttttg    4800 gtgaattagt gagtgatggt ggtcacagtg gtggtgggtt acattaagga acaaatgttt    4860
gtaaaatgaa aatggtaagg agcacctcct gccaccacac agctcaaacg caaagaagaa    4920
caaatacgtt gaactcactg agtacttttg tacccccattg tttactattg tacagttgta    4980
tgaatatcat gtactttaca aatttttatt ttagaaacat ttctattcat tcgcttattc    5040
attttccaac ctgcttattc cagttcaagg tcatggatga ctggagccta tcccggcagc    5100
tcaaggacaa gagaggaacc aaccttgtat aggatgccat cccatccatt gtgggatgca    5160
gacacacaca cacatacaca cacacacaca cacacacaca aagtcactct gctgggacaa    5220
tttagactca ccaattaacc taacatgcat gtctttggga tgtgggataa aactcaaata    5280
cacaaagaaa acccatgcgg acgtggggag aacacacaaa ctcctcatgg ccagtggccc    5340
tggccaggaa cctatttatt ttctcaccaa cattgtaaca aaacgttgaa caaaacaatg    5400
```

```
ctataggagg accctctgtg tttctcacag tcctggaggc tgggaagtcc aagatcaaga    5460
tgctgacagg ttcaattcct ggtgaactta gaactgaagg ctctctggca ggggtgcctt    5520
gtggctgcag gctgggtata gaaactcagg ctccccacta ggcctccact tacagaatcc    5580
tgactgggag ggagagggtc tcatcagcgc tcccacatgg cctctactga caccaggaag    5640
ggagaagtgc ctccttacac ctggacagtg gtgaaagtcc cagctttcta cttggcctcc    5700
tctgacaaca ccttggcaaa gtgggtgagg agtgcttcct tgcaacaggg caggtggaag    5760
tccaggctct tcacatgggc ttcactaaca ccacagtgtg gaggtggctg attactgata    5820 ggcagggca aaagtcctag gtccccagtt ggcttcctct gacataagcc tgatgggtct    5880
aggtagtgtc tcattatcgc caggcaatgg gataagacaa agctcctcac tcagtgtttg    5940
ctgactgagg cgggatggaa gcccctgatt tttctgtatt tgactggagt agtgcggtta    6000
ctgtcagtta tctgcctggt aggctgctct ttcttgttcc cttggataga gaaacatgct    6060
ttccttagga tattttttgtc tgtgactact gatgttcct gttttccagt ttctccagca    6120
ctcattcctg gatatattag gcagaaagaa gacctatgaa actcaccact ctgtcattcc    6180
ccaatcccat ggtctgaggc caacctgctt ctcctctcca tcattcaagg gcttttttatg    6240 tctgtctgta gctgtactta gcaggaagaa taggaagaat tgtacctact tcatcttgtc    6300
ttagaaccag aaatctctca ccatattttt taaaatatgt ttttgtcata tattaaaata    6360
ttatacatct atccttagat ccttaaataa acatataatc tatccttaga gttaagttaa    6420
tttggtaaca aaaataaaac aagactaaaa ctattaattg tgttaaagcc ataaaaaata    6480
tgcaaatttt tgcccaaaat atgggaaatg tgcgtgtgtg tgtgtgtatc tcctatgtat    6540
acacataaaa aaagacataa aatgaaaatt gctgatgtat caatacccgg gggcagggag    6600
tattctcagg tttaactaag tactcatatt caagttttta ccataggcca cacctggctc    6660
tcagattcac ttagaaggat attagacagg agtcaaagta tgccaaagtg ctgaatcagg    6720 tcttttttctt cagtgggaga agttcttgaa acagttcata atttattcca ggtgctagtt    6780
tcatcctctg cccccatccc ccaagtgaca actcaggtac aaggagctga atttacacct    6840
gtggaagttg tgtccaccgt agcttagaat cctcatgtca tctacgagct agtacctctt    6900
ataacaaacc catgggcaca gcttccagag tccccgtaaa gggcatgctc agttacaagg    6960
gtcactgcat ttgaaaatac ccaaactatg ggtccccgtc atttgttacg gttcatgaaa    7020
tattcttccc agtaaagata caaaatgcca accagaagcc atttgtgcca taagcaatgt    7080
tgtctaaaaa tccagctgac attcttcctc catcaggttt ccagaaaaca gctagaaaat    7140
tagcctaaga ttaaatacat catggagaag tagaaagggt gttataaagc atttatccac    7200
aagattcaaa atgaaataca gttaattttg tccgttttaa gacattattt caaccttcaa    7260
attatttaaa agaagtacat cctatatttt gtgtgcttat tcaaaaaagg catggtaata    7320
cttataaaaa gactttaaat attttttataa gttttaaata ttttataagt aattttataa    7380
atgaaattac aaaccatttta agtgacctaa ttaaatcaaa cacactttga gtatgcacac    7440
aagaaaaaaa ttagttgaag catcctgact taagaaatcc ttgatctttc ataaggtgtc    7500
tgaatactca atgtcaaaaa cacttatgaa gaattaaaca ctgttgacca caagagggaa    7560
acctagtccc agttatacta taaattagaa aatcaaggga aaaatatgtg tcctgagaac    7620
ttttgaaata gtcacatata aacatagtat acaagaaaaa accaaccgtc atccctaccc    7680
aaggatatgt ttgtggtatg agtggttttta gtgttttgag tggactggtt cttggactcc    7740
```

```
acatattatt ggctacagag atagagactt gatttagaaa atcacagttg ccactttcta    7800
agtaagccct tgaccaaaag actagatttc tttaaaccca gttttctcag gtaaaatgga    7860
aatacaacta ttatctaata aatataagta agctttagtg tcatagtcat agcagtagta    7920
ttttcaattg gtaaaagaa actggacccc aaaaagaat ttcagtgaaa gcagtaacag      7980
tcttctggca tatttctcac ctttctttct accttaaagg ttcaaagttc ctaagtaatc    8040
tcagaaacct aaaatagttt attctctatc ctcactattg gttttaaaa aacattttgc     8100
agcatggacc actgctcatg tacagatgct ctccaactta acaatagggt tatgtcccaa    8160
taaacccatt ataacttgaa aatatcttaa gctgaaaatg catttaatac accaataaac    8220
ccatcataaa gttgaacaat cataagccaa attataagtc agagaccatc tgtattagct    8280
taagtcttgg aatggtttat tttttagatg ccatttagcc acttatattc tcttctattt    8340
tattgtgaga actaattccc ctcttacatt ctgtgcttga cccatgctat acttagtgtg    8400
aacaagagcc accttcttct catgacttct attttttgt gaaaatttcc ttcactcatt     8460
cacgacattt ggatttgaaa tcttacctac ttaagtactt taaaaaatca ttttctacca    8520
tctttcttat caggagcctc tagtgattcc ttctccacac ttctaacttc tcatcttcac    8580
actccttgtc ttcctaactt cactacagta agtgttttac atgtttagaa ctcagctcct    8640
ttactatgat tgctaaccat gtaccttaaa taaaccgtct tctagttttt tgtttcttac    8700
tctcaattat acctttaga aaagaattaa gagtagaaaa agactgctac atagacattc     8760
ttatgatctt cagaaatgag cacagatcat gcttaatgaa aaagatttc caaataatgc     8820
tgcatatgtc cagagaaaag gtggcagaaa tgactgtcgt ttgggggcac tattgtctgg    8880
acatggccag ttctcagaac tccagtccct aaattcccctt ctaactaaag gaaaagcctc   8940
ttaagggtct tatagaaatc ctgccacttt caccctgaaag aataatcttc agttatgtgg   9000
cacatggcca agagtaaaag tctttagtca cttggaagca gacagacact gtaatgctaa    9060
ataattggac ataacatgga acttactgag gcctcaaata tcaattttac tttgggaaaa    9120
agagcagcaa cttaaaaagt gattgaaagt aactcaagtt tattccttaa cagagtgatg    9180
cttaatctaa caaaaaacat gttatatgca cactcttctc cattaccttg taagaaaact    9240
ggactaggaa acacagctga aatggccagt tctgcctcca tttcctaaac cgtgttataa    9300
ttatgtctat gtgaccagta acagacaatg accatgattt atacttttc atatgtttgt     9360
tgttttgttt tcaatgttttg tggtctttcc tcagtatcag ctaagaggcc attaacacag    9420
atatctattt atggacatgc gagactgttg ttcacctctt ttgcagaatt cataaagaaa    9480
tgatggggaa aacacatcaa agatagagtg gataaagcaa atgtgccaca tatacaccat    9540
ggaatactat gcagccatga aaagaatga gttcatgtcc tttgcaggga catggatgaa     9600
gctggaaacc atcattctca gcaaaataac acaggaacag aaaaccaaac actgaatttt    9660
ctcactcata agtgggagtt gaacaatgag aacacatgga cacagggggcc tgttgggggg    9720
gtgggggggca aggggaggag agcattagga caaataccta gtgcttgagg agcttaaaac   9780
ctagatgacg ggttgatggg agcagaaaac caccacggca catgtatacc tatgtaacaa    9840
acctgcatgt tctgcacatg tatcccagaa cttaaagtag aataaaataa ataagtaaat    9900
aaggaatgat gggacaaaca agtttctgtt attgtctctc tactgaccaa agggtggtca    9960
gagagtatag gatgaagcag attttgtgata tccttgaata gatctgctct ttactatgaa  10020
ttctatcatc tactcccagc gtatgtggga aaggaccaa cttacttgcc tggaatttag     10080
tgaaattgtt ttctagggggg accaagagtt tcctctactt gatatgaagt tgggtggttg   10140
```

```
aagatgatag gattggcttc tgcttccatc agaatcctaa agggcagggt atatggacta    10200
gttggtattg gatcttggaa actgtgatgc attgggaatg gtcacactcc cagagtttgt    10260
ggacacaaag aatgttttag tgttccctac acaccagaca cgggccatga aggaatctga    10320
agagcctacc aaaccttgca aagagaaaa gctttacttg gaacatcatc caggctcaga    10380
gaacacaaat atttcatttc cagtaagacg tttctggtct ttttctcttc ctcccattcc    10440
ctgaacctac cctagatgag ctatggcctc aaagtgccag tagaacgtaa gaaggaagga    10500
gaaccacact cattcctgcc ttcaacaatt tacacaggga tagaaagaga tttatattaa    10560
atcaagttgg gactttcaat tattatatag taccaaacaa tctaattgct gaactaagat    10620
atacttgtgc aatttaaggg aattgtagaa tagcatatta attagaatca agaaaataat    10680
tcatgaagta tgctataatt cctacccaag cgcaggggaa tagcatctct aatgaaattc    10740
tctaaagagg caagagcagg cacaatgagt ttttgtttga ttaaagattc catttagtgc    10800
ttatccaacc tagcaattac atttgtatgc ttcagatgtt tttaaaaaaa taaacaaaag    10860
aaagtacctt aaataaagaa taggatcaaa tagtatttaa acaattgagt aaattaaaaa    10920
attatatgaa ttagattgat tgaaattgat actttcctaa ttctcctcct tcaacacaca    10980
gacacacaca cacacacaca cacacacaca cacgtatgca tacaaacaca tctgaattct    11040
ataaaatcat tctgaccttg atgagattcc atagtttact catgcaacag aacataatgt    11100
ctaaatgaag tttctggtct ctgttttaca tggatgattg agtaaaatca ttccctattc    11160
ctggaagaat agctaagaaa ggattcacag gtgaggacat gcgttttttc agaagatgag    11220
aacaaagatg agaagatgag agcaacagaa tgtcctatat cctaatgctc tgtgctgact    11280
tcggagtggc caatatgata gagatggaag gaactctgaa aacaaattgc cagaatttct    11340
aaggaacagg agatgttgag tgagtgaatc aagccatgga ctggctgtat gggggcagct    11400
attagagaca actacccta gacttctttg gtgattggtc aagctaatct tttccttcag    11460
agtctctcaa ttataagact tagcttgtgc catttagaac agacaagaac acagagaatt    11520
atagaacaat ctgactacag gttcttaagt tatagcaatg aaacttgtag ttggccggca    11580
ggaaaatatt ctgagatgtg gattcaaagt ttctaagtgt gcacacgtac acacacacac    11640
ccctacctgc atgcgttttc taatttacaa agactactca agtaaagagg ggtaatttca    11700 cacccccagga ggtctgtata aagataactc tggtctttaa agcatcgggt ttcaggtaga    11760
ggtgaagaga gaatgaatca aactcaaact gccatcctcc caggttaaag atgagtccag    11820
tcattgtgga gccctctatt aacacaggac atgctaggaa ggcccattaa cccactgccc    11880
tagcacattt gttaacgtcc tagtgcattt gttgatatca acagttcaca gttttattc    11940 tgatagggat ctattccagc agaccagctt ctgtgacctc tcaggatgcg aaaaagtaac    12000
acaagaaaag cttcttatgt agtgaattga gaaggaaata cctagatcaa tattccctca    12060
gcacctctgg taggaagtcc ttagtaggag aaaaacacca tgaagaccct tagtgcaaga    12120
ggaaaagggg gtaggggtg gtggaaggga agctaaaaga agggctgga ggttctcaga    12180 attcaaacca cacaaacaaa tgaagtattg aggtcccaga cttgatctgg gcccagtgtg    12240
aaagccctaa cttatttctc cagaagaata tgtcctctgg ttttagactt ggcactgtgg    12300
ggagaaccag agtgatctat ggtggatata cacacaaaca tagcacaca tatttgcatt    12360 tagtaatttt tgtaaaattt ccatttgctt ctctgatcct gtctgtatct ttgggaatag    12420
atgtaagaat attacatctc tcaggcttgc tctgccccag gtttctgaac gtggaataca    12480
```

```
tttctccagg gaaactcagt attatgagat tgggaggtg aagttaggc cacagccatc    12540
tcagggacag gtttcacaga catgagtttt ggcagcagcc ttgtgttcta aagacattta    12600
ctcctagggg ctctagagga tctgcaacat cagcagaggc ttcctgtggg ttcctgatct    12660
tttaaaatta gggttctgca gtgacttctg ctcctccaga cccctaaca gttttaaggg    12720
ctaattccct gtaatatatt cagttctgct tagactgatt acagggattc ctatttcttg    12780
actgaattct catggctata gtggctcgtc accatttgac atcaccaaga agtcctcatt    12840
caggtgcctt tggaaattcc ctcaaacaca caggaaatta gagtttgaaa gaaaacggag    12900
aaccatgagc actgtccaaa taggaacttc tctcctatca cagagaaagg gaactgaaag    12960
tcatttctca agtctcccaa atttagtaat ctcacaagaa gaaccaatca gtgttctagg    13020
actaaacagt gtcataagtt gctgagcaac aacttggatt gaagatgcta ttataatata    13080
tgaaatgtct ttgaatttac catgttttc tcaagcacca tttaagaaca aggcattatg    13140
gcagccagca aagggcagac atagaaaatt atacatggtt ttgcctctaa agaggagat    13200
gacaagctta aatcatagga tcagactctt agcacagact gataccatag gctctcatct    13260
ggcccattct cctgactctt tacctttcag gaaaggtatt cctgaaaaat tgcaggagag    13320
accatgctgt aggtctcttt ctagcgatct aggagttaat gccacagtgt gttcaaagcc    13380
ctttgatgcg atcagataat cagtaatgta tggaatattt gtgttcataa cttgtgagaa    13440
cggctgcatg gcaggacaag accccagcac aacagtatgg aaaatccacc ctaagcagac    13500
atgtcatgac tgatgttgaa caatggactc accagccagg cacggtggct catgcctgta    13560
atcccagcac tttgggaggc agaagcaggc agatcacgag gtcaggagat caaaaccatc    13620
ctggttaaca tggtgcaacc ccgtctctac tgaaaataca aaaaaaaa aaaaaaatt    13680
ggccgggcat ggtggcgggt gcctgtagtc ctagctactc gggaggctga ggcaggaaa    13740
tggcgtgaac ccaggaggca gagctttcag tgagccgaga tcgtgccact gcactccagc    13800
ctgggcgaca gagcaagact tccgtctcga aaacaaaaca acaacaaaaa aaacaatgga    13860
ttcaccatcc gatgggctcc ctcactgcca ggtcactctt catggaagta tttgtattcc    13920
agtcctttct gtggaaagaa cttaacattc tccttttcat aacactgtat cttcagaaac    13980
aagagagtcg aagtctccta attttcagga gtgtctatgt tgaacatcaa aatatattct    14040
ttagagcaga tctttaataa tcatatgaca agagaaaaac tttcataatc ttatgacatg    14100
agggaaggaa tattaaagcc gttctgtggg ttattatctc taacgttccc aatagaatag    14160
gctttgccag ctgggtgcgg tggctcatgc ctgtaatccc agcactttga gaggccaagg    14220
cgggcaaatc acgaggtcag gagtctgaga ccagcctgac caacatggtg aaaccccgtc    14280
tctactaaaa atacaaaaat tagccgggca tggtggtggg cgcctgtaat cccagctact    14340
caggaggctg aggcaggaga atcgcttgaa cccgggaggc ggagattaca atgagctgag    14400
atcacgccac caactccagc ttgggcgaca gagcaagact ctgtctaaaa aaaaaaaaa    14460
aaaaaaaaa aaaaaaaaa aaaaaaaat aggctttgcc cattatactc tctcatattc    14520
attgacctga atcctcaaat gaggtgtgtc cattagtcaa ctccaatctc ttgtcatata    14580
taagatggta gagatgagaa gaaggtagct cctttacagc ccactatttc cactaactac    14640
tacctgtgtt tcaagataca gcctttcatc cttctccagt gttgagagtg ttgaacctca    14700
gagtttctcc tcttatttc tctaaatgag atacaatgcc agccatccca agctcttggc    14760
ctgagttgtt catcttgaag tctaggactc caagaagcat gaaagagctt ctttagtgaa    14820
gctatgtcct cagtactgcc aaaattcaga caatctccat ggcctgacaa tttaccttct    14880
```

```
atttgggtaa tttattgtcc cttacgcaaa ctctccagct gtcatggcac agacatatga   14940
tctgtattta gctctcactt taggtgtttc cattgattct attctcacta atgtgcttca   15000
ggtatatccc tgtctagaac tcagattggg gttaaagagt ctgtccgtca ttgaccaaca   15060
gtcttaaata cttgatttgt tgtcgttgtt gtcctgtttg tttaagaact ttacttcttt   15120
atccaatgaa cggagtatct tgtgtcctgg accctttgca agaacccttc ccctagcaac   15180
agatgcgtca tctcaaaata ttttctgat tggccaaaga gtaattgatt tgcattttaa    15240
tggtcagact ctattacacc ccacattctc ttttctttta ttcttgtctg ttctgcctca   15300
ctcccgagct ctactgactc ccaacagagc gcccaagaag aaaatggcca taagtggagt   15360
ccctgtgcta ggatttttca tcatagctgt gctgatgagc gctcaggaat catgggctat   15420
caaaggtagg tgctgaggga atgaaatctg ggacgataga ctacgaagca ttggagaaaa   15480
gacctatgga catttggaag ataatgtgtg gagtgaaaga atagtgtgac aggtattatg   15540
tggtctcgac agaaagtata acaaattgtg gtttggtgga gttcttccct caccacaaac   15600
tgaagtaagt caaatttggt ttagaggatc aaaactgagt tgtgtattga tgaatagcaa   15660
ggtcctgcta caagccaaac tgggggtggg ggtgggggtg ggggaggaag aatattttct   15720
ggcaagcatt aacaagttat atttctgggc tttaattatt ctttctggaa aattagtaaa   15780
attaaaaact aaaaccaca catagttttg ctagaattaa atgaaaaaaa aagttattag    15840
ccctgttctt atctgaatac atgatacagt agttatttt tggagtgtaa atcctgtcgg    15900
tatatattga gcacatatat tgtgttgaag attactagaa ggaaaagtca tcaaaaagca   15960
acaatttacc ccaggaaaag gggagggaag gcatgctgat atgagttgcc tcatgggaca   16020
gtgatagcca ttccctgcct tcccatctcc atggtacagc agatcttata tcatgttaac   16080
ttagtaatat ttccaagaga gtagaaaaat gagtaaggaa atggggaatc tgatatatt    16140 ctctctcatc tccagagcaa cattggtgct gttgtaaaga tgtactgtag aaaagtattc   16200
ttcacccagc atgaccccca cagaaggtgt caggtagact tgaaataagc aaagtaataa   16260
cccagctccc atacccatag tggcaattgt agatttctat tgccccaaaa gagccataca   16320
tagggatact tacctagaaa gacagaggct cttcccttgg tttgtgaaga ggcagctagt   16380
atatttgtgt gtgtttgcat agatgcaaac ggtaaataaa ttcctaggtt tatcaataca   16440
cagtcaaaca ttaaagtctc tcatcttggc tgggcacggt ggctcacgcc tgtaatccca   16500
gcactttggg aggccgaggc aggcggatca cgaggtcaag agatcgagac cgtcctgggc   16560
aacatggtga accccgtct ctactaaaaa tacaaaaaat tagctgggta tggtggcaca    16620
cgcctgtagt cccagctact cgggaggctg aggcaggagg attgcttgag cccaggaggc   16680
ggaggttgca gtgagctgag atggtgccac tgcactccag cctggcgata gagcaagact   16740
ccgtctcaaa caaccaaacc aaaacaaaac aaaatatctc accttatctt tgaagactaa   16800
ggaaaaaaaa atctcccact catcgataca ctccacagag gcagcatact ctccaagtgt   16860
agctttctct tttcatgttc attattccct tggtgttggt tattctcaat gtcaatcata   16920
acagaacatc ttccataata acagtcccaa tttaaggagc attaagataa aaggtggaat   16980
tgccaaggtc aatccagacg agaaccttct catagaggta accaccgtgt gggtttggat   17040
gctgggaagc aggggactaa tgacgctaca aggtctcagt cttaatttt ggagtatttc    17100 agtccccagg tatattttcc atagatttgg cccttaaata aaagaagct tctgactcta    17160 aaatgtaaac agtgcttgtt acagtcttgt tgatatatta agaaattact caccttatct   17220
```

```
catttaatct taaaaacaaa cccctgacag gatcaaaacc acagcagggc tacataatag    17280
gaaaactata cataaatagg tagaataatc tgctcaggat cactaggtaa gttgctgaat    17340
aagaattcaa gatgttttg atcccagagt ttaaaaccca accttcaaa cagcgtttct      17400 ttcttcttag agtacaatgt tctgagaaag agatcctctg gaattctggc ctaagtgtat    17460
ttaatgcccg ggtaaagaaa gtgagagaac atttctcttt aggggctgct gctggatttc    17520 taaaagaaa ataatttctc agctagtaac atggagccaa acaacagctt cacaagactc     17580
tgggttcttt agccctcatc tccttcaatc caccctcttt ataaccagtc cttcttgttt    17640 ttccctccc agctttgttc agcagcatgc ccttcacca gaccttgtct tgtcactcat      17700
ccctactcgc catcattctt tcattcctct tggcccaatc tctctccacc acttcctgcc    17760
tacatgtatg taggttattc atttccctct cttgattccc cccacccaac tctcttctc     17820 cacttctcgc ctttcagaag aacatgtgat catccaggcc gagttctatc tgaatcctga    17880
ccaatcaggc gagtttatgt ttgactttga tggtgatgag attttccatg tggatatggc    17940
aaagaaggag acggtctggc ggcttgaaga atttggacga tttgccagct ttgaggctca    18000
aggtgcattg gccaacatag ctgtggacaa agccaacctg gaaatcatga caaagcgctc    18060
caactatact ccgatcacca atggtacctc cctctctgct gcactcctgg acatgggaat    18120
ccatagtttg aaagtagttg cttcagctct ttgtgttaga ttattgtaac tgattttccc    18180
tccaagggcc taaccttgcc attaacaagc cccaaattct catgccagag gtctgagaac    18240
tttatgggtt tgatcctatc ttgttgtgct caagtcttgt ctctgtcatc catggtctcc    18300
tacaaagtca ttgccctaag ttcatgctgg gggagccaga agggaagtcc ttggatatct    18360
tatacctcaa tattggctca atttcttggg gagggggtgc tgtcagagat tgttatctga    18420
ggatgtgaca tagatttctc agggcacaat ttcaactact ttttcagctt tagggttttt    18480
agatacgttt gtaccacaat tgagcatggg agggagaggg tgagcctaa gcagtgatgg     18540 ctgatttctg tcatgtctgt catgtgtccc ccagtacctc cagaggtaac tgtgctcacg    18600
aacagccctg tggaactgag agagcccaac gtcctcatct gtttcataga caagttcacc    18660
ccaccagtgg tcaatgtcac gtggcttcga aatggaaaac ctgtcaccac aggagtgtca    18720
gagacagtct tcctgcccag ggaagaccac ctttttccgca agttccacta tctcccttc    18780 ctgccctcaa ctgaggacgt ttacgactgc agggtggagc actggggctt ggatgagcct    18840
cttctcaagc actggggtat ggaccaacac tcaatctcct ttatttcaag gtttcctcct    18900
atgatgcttg tgtgaaactt ggtgttctaa ctgtttcata atatctgcta caattaatat    18960
aactgtcttc tcctactatc cagcttccgc cttttttaa tctgtaattc tctcaataca    19020
tcattctgtc ttcctcttct ttaatctatg aataactttt ctctttatta agaaccctac    19080
atttgattct gagtgttact tcttcccaca ctcattacca tgtactctgc cttatttccc    19140
cccagagttt gatgctccaa gccctctccc agagactaca gagaacgtgg tgtgtgccct    19200
gggcctgact gtgggtctgg tggcatcat tattgggacc atcttcatca tcaagggatt    19260
gcgcaaaagc aatgcagcag aacgcagggg gcctctgtaa ggcacatgga ggtgagttag    19320
gtgtggtcag aggaagacat atatggagat atctgaggga ggaaacagg gtggggaaag     19380 gaaatgtaat gcatttaaga gacaaggtag gaacagatgt ggctcttgat ttctctttgc    19440
tagaacgaat cagacattgg tatcatctgg tatcccaaag cttcagggtc tgtcatccct    19500
ttctatagac gggcacctg atcacggctc cagtcttaga aatcatctcc agtacctaaa    19560
accattgttt cacattagaa tactgagtct agggatctag aaaatactga gtctagggat    19620
```

```
ctagaaaaat aagcctcaag atttgggcac atcctagctt gtatttcctg gggcaggtca   19680
tcagttcaga agcatttcca gatcctggct cctttcaggt tagggtcaat tcattgcatg   19740
aaatgggaat ctcttagagg ccaatgcctg cttttgcttc tttagtctca aatgtagtat   19800
gagaaactct aaaaaaaggt aaagcatggt tgcttattat gttcagttgg agagtagggt   19860
atacagttag ttcatgttgg aaaggttaga tgaacattga agaattttg caaagtcaaa    19920 ggattaagag agaagaggaa ggaatctgaa gcaaggagct caaaactgat cttaaactcc   19980
ttggtaacta tgtgtgtctt gctataggtg atggtgtttc ttagagagaa gatcactgaa   20040
gaaacttctg ctttaatggc tttacaaagc tggcaatatt acaatccttg acctcagtga   20100
aagcagtcat cttcagcatt ttccagccct atagccaccc caagagtggt tatgcctcct   20160
cgattgctcc atactctaac atctagctgg cttccctgtc tattgccttt tcctgtatct   20220
attttcctct atttcctatc attttattat caccatgcaa tgcctctgga ataaaacata   20280
caggagtctg tctctgctat ggaatgcccc atggggcatc tcttgtgtac ttattgttta   20340
aggtttcctc aaactgtgat ttttctgaac acaataaact attttgaaga tcttgggtgg   20400 aattttggt gtttaagcca gttctttggg tggcggtggg gggtggggag tcggtcctgg    20460
ggaatatatg tgatcctttc ccggtaaaat atctgaatgt tgaatttatc ttataaattc   20520
tagaattcat cagacatatc ccggttcatt tgggcttggt ctcattttgt gcatctgcag   20580
gcaaccctct tgttgtggtc tagtcctcat caggaaaacc taaagtgggg ttggtttgtt   20640
gggagatctc tactgagcaa tgatataact ctatcttcag tagagtgaat ctgaaacccc   20700
aaggtatgga tctcagaatg catgggatgg aggggagcag atggggttag agtggggaga   20760
aggaagacag aagaatccat aaacattgca ggatttacat atcaacatcg ttcattccag   20820
atttaatgag caaagagatt ggacactgaa gactggcctt acccattctg ttagacatag   20880
tctcagatgc ctattttatt accgagagag tagtctgact gattcttgaa accaccttat   20940
atttgaagat gtgtctttga gtggaaaagc tgagtgaaat ttggggttgg ggagaaagat   21000
atgacattaa gatgagagga aggaatattt gaaacacgat gaactgttgc tcatttgtct   21060
ataaaactat gacttgatat ttatctctaa aatagtttct agaacctgcc ataaaccact   21120
aagataaact attcatgata gtgtggtaga ctgcaaataa atgctgttga aatgagttag   21180
gcttgggttt catcttggct gtatcattta ctagctatgt tttcactggt atcttactta   21240
acttagcctc acattactca tgaaaatact ggtgttaatt tttactacat tgaattaata   21300
tcagaattaa aaggaaaacg caagcaaagt aattagatac atgcttagtg ataataaaat   21360
attgcaaaaa attatacatt ctgttgtttt tctcaaaatt tctatagagt gatgataaaa   21420
atctaagaga agctaaacaa aacaaggata aaccaaagca tcatgacctt ctaagcctta   21480
ctaataaata agaagtttct cggctgggca cggtggctca cgcctgtaat ccagcacttt   21540
gggaggccga ggtgggcgga tcacaaggtc aggaaatcaa gaccatcctg ccaacatgg    21600 tgaaacccca tctctactaa aaatacaaaa attagccagg cgtggtgata ggcgcctgta   21660
atcccagcta ctctggaggt tgaggcagga gaatctcttg aatccgggag gcagaggttg   21720
cagtgagccg agatcgcacc actgcgctcc tgcctggcaa cagactgaga ctccgtctca   21780 aaaaaaaaa aaaaaaaaa aaaagtttc tctactgttg gttcagagaa tcaaagcaga     21840
atcttgagac tactgacggt agaataggta tgaatgtctt tcttacatga ctacaaactt   21900
tattataaaa taaatagctt aacacagaga atacactaaa acttagacaa gcatggatta   21960
```

```
agaaagcaaa aagtaaaccc atatactacc atgtaagaaa accattttg gccaggcgtg    22020 gtggctcacg cctgtaatcc cagcactttg ggaggccgag gcgggcggat cacgaggtca    22080
ggagatcgag accatcctgg ctaacatggt gaaaccccgt ctctactaaa aaaaaaaaa    22140 aaaattagcc gggtgtggtg gcgggtgcct gtagtcccag ctactcgaga gttgaggca    22200 ggaaaatggc gtgaacccaa gaggcagagc ttgcagtaag ccgagatcgc accactgcac    22260
tccagcctgg gcgacagagc gagactccat ctcaaaaaa agaaaaaaaa aaaaaaaaa    22320 aaaggaaaac cattttaata gactttatt tttagagctg ttttaagcta acagaaaaat    22380
tgcagaaatt gtatacagag ctcccccacc cccagtttct acaatgctta acatcctgta    22440
ttaatgtggt acacttgtta caattgatga accaatacta ataattatta ttaactaaaa    22500
ttcatagtta tacgagggtt cactctgtat tacacagtta tatgggttct gacaaataca    22560
taatatcata tatccaccat tacaggatta aacaaaatag cttcactgat ctaaaaatga    22620
cccaggctcc atctactcat ccttccttcc tccctctgaa ccattggcat tctctgagct    22680
atttactagt gttttgcctt tttcagaatg tcacatactt gtaatcatac agcatagagc    22740
tttttcagat gagattcttt tgcttagcca tatgcataca ggtttcctgc gtatattgtc    22800
atagcttgat agcttatttt tctttaatgt taaataatac tccattgtat aaatgtacta    22860
tggtttattt acccattaat ctattgaagg acatcttggt tgcttctaat ttttggcaat    22920
tatgaataaa gctgctataa acatccatga acagatgttt gtgcagacac aagttttcca    22980 cttttggataa atacatagaa gggcagttgc tggatcatat ggtaagagta tgtttagctt    23040
tgtaagaaac aactagaata tcttccaaaa tggctgtatc attttgcatt cctaccagca    23100
acgaatgaga gtccctgttg ttctatatcc ttgccagcat ttggtattct ggggtttggg    23160
atttcagcaa gaaagccatt ttaatatttt tttattttaa aataattata gattcagggg    23220
aaattgcaaa gacagtatag agacattctg catacgcctt cacccagttt ctccaaatgt    23280
ttatatttta agtaattata gcacagtagc aaaaccaaga aaataccttg atacaatgtg    23340
tatgtatagt tttatgcatg tcttaccaca tttgtagatt catgtaacca ccaccacaat    23400
caagcacaga gctattccat atcacagaga tcttcatcat gcttcccttt atagccaaat    23460 tcccccaca caatcacctt aacaacttaa accactaat ttctttgcta ttaatctcta    23520
gaatagtgtc atttttgaaaa tactagttaa atggaatcat gcagtatgtg actggtgttt    23580
ttcacttagc ataatacccca tgagatccat ccaagctgct gcatatatca acaatctttt    23640
tttttttatt gctaagtagt attccatggt ctaaatgcag cacagtttgc ttaactatt    23700 gcctattgaa ggacattttg gctgtttcta gtttggggtc actataaata aggctgtttt    23760
gaacatgtgt ttaaggtttt tctatgagca tgagttcatg agttttcatt tctctggtat    23820
aaatgtctgg gatataattc atgggcatat ggaaatatat gtttagtttt tcaagaaact    23880
gccaaactta gccaagtatg atggcttata cctgtaatcc cagcactttg ggaggccaag    23940
gaggaaggat aaattgaggc caggaatttg aggccagccc cagcgtctac acttttttt    24000 ttttttgaga cagagtctcg ctctgttgcc agactggagt gccatgatgc gatctcggct    24060
cactgcaacc tccgcctccc aggttcaagc aattcttctg cctcagcctc tcgagtagct    24120
gagactacag gtgcacacca ccacgcccaa ttaattttg tatttttagt agagacaggg    24180
tttcaccatg ttggccagga tggtcttgac ctcatgacct cgtgatccgc ttgccttggc    24240
ctcccaaagt gctgagatta caggcatgag ccaccgtgcc cggccaaatg ttttgttttg    24300
tttttgtttt ttgttttttt gtcaggtgga tgaggtggca tgcccctata gtcacagcta    24360
```

```
cttgggaggc tgaggtggga ggattgcttg agcccaggaa ttcgaggctg cagtgagcca   24420
ctgcacttca gcctatctga cagagcaaga tcctgtctcc aaaaggaagg aagggaggga   24480
agaagcaagg aaggaaggaa ggaaggaagg aaggaaggaa ggaaggagaa aaagaaggt    24540 agggagggag gaaggaaggg agggagggag gaaaaaagaa agaagaaagg aagttaaaaa   24600
gaagggaggg agggaggaag gaagaaagga aagatggaag aaaggaagga agggagggag   24660
gagaaagaga agaaaaaga aggaaggaag aaggaaggga gggagggaag ggaggaaggg    24720
agggagggtg aaaggaagga aagaaggaag gaaggagaaa gaaaaggaag agagaaagag   24780
aaagaaaaaa gaaagaagaa agaaagaaga agaaagagaa gagaaggaaa ggaaagaagg   24840
aaggaaagga aagaaagaaa aagaaaaagg aaggaaggaa gaaggaaggg aagaaagaaa   24900
aagaaagaaa gaaggaagga aagaaagaaa gaaagagaaa gaaagaaacc gataaactat   24960
tctctaattg ctttgtggga gtatggccac tttcatcata ttgattttc cttttttttt    25020 ttttttttt ttttttgcga tagagtctgg ctctgtcgcc caggctggag tgcaatggcg    25080
tgatttcggc tcactgaaac ctctgcctcc tgggttcagg tgattctcct gcctcagcct   25140
ccctagtagc tgggattaca ggtgcacacc atcacgcctg gtaattttt ttgtatttt     25200 actagagatg gggtttcacc atgttggcca ggttggtctc aaattcctga cctcaggtga   25260
ttcgcctgcc ttggcctccg gaagtgctag gattacagat gtgagccacc gcgcccagac   25320
aatattgatt cttccttttc catgaacatg atattttttt ccatttattt gtgtcatctc   25380
tgagttcttt gagcagtggt ttgtagtttt ccttgtagag atctttctcc tccctagtta   25440
gctgtattcc taggtatttc gtgtgtgtgt ggcaatcgtg aatgggatta cgttcctgat   25500
ttggctctca gcttgactgt tgtggtgtat aggaatgtta gtaattttc cacattaatt    25560 ttgaatgcca agacttcgct gaagttgtta attagcttaa agagcttttg ggctgagact   25620
atggggtttt cttgatatag gatcatgcca tctgcaaata ggcatagttc aatttcctct   25680
cttcctgttt ggatgccttt aattcttttt cttgcgtgtt gccctggcca agacttccaa   25740
tactatgttg gataggagta gtgagagagg gtatccttgt cttgcgctgg ttttcaaggg   25800
gaatgcttct agcttttcc catttagtat ggtattagct gtggggttgt cacagaaggc    25860
tcttattatt ttaagttatg ttcacttact actcagttta ttaagagttt ttaaatgaag   25920
ggatattgaa tttatcaaa aaccattcct gcatctattg agctaatcat gtggcttctg    25980
tctttagtac tgcttatgta atgaatcaaa tttattgatt tgcatatgtt gaactaacct   26040
tgcatcacca agataaagca tacttgatca ttgtagatta gcttttaat gtactgctgg    26100 attcagtttg ccagtatttt gtggaggatt tttgcataaa tcttcatcaa taatatttgc   26160
ctgaagtttt cttttgtgtg tgtgtctgcc aggttttggt gctgatcctg atgatgctgg   26220
cctcatagaa tgagttagag aggtatccct cttcctcaat ttttttggact aattataaca   26280 ggaatggtac cagctcttct tgtacatca ggcagaattc agctgtgaat tattctagtc     26340
ctaggggttt ttttgtttg gtagtctact tattactgat ttaatttctg agatcattat    26400
cagtctgttc agggattgaa tttcttcctg gttctgtctt gggagggtgt acgtgtccag   26460
aaatttatca atttcttcta gttttcctag tttatgtgca tagaggtgtt tttaatattc   26520
tctgatggtt atttgtgttt ctgtggggtc agtggtaata tccccattgt aatttctgag   26580
tgtgattatt tgaatcttct ctcttttctt ctttattagt ctaactagag gtctttttt    26640 tttattaatt ttttttagg aaaccaattc ctggactcat tgatcttttg agtgttgttt    26700
```

```
tttttttctgt ctcaatctcc tttagttcag ctctgatttt ggttatttct tgtcttctgc    26760
tagccttgat attggtttgt acctggttga ccagttcttt tagttgtgat gttaggttgt    26820
taaattgagg tctttctttt tcatgtgggc atttgatgca taaatttccc acttaacact    26880
gccttagctg tgtcccagag attctggtat gttgtatcgt tgttctcatc agttttaaag    26940
aacttctcaa tttcttcctt aatttcatta tttacacaaa agtcattcag gagcaggcgg    27000
ttcaacttcc atgtaattgt agggttttga atgaatttct tagtcttaat ttctaatttg    27060
attgcactgt tgtctgaaag attgtttttt atgatttcag ttcttgtgca tttgctgagg    27120
agtatttgac ttccgattat gtgatcaatt ttagagtaca tgccatgtgg tgatgagaag    27180
aatgtgtata ctgttgtttt ggtgtggata attctataga tgtctatcag gtccatttga    27240
ttcagtgctg agttcaagtc ctgaatatct ttgttaattt tttgtctcga tgatctgtct    27300
aatattatca gtgagttgtt aacatctcca agtattattg tgttggagtc taagtctctt    27360
tgaaggtccc taagaacttg ctttatgaat ctgggtgttc ctgtgttggg tgctgatctg    27420
gtttggctgt gttcccattc aaatctcacc ttgaattgta gctcccacaa ttctcacatg    27480
ccacgggagg cacctggtgg gaggtaattg aatcatgggt gcgggtcttt cccatgctat    27540
tctcatcata gtgaataagt ctcatgagat ctgatagttt tataaagagg agtttccctg    27600
cacaagttct cttgtcttgt ctgccaccat gtgagatgtg attttcacct tccatcatga    27660
ttgtgaggca tccctagcca tgtggaactg tcagtcaatt aaatttcttt cttttgtaaa    27720
ttgcccagtc tcaggtacat ctttgtcagc agcataacag actaatagag gagagtggag    27780
cactgctgaa aagatatctg aaaatgtgga agtgactttg gaactgggta acaggcagag    27840
gttgaaacag tttggagggc tcagaagaag ataggaaaat gtgggaaatt ttggaacttc    27900
ctagagactt gttgaatgcc tttgcccaaa atgctgatgg tgatgtggac aataatgtcc    27960
aggctaaggt agtctcagat ggaaatgagg aacttgttgg gaactggagc aaaggtgact    28020
cattatgctt tagcaaagag actggtggca ttttgtccct gtcctagaga cttgtggaac    28080
tttgaacttg agagagatga tttagggtat ctggcagaag atatttctaa gcagcaaagc    28140
attcaagagg ttacttgcgt gctgttaaag ccattcagtt ttataaggga agcagagcat    28200
aaatgtttgg aaaatttgca gcctgacaat gcaatagaaa agaaaatcca attttctgag    28260
gataaattca agctggctgc agaaaatttca tgggtaacga ggagctgaat gttaattatt    28320
aagacaatgg ggaaaatgtc tccaaggcat gtcagaggtg tttttttttt ttttccagag    28380
tctcgctctg tcgcccaggc tggagtgcag tggtatgatc tcagctcact gcaagctctg    28440
cctgccaggt tcatgccatt ctcctgcctc agccttccaa gtagctggga ctacaggcat    28500
ccgccaccac acctggctaa ttttttgtat ttttagtaga cggggttt caccatgtta    28560 gccaggatag tctcgatctc ctgacctcat gatccaccca cctcggcctc ccaaagtgct    28620
gggattacag gtgtgagcca ccatgcctgg ccatgtcaga ggtcttgatg gcagccctgc    28680
ccatcacagg cctggaggcc taggaggaaa gaatggtttc ttgggctggg cccagtgtcc    28740
ccgtgctgta tgcggtcttt ggacttggtg ccctgtgtct cagccgctcc agctgtgact    28800
aaaaggggcc aacatagagc tcaggccacg acttcagagg atgcaagccc caagccttgg    28860
cagcttccat gtggtgttga gcctacgtgt acacagaagt caagagttga ggtttgggaa    28920
cctccaccta gatttcagag gatgtatgga aatgcctgga tgtccaggca gaagtttgct    28980
gcctgggcag ggcactcatg tggaacctct gctagggcag tgcagaaagg aaatgtggag    29040
tgggcaccct cacacagagt tctcaatggg gcagtgccta gtggagtttt gaaaagagga    29100
```

| | |
|---|---|
| acaccatcct ccagactcca gagtgatgga tcc | 29133 |

<210> SEQ ID NO 3
<211> LENGTH: 22485
<212> TYPE: DNA
<213> ORGANISM: Homo sapiens

<400> SEQUENCE: 3

| | |
|---|---|
| cttgttaact actattgtat tctctgcttc tatgagcttg agtattttag ttacctcata | 60 |
| taagaggaat tctgcaatat ttgtcttcct gtaactggct tatttcactc agcataagcg | 120 |
| aaactaaaaa gcttttgcat agcaaagaaa acaataaaca gaatgaaaag ataacctgca | 180 |
| gaatggaaga aaatatttgc aaaccatata tttgataagg ggttaatttc aaaaatgtat | 240 |
| aaggaactca tacaactcaa gagcaaaaca accaaccaaa caaacaagct gattaaaaaa | 300 |
| tgggcaaagg acttgaacag atatgtcttg gaaaagatg ttatagacta aatgtttgtg | 360 |
| ttccctccta atcatatgtt aaatcctaag ccccaatatt ataggattag aaggtgggcc | 420 |
| ctttggaagg aattaggtct agagtctatc tagataaaca ctccaattaa ttgcccatat | 480 |
| gggaacacaa attggtttct gatggtgtaa agttattaag gaaaaataat aacaataaat | 540 |
| ggataaacag gatcaattc ttcttaccat ggagggagga tatgtatcct caacagaaga | 600 |
| ctgtgccatt taaaggccat attagtattc atcagagttg ataggaccct ttcctgtaag | 660 |
| atttcagcaa tgtcatccat cgaggaactt tgggtggagc cagtctttgc accatggcac | 720 |
| tatctaggtc atggctgtaa gtctacaagt gaaaaaacca tggtcaatat taatgatatt | 780 |
| gcaattagta tcagcaatac cactgaagga aacgttgaca gttaaaataa tttaggaggc | 840 |
| tgggcacagt ggctcacgcc tgtaatccca gcactttggg aggccaaggt caagagatag | 900 |
| agaccatcct agccaacatg gtgaaacccc atctccacta aaaatacaaa aattagctgg | 960 |
| gcatggtcgt gtgcacctgt agtcccagct actcggagg ctgaggcagg agaatagcct | 1020 |
| gaacccagga ggcagaggtt gcagttagtc aagatcacgg cactgcactc cagcctggca | 1080 |
| acagagccag actctgtctc aaaaaaaaaa aaagaaaaaa aagaaaaaaa aaagaattta | 1140 |
| gtgtttaaat cctgttctgg agagaaaata aacccatgcc tatgtatttt gcctcagtgg | 1200 |
| cagaaccagt tgcttttaga actgattctt gttatgcttt tttgttttc atagctttag | 1260 |
| aacttgtaat agcaataaag attcctcact tctggaaaaa ctcaaaaatt tctaataatc | 1320 |
| cttatattat cttctgctgt ggttattata aagtattttc ctctggttaa taatatagct | 1380 |
| atggcttaga ttatttttta ctagctggta ccttttttct tattctaaca gttgactaga | 1440 |
| catctcttta aggtcaaatc caaaattgtg aactatggac actgacaggg ttttgtttgc | 1500 |
| acccaaatca tctttagcat ctctagatgg atacttaata gtaccaagtt ttacacctt | 1560 |
| atcttgctgg tgtaaccct tgaatgacca catgaccaac acagggatgc tagcaatagt | 1620 |
| tagtgtggtt cttatgcttc attttctca gaattgctgt atgatactga gagttgcttt | 1680 |
| gtttgacagg cacacagggt aggaagagat gtcatgacaa aaggattagc taattctttt | 1740 |
| gcacacacat aagttgattt tatttaggta aaatgttgtt aacataaata agtactagta | 1800 |
| agtttacttt ttcaagataa taaattgtct gcaaggatga gctattagaa aaataactgg | 1860 |
| taaaagattt tattatttat tttaaataaa ataagcaaca aaccaggcac acacttcaca | 1920 |
| ggacagattg caaagaggtt ggtacagctc aacaggttca tcaatgtctt cactgtccac | 1980 |
| actgcagtca ctggggagtg ggctagtgga gcaccaaaat gaaattttga aaaataacct | 2040 |

```
ggcctatttt ggactggata gatagttgga tacttaccac agcacaatta acataagagc    2100
tagaaagata aatcaaaaga aaattctttg tacttacaat attagtagaa aggcctatgg    2160
gaattctagt tgttttctct atatgcaatg gcaagcattc tgttataaaa cagctaagtt    2220
gagccaaaga atgacatttg gaagttaaag aagtcctgtc aactgaccta gatagtgtca    2280
tggtgtaatg attggcgcta ccaaagtttc ttaatggagg acattgctga gattttactg    2340
gaaagggtcc tatcaagtgt gatgaatact aataaggcct ctaaatggca cagttttctg    2400
ttcaggatac atatcttcca tgctgagaag aaactggttc tgtttatcca tttattgtta    2460
ttgtcatttt ttctttagat ataaggatta gtaatctgct ttttacttta aattccagat    2520
agcagtggtt gctttctgaa aactcctgag aacattttgt gactgcttgg acaagtgaca    2580
gacattctat gataaccagg gcttgctgat agccaaaaaa gcctattttt ccaaaatgtg    2640
ttgcaagctt tcagccttac tgcaagtgag ccccattctg tgacaatcgg taggactcaa    2700
gacattctgt aatcctacca atgtcaacct gcctgttgtt cagcaaaagt ctgtgcttct    2760
gattttacct gtttagtcct gagaatgctg ggattttattt cctgtaaaac caagcctatg    2820
gtttcattca tcaagaccag agaccatgca acttccgtac ggaaaaccac tttcttccag    2880
aaaccaattt aattgccatt tcctcaggaa ataagctctc gtatttgaca cctctcacac    2940
acagcagagt tgagaggatt cttctcttgt tttcagtgca aaagttcagc ctagagatca    3000
cctgtacgat tgatggtttg gtgacagttg ctacattgtt tagcctgaac tatgcttata    3060
ttgaatattg aaggaaagtg tgagatatat aatttaaaga agcatatctg ttatagtttata    3120 agtgtgtcgc ctttaaaatt caggtaggac tcctcactga tgaatgggat taaggccctt    3180
gtaaaaaacg cttcacacag ttttttagcct cttgtctttc caccttctac catgtgagaa    3240
cacagtattc atcccctctg taggatgcaa ggtgccatct tggaagtgga gagcatgccc    3300
tttgccagac attgaacctg ctggtgcctt aatcttggac ttctcagcct ccatgtattc    3360
tttataaatt acccagtcta ccgtatttta tcacagcaca aataaactaa gacaacatct    3420
ttgttactca taaatgtata aaacatacag aatttagttc attgccattg ccatttttt    3480 aaatataaat ttgtatgatt tatgaatagc gtgtcaaatt tatataaaca aattttgaaa    3540
atttctcttt aactatattt tagtacattc ttgatgtaga attacttatt tttgcctctg    3600
catttatcct gtaataataa ggtgaaccttt agcttccttt cctagattac cacaccacaa    3660
ttagttaatt agtaaattac gatttcctat tatcaaatga aatgtgatat tctcctggtt    3720
gcaattgcac aattgtcaat agtactgaat tatcactgta gtgtaggaac acagtttgtt    3780
ctcaaatcca gggacttcta cccaacctct ccaagaaatc ttcaactttc cacattaaca    3840
gaaatatatt tttccaaagt aaacgagaca ctattttat tctattctga aatgatcaaa    3900
cttgcactac ttcgtgctga gaaattagaa atgatgattg agagtaataa accggagtta    3960
ggaatgttga ggctgttgtt atctttaata agaaggagat ttgtgcagga gctatgggtg    4020
tccttatgta acataaacgc aaactgtgtc atttccagag gagagtaacc atgatgatga    4080
ggggaatctt ttgaaggaac tagcattgct acacagtatc taccccaaag tctataaaat    4140
gttgccattc actaaaagaa gtagtcttac tgatttgcac agccatgaat taagggata    4200 aaataatttt tagtataagg gacataattc tctttagaaa ttgaatgtga ggtagtataa    4260
tacaacagta gagcctgagg ggtttggaat cacatatata ataccttggt tcaatagagt    4320
tgacagaaaa actctgcttt aaaataatta atattttatg tgaagagtgt tcaatccctc    4380
attcctggct cccattatga tctcctcatt tgtttgaggc tatggcccctt tactattcca    4440
```

```
cttctcttgt tttatcataa agggagatat aagaagactt tgctggccgg atgcactggc    4500
tcatgcctgt aatcccagca ctttgggagg ccgagttaca attctgagaa ttgctacaat    4560
tctgagtaca aagcaaaatg ctcaaaaatt gctgaagaaa ttttagtcat ttttattgca    4620
gcatggtgag tatcccaacc ctagaaacac taaggcacac aaggaaggag tgtgtatcag    4680
aactgtggta gggtgtgaat taatgcagaa ctttatctgt atagttgtac tttgaagtcc    4740
attctgaatc ttagatgcta catttatata aatataaagc ataataagta tctaaatgta    4800
gaattatatg tttaaaatta tatgattaca ttaactgatg taattcatag attttcccta    4860
gggttctgtt tcctgaacat tctgtaacgt attagttagc aaagtctttt tttttttga    4920 aactgagtct cactctatcg accagactgg agtgcagtgg catgctcccg actcactgca    4980
acctctgcct cctggaatca agcaattctc gtgcttcagc ctcctgagta gctgggatta    5040
caggcatgca ccaccacacc cagctgattt ttgtattttt tctgttagta gagacaaggt    5100
ttcaccatgt gggccaggct ggtttcaaac tcctgacctc aagtggtcca cccacctcgg    5160
cctcccaaag tgctgggatt acaggcatga cccactgtgt cctgccagca aagtcttctt    5220
atatattccc ttatgataaa acaagagaag tggaacagta aagggccata gcctcaatca    5280
aatgaggaaa tcctaatggg aaccaggaat gagggattga acactcttca cataaaatat    5340
taattatttt aaaactattg ggggaaattc agccagatat caggcaaaat tcaccccga    5400 tatttcacgt agtttctttt ctatattccc taagtgtcgg ccggtctgag aaataaaggg    5460
acagagtacc aaagagagaa attttaaagc tgggtgtccc caggagacgt cacatgttgg    5520
caggttctgt gatgccccac aagccacaaa accagcaagt ttttattagt gattttcaaa    5580
aggggagggg gagtgtatga ataggtgtg ggtcacagag atcacatgct tcacaaggta    5640
atagaatatc acaaggcaaa tggaggcagg gcgagatcac aggaccacag gaccggggcg    5700
aaattaaaat tgctaatgaa gtttcgggca ccattgtcat tgataacatc ttatcaggag    5760
acagggtttg agagcagaca accggtctga tcaaaaattt attaggcggg aatttcctca    5820
tcctaataag cctgggagcg ctatgggaga ctggggttta tttcatccct aagcttgacc    5880
acagaagacg gccacccct gaagcagcca tttcagaggc ctaacctcag ggaagtattc    5940
tctttctcag ggatgttcct tgctgagaaa aagaattcag cgatatttct cccatttgct    6000
tttgaaagaa gagaaatatg gctctgttcc acgtggctca ccagtggtca gagtttaagg    6060
ttatctctct tgttccctga acattgctgt tatcctgttc ttttttcaag gtgcccagat    6120
ttcatattgt tcaaacacac atgctctaca aacaattgt gcagttaaca caatcatcac    6180
agggtcctga ggtgacatac atcctcctca gattacaaag atgacaggat taagagatta    6240
aagtaaagac agggatagga aatcacaagg gtattgattg gggaagtgaa gtgtccatga    6300
aatcttcaca atttatgttg agagattgca gtaaagacag gtgtaagaaa ttataaagt    6360 attaatttgg ggaactaata aacgtccatg aaatcttcac aatctatgtt cttctgccat    6420
ggcttcaggc ggtccctcca ttcggggtcc ctgacttccc gcaacaaaaa cagagttgtt    6480
ctgtcaacag ctgactttga gtccttgatc ggtctctcag accctgaat acttggattg    6540 cacagttgac cttatcacat tgttagggta agtgcataca aaggcaactt cagaccctcc    6600
attgcacata ggtgggccct gcaagccgct tgcctgtgtg tgttctggag ctgccactaa    6660
acttggggac agcatcagga gatacacttg aaaaaacccct ttttactcag attaaattat    6720
taacaaactt tccatttcct ttaacttact aaagaatctc tacctgtaaa taggtacaga    6780
```

```
ttaaactcgc tagtcaacag ctatcattct gtcatatcaa cagatactcg tggctgctgc    6840
tccttgaggc atccacagaa tcacagcatt ttccagtatt gaaagacctg aaagatcacg    6900
gtgccttcat tttaactgtg agacatgaag taattttccc aagtctacaa cagtaagata    6960
tggtgcaata aggaccagat taaaagtctc ctgatttgca accatgttcc ctccatctcc    7020
tttactccta agcacactca cactcact cctgcaaaca attctcttgt caagtgggaa      7080
atgaatgctc ttacaaggct caaatttgtg aacacatcac tgaccagcac agagctggct    7140
aacaatagg acacaattaa ggtgttttac acgcaactgg ttcaaacctt tcaagtacta    7200
aattaaaaca atcctttaaa gaaggaaatt gtttcagaaa aggaccttca tacagcatct    7260
ctgaccagcg actgatgatg ctattgtact cagatgctga ttcgttctcc aacactagat    7320
tacccaatcc acgagcaagg aaatcagtaa cttcttccct ataatttgga atgtgggtgg    7380
agagggtca tagttctccc tgagtgagac tcacctgctc ctctggcccc tggtcctgtc     7440
ctgttctcca gcatggtgtg tctgaagttc cctggaggct cctgcatggc agctctgaca    7500
gtgacactga tggtgctgag ctccccactg gctttggctg gggacacccg acgtaagtgc    7560
acattgtggg tgctgaccta ctatggggtg gggaaaaaag ggagttgtgt taacattgtg    7620
cccaggccat gtcccttaag aaagtgtgac attttcttca gggattgccc atctttatca    7680
tatggatccc aaattatttc caccacaaat ggaacttggc tacttgccct attcatgaga    7740
ctgtgtaaag ggcctttgta caggccatgt tttacttta atctctacca ataaaacctt     7800
tgcatcacat gtcctcaggg tctttagagg atttagaaat aaggatgcta aaataaattc    7860
ctcatacagc acttcccttt atcatgttga cttatgtcag acgaaacaag gttttgtttt    7920
gaaaattttg tgggagtcaa aggaattcaa agggtctctc ctagacgatc ctgtgttgtc    7980
ctccacagga cctgtggtgt tggcccctct tcctcatatg tgaggatgta cccagtggcc    8040
tccccattgt ttccttttctt ttttttctga actccagtgt ttataaagcc tgtatccctg   8100
tagcatatgt aggttctctg acagaagtta tacttagtgc tctttctttc ttatggggaa    8160
aaatccctgg atctgaaact gacatcttta gtacttggag tcaccctaca ggtaaagacc    8220
atttatgagg tattcattgg tgcctcctct tgatcggtct ctcagacccc tgaatacttg    8280
gatactcctc aagaacttaa ggcatcctct gaaaaactgg cccagattag tgcttattat    8340
taatcttta taacctttct atacttgttt ctcctgcatg ctctaactag acatgacaga    8400
agagattcaa ctaacatagg ataaattata tgaaattcta tttttgtaag tcaaaaatag   8460
tcaaatacca gaaaattaat aatgttcaaa ctatatactc tgtgtggggt taccgagacg    8520
acgtggacat tgttcacatc taatagggct gaaagtcaat gaagaagtcc tggaaactcc    8580
ttgtcttact ggggtcttgt cctaaatttc ataggttcac ccatcatgcc ctcagctttc    8640
cttaattagc catgtctgct tatctctacc tccagtttct ctctattttt ccccagctat    8700
gttgtcatca tttccagaaa tctctaaaac ttgcaaagat ccttagcact atgagatcca    8760
ttgaaagaga taatttttt ttttttgaga cagggcttgg ttctgtcacc caggctgtag     8820
tgcagtggtg tgatctaggc tcactgcaac ctctgcttcc cacgctcaag tgatcctccc    8880
tcctcagcct ccagagtagc ggagactaca ggcaggcaaa catgtgcagc taattttcat    8940
gatttgtta gagatgagat tttgccatgt tgcccaggct gttcttaaac tcctggactc     9000
aagcaatcct cctgccttag cctcccaata tgctaggatt atagatgtga gccattgtgc    9060
ccaggcaaaa agagatgaac cttaatttaa aaatttcctt tttcttaaat cactgttctct   9120
ctatctgtga attcttcttc caactagaag gaggagaaag aagaagtttg cctgtatttc    9180
```

```
tcaccaggag gaggagtcta gtgtgatatc aaaatgaaag agtgctggag cttgatcccc   9240
ttcttgcttt ccaggatccc tgcagtgatc agttcccaca ccctggttta ttcatgtaaa   9300
gcacacttat ttttttcagc agctactctt tactgggctc cattctaagt tcaaatcatt   9360
ctatttgagt aagatagaga gggtcccgac tctcatggaa gttacacaag agtagaggag   9420
acagacacta acccaataag catttaacaa agaagaaaat gttagagaga catagtgcac   9480
tgaagaaaag acatcaggtt tgtgaaaaag agagacatgg attcacttac tttggttcat   9540
atgcttaggc agctataact gagaaagtga cattcagctg agacaacaaa ataaatagac   9600
agtcgtgaag atctaaagga cgaaagttcc agggagaatg aatgggggggg aagctctggt   9660
gtgggaaatt atgtggaagg acagaaagaa ggctagaggg actgaactat agcaagcaag   9720
gaaatggaga ggcagaagat gaggtaggac acagagagga agtcaggagc ctcatcatat   9780
tagactctga tggccatggt aaaaaaattg aattttattt tattttttatt tatttttttga  9840
gacgagatt tgttcttgtt gcccaggctg gagtgcaatg gcgcgatctc gactcactgc   9900
aacctctgcc tcctgggttc aagtgattct cctgcctcag cttcccaagt agctgggatt   9960
acaggtgcct gcgaccatac tcggcttatt tttttgtatt tttagtagag acagggtatc   10020
accatgttgg ccaggctggt ctcaaactcc tgacctcaga taatctgcct ggcttcccaa   10080
agtgctgaga ttacaggcgt gagccaccat gcccaacctg aattttattt gaatagatat   10140
gagaagctac tgtatggtta caaggacagt caatttatat tcgatttttt tttttgaga    10200
cagagtcttg ctctgttgcc caggctagat tgcagtggta caatctcagc tcactgcaac   10260
ctctgcctcc tgggttccag caattctcct gcctcagcct cccaagtagc tgagaccaca   10320
ggtacatgcc actacacctg ctaattttt tgtattttta gtagagatgg gtttcaccg    10380
tgttagccag gatggtcttg atctcctgac ctcgtgatcc actcccctcg gcctcccaaa   10440
gtgctgggat tacaggtgtg agccaccacg cccggcctat attcaattat taaaattaat   10500
tctagctact ctgtggggat tggattgttg ggtttcacaa gtggtcagga agactattta   10560
ggatcacagc agggaattct ccagggaaaa caggcttgtg gcttcataga gtgcattagt   10620
gataaagaca gtgaaaacga caaagtggac agactaggca tgtattttg cttagcttgt    10680
taatggatta ctctaaaggg ggtagaaaaa tcaagcttat tcctaaggat tttgttttga   10740
caaataagtg gatggtggtg tttattgaga taggaaaaac tgtgggagga aatgatttga   10800
agtgggtggt tggaaataaa agttttgttt aaatttgaga tgatttattg acatttatgt   10860
ggagcaatcc gaaggtcaat ggcatttaag agactcatgg tgaggtgagg ccagggcttc   10920
aggtatttat gttggcggca tcagtacgtg taatgtgtta aattccaggg agtggaagag   10980
gatacatagg gagatggatt gtgtggagaa aaagaagag ggtacaggcc agcaaagggg    11040
gctgagacag agcccaggga tgctggagaa acccaagag aacataatgg gtgtaagtca    11100
tggaaaatag attattttca aggagaaggg agaggtcaat tgtggtgagt accactaaga   11160
ggaggggggaa gtgagaacgt gacagagaag caagtgctgg gtttgctgga gttgatatttt  11220
gcagtcaatg gagtatccag ggaggaaact ggattggacc atttgaagag caagtagaag   11280
tgaggacgag gttaagggtg actattttaa gtagagagct tcagggaagg actgtgctct   11340
gggttcaggg agcctgctgg atctaaagga aaagggctga agaggctgaa gagaaggagg   11400
aggacctgtg aaccagagat actgagttat tattagcaag gaaatactag agggtccctg   11460
tgtgcagtgc tgactgctca tgcaaaaggt cacacagaca atatttcaca cagccagtat   11520
```

```
ttattagtga catagaatat gccagttatt actctaggtc atgagaatag agtgataaat    11580
aaaatgaatc tggtcgccat cggtatatgc catgtaacat tttgcagtga ctgtgtacca    11640
ggcctatgaa tttcagtatg caatttcaat aacgatcctg ttgtatctgt ggtgtttaaa    11700
aacatataca tctctggaat ctaaaattga gaggatataa gtaaaaccca gtattagaaa    11760
tttagtgctg gaaatcagac tgcagtttaa atctgagcat atagaaagtc cctttcttct    11820
atgtcagcag atgccttttg tgtgaggttt aggtatacta cattattaga cataaaccag    11880
tgattctgcc ctatgttttc agaatgacaa ttctttatga aactaataga agaacagaag    11940
acaattgcaa aatcatgatg aagatgctag tggctttaga accaaggaat acaaaaaata    12000
atgtgagctg cagttatagg gattataaaa gttaaaatgg gaatgcattt gagtgtttat    12060
tatgtgatca gtgctaataa gagtcatcat ttaattttac acttaacaat aatcctgtga    12120
ggattaagct attattaaat gcatttgata gattacaaaa aggcttaccg ttggtaaaaa    12180
ttgacccaag gggaagaggt cacatttta ttcagatttt ctgattctag agtttgagag    12240
tctgtccatc attagtgagt agtgacaata ctgtgtctaa attatcgaca gaatttctga    12300
tattcatatg tactatgttg tttcttagag tgtgggcaga gattcagggc tgctagttcc    12360
aatgtatagg agaaactttc attcattgtg catttatcat tttaaaagtt ctaggctggg    12420
tgcggtggct catgcctgta atcccagcac tttgggaggc caaggcgggc agatcacgag    12480
gtcaggagat gaagaccatc ctggctaaca tggtgaaacc tcgtctctac taaaaataca    12540
aaaaattagc tgggcgtggt ggtgtgcacc tgtagtccca gctacttggg aggctgaggc    12600
aggagaatgg catgaacctg ggaggcggag cttgcagtga gctgagatcg tgccactgca    12660
ctccagctcc accctgggca aaagagcgaa actccgtctc aaaaaaaaaa aaaagttcta    12720
tatgtctgtc atggcatatg ttgaagaaca caaggaagta ttaaatcact ccttctgagg    12780
tttgtctagc aagttgggct aggattgcca aataaaatac aggtttctag ttaaatctga    12840
atttcagata cacaactata atttactgaa aatccaaatg taacttggca tcctctgatt    12900
ttatttgcca aatctgtcaa ccctacatga gacacatgag catggattac ggtgttaccc    12960
atggaagcca cagccacagt gacagcgact tcacacatgt ttatttttta actttctctc    13020
tgtaaagaaa gtgcttagat aatttaggga taaaagata gacattgttt gatccaggat    13080
gcactcctct ctgccatcgt ttctaaaggg caaagagaga tttccacagg tcttactcac    13140
agtctgactc acagtctggg gacctgctca tgctttgaaa ctgtctgtat gagaatgtca    13200
ttttcttggt ttctcccttt ctgagggac ttgactacaa aactgagagt tctacctctg    13260
gccaaggctg gaaatttgat gcctgctagt attgttggga atgggagact gaaataaatg    13320
agttagttgg ggcattaaac aggaataaaa tagctgtggt tgtgattcat tactacaatt    13380
agtggactag tggcagagaa attaagaaag aagatgatgt gagagataaa ttatatgatt    13440
tggtaaggca agggaatcag taaatcttgg ttctgaacaa gttcattttc tggaaagata    13500
gcactgtact gggaccagaa ttctacaaaa catccgtttt atgtaagacc aagattttca    13560
acaaatattt ttcaatgcag ttctcagctg ctccataact aatagtgact tattcaacac    13620
agatattttc agatggttca cacccatgtt tcttacccag ggacagttca ccacccctcc    13680
ccttccctcc catcactctt gaggaacatg tggcaatgtt agaataattt ttggttgtca    13740
caacaggggt ttcttctgat atttaatgag cagaagccag ggacactgct agagaaccca    13800
caatgttcag aatagactcc atcaccaacc aagatttatc tcgtccaaaa tgtcaatagt    13860
gctgaggctg gaagcattgg ttcacactgt gctctttctg aaaaatgtag actcgctttt    13920
```

```
tttttttttt tttttgagat ggggtcttgc tctgtcgccc agactggagt gcagtggctc   13980
catctcagct cactacaacc tctgcctccc aggttcaagc gattctcctg tctcagcctc   14040
cccagtagct gggattacag gtgcaccctg ccatgcccgg ctaattttt  gtattttagt   14100
agagatgggg tttcaccatg ttgcccaggc tggtctcgaa ctcctgagct caggcaatcc   14160
acccgctttg gtctcccaaa gtgctaggat tacacgcatg agccaccgcg cccggcctag   14220
actcacatct tttatacact tactgcccaa ttcagttctt tatggtttat ttttgcttgt   14280
ttcattataa aaaactagac agttgcataa attcaaccac ttacttgttg aatccattta   14340
gtcaatgcaa gctcaacatt ttcatattta ttttttgcct tatgcaatat tgttcaacat   14400
tttcataagt tgttggtcag cactatctct attaactttc aacagtttgc ccttctaagt   14460
cacaaatagt gatgctgctg caattatttt tcactaacat gcctcagatt tctgtagtga   14520
ttctacattt gatattattc acaatgtaaa atgcttctat ttattcattt cacttttacc   14580
cacaggatta ttttttaagtt attttgtca ttttcacact tcaaccaaac ataaagacaa   14640
aaacatcaaa aatatgtaca tagtgttata cataggtgta tatttacaca catatatgca   14700
catatgttta tatgtattga aactacagaa gcacatgtca ccaataagag ctctgagaca   14760
cctttgacca cttacccttaa tcagatgaga tttgccaaat gagttttggg aacaaatttc   14820
ttttaactga atttctgagc tttgtggatt tagaaatgca actgaaagtt tgtggacatt   14880
tacgaggatc atagttttat tctccttaaa actcttcaat actttcccat tgtctttagt   14940
aaatccaaaa tcctaacacc actcacgagg cttttcaaca cctggcttct tgtgatttct   15000
ccaatctaac cttttacccct ccttccccctc agcctctctg ctttagtgaa ctttgttcta   15060
gttttttgaa gttcatcatc aattcaagct tttgtacatg ggatttccta aacctgaaat   15120
gtgcctccgg ttttgtccaa acagacacac aggctccact ctgcccctg  gctcacacct   15180
gcttaacttg ttaagtcaca tctgtaactg tcactcttct ctggcaccct aaaggaattg   15240
agatcatcct attattctct gttctagaac tccacacttc tgaaatttct cattcctgtc   15300
taagctcttg tgtgtttggt ttttggccat cactttcact gctcttaaag ctcccccagc   15360
ggagtggaga ggtctgtttt cccgtgtttg gattcctaga ggcagcgcag gcctggcaca   15420
aggtcatcac taaggaagtg ttcacaggat gaaagcggtg cgtgctgttt aaggaaaggg   15480
taaagccttt aaatggtaaa gggttgagag aaggagcaaa gtgcctttgg ggtggaggct   15540
cccaggagga ggcggcgcgg gctgcggtgc tggacggatc ctcctccagc tcctgcctgg   15600
aggtctccag aacaggctgg aggcaggag  ggggtcccaa aagccttggg atcagaggta   15660
gttttttccac ctggtccccc agaccccgt  ccgcctcaga aagacagagg atgagcccct   15720
gggctgcgtg ttgtcggggt tgcggtggg  gccagatagt gtcttccccg gaggccgctt   15780
ctgtaaccgg atcgttcttg tccccccagc acgtttcttg gagcaggtta aacatgagtg   15840
tcatttcttc aacgggacgg agcgggtgcg gttcctggac agatacttct atcaccaaga   15900
ggagtacgtg cgcttcgaca gcgacgtggg ggagtaccgg gcggtgacgg agctggggcg   15960
gcctgatgcc gagtactgga acagccagaa ggacctcctg gagcagaagc gggccgcggt   16020
ggacacctac tgcagacaca actacgggt  tggtgagagc ttcacagtgc agcggcgagg   16080
tgagcgcggc gcggggcggg gcctgagtcc ctgtgagcgg agaatctgag tgtgtgtgtg   16140
tgtgtgtgtg tgtgtgtgtg tgtgtgtgtg tgtgagagag agagagagag agagagagag   16200
agagagcgcc atctgtgagc atttagaatc ctctctatcc tgagcaagga gttctgcggg   16260
```

```
cacaggtgtg tgtgtagagt gtggatttgt ccgtgtctgt gaggctgttg tgggagggga    16320
ggcaggaggg ggctgcttct tattcttgga gacttctgtg gggaggtgac aagggaggtg    16380
ggtgctgggg gctggagaga gaggcgacct tgattgtctc gggtccttag agatgcaagg    16440
aagggaaatg tatggggtgt gtggttgggg tgaaggttta ggggaggaga gctgaggggt    16500
aaggaaggtt tgggataatg tgaagaggcc agtttcagac tgtccctggc acacacccett    16560 catgtaatct ctgaaataaa agtgtgtgct gtttgtttgt aaaagcatta gattaacttc    16620
taggggaatt gagtagacct ctgaggcacc tctgaagctt ctttaggtat aaatttcttg    16680
ctagtttttt gttttcttag tgttatattt ttacatagtt gaaatgactg tgaaactaac    16740
tttttgaatt aaagtttgaa aacactgtta ctatttatt ataatgctaa taatttcata    16800
gttacttttt aaatatataa tagttgtgac acaaattacc tcactttctt tgttttttt    16860 tttcttacac tttaagtttt agggtacatg tgcacaacgt gcaggtttgt tacatatgta    16920
tacatgtgcc atgttggtgt gctgcaccca ttaactcgtc atttaacatt aggtatatct    16980
cctaatgcta tccctcccca cccccccacc ccacaacagg ccccagtgtg tgatgttccc    17040
cttcctgtgt ccatgtgttc tcactgttca attcccacct atgagtgaga acatgcggtg    17100
ttcggttttt tgtccttgcc atagtttgct gagaatgatg gtttccagct tcatccatgt    17160
ccctacaaag gacatgaact cattctttt tgtggctgca tagtattcca tagtgtatat    17220
gtgccacatt ttcttaatcc agtctatcat tgttggacat ttgggttggt tccaagtctt    17280
tgctattgtg aatagtgccg caataaacat acatgtgcat atgtctttat agcagcatga    17340
tttataatcc ttgggttata tacccagtaa tgggatggct gggtcaaatg gtatttctag    17400
ttctagatcc ctgaggaatc gccacactga cttccacaat ggttgaacta gtttagagtc    17460
ccaccaacag ggtaaaagtg ttcctatttc tccacatcct ctccagcacc tgttgcttcc    17520
tgacttttta atgatcgcca ttctaactgg tgtgagatgg tatctcattg tggttttgat    17580
ttgcaattct ctgatggcca gtgatgatga gcattttttc atgtgtcttt tggctgcata    17640
aatgtcttct tttgagaagt gtctgttcat gtcctttgcc cacttttga tggggtattt    17700 tgttttttc ttgtaaattt gtttgagttc attgcagatt ctggatatta gcccttttgtc    17760 atatgagtag attgcaaaaa ttttctccca ttctgtaggt tgcctcttca ctctgatggt    17820 agttctttt gctgtgcaga agctctttag tttaattaga tcccatttgt ccattttggc    17880
ttttgttgcc attgcttttg gtgttttaga catgaagttc ttgcccatgc ctatgtcctg    17940
aatggtattg cctaggtttt cttctagggt ttttatggtt tcaggtctaa catttaagtc    18000
tttaatccat cttgaattaa tttttgtata agcaaattac gtcactttcc ccattgatga    18060
cctttattat gacattcacc aatagttgaa aatgtatgtt tctggttaat ttttgattta    18120
tatttttttg atttgtaatt attttgaatt attttgacct atttattggc cagttgtaat    18180
tactgctctg ctctacgaat tacctgttgt atttggtagg taatggacaa tgatctattg    18240
tctcttatct ttagggctta gtatttttct cagtgacttt gtgggtttgt tgtactgtaa    18300
gattattaac actttattga tatttgattc agtattttct ccagtttgtg gtatgtatat    18360
tttgaaaatt cttttccatg ttaagaattt gaacattttt atttaataaa atatattgca    18420
aaatgttaat taatgattca caaactagct caagtctacc attttgtggt attgatgtct    18480
ccaggtttct ccttccttct taaaaaaaaa tgtatttatt gagagtatgc tagtgtcagg    18540
gatttcccta ggcataagca ctccaagtaa tgagtcccag acactgcctt gatccaaatg    18600
tcattctgga aagaaaaatc atttttacagt gataagccta ataatagtta tacttgtttt    18660
```

```
gcctgggaga tgcattgatc agctaaatgt aaatataaga actttcaaaa ctaaaatgac   18720
gttccttaat ctttctctct gctttaggaa tcatgctttc ttaggaactt aaagatttgg   18780
agaatcattt ctgtctgtcc caccttccca ggagcataac catttctgtg gtgttctaag   18840
gtgtgagtgc atggcagtag tattcctaaa aatccatatt cagtttcctc atgtgcccta   18900
ctccgtccct ttctctatcc acattgcttt aaatcatatt tttctctcaa ggtgtacaag   18960
gatgataaat aggtgccaag tggagaaccc aagtgtgacg agccctctca cagtagaatg   19020
gagtgagaag ctttctgacc tcataaattg aaggctatcg taattcattc ttttatatat   19080
tttacttgca ttaatcctca tataacctca agaggtaaat taatataatt atcctccatt   19140
attggagaga aagttgagac acaaaagaat caaaaactct tccaggatca accagtaaaa   19200
ggcagacctt ggatttgaac caggcaacct ggctcagaag tcagttttaa ttaccacact   19260
ctgtactttc aaagatttgt aaacgctttg acaatgcatg tcaatttcaa gctatgaaga   19320
gccaaacata attttcaca atatctctca aatctaatgg gtccccacta taaagattaa   19380
attccaggct gatgacactg tgaggccaca tggccagctg tgctggaggc ctgctcaagg   19440
ccagagccta ggtttacaga gaagcagaca aaaagctaaa caaggagact tactctgtct   19500
gcatgactta ttccctctac cttgtttct cctagtctat cctgaggtga ctgtgtatcc   19560
tgcaaagacc cagcccctgc agcaccacaa cctcctggtc tgctctgtga atggtttcta   19620
tccaggcagc attgaagtca ggtggttccg gaacggccag gaagagaaga ctggggtggt   19680
gtccacaggc ctgatccaga atggagactg gaccttccag accctggtga tgctggaaac   19740
agttcctcgg agtggagagg tttacacctg ccaagtggag cacccaagcc tgacgagccc   19800
tctcacagtg gaatggagtg agcagctttc tgacttcata aatttctcac ccaccaagac   19860
gcgaacttta ctaatccctg agtatcaggc ttcctcctatc ccacatccta tttcatttg    19920 ctccacgttc tcatctccat cagcacaggt cactgggggg tagccctgta atactttcta   19980
gaaacacctg taccccctgg ggaagcagtc atgcctgcca ggcaggagag gctgtccctc   20040
ttttgaacct ccccatgatg tcacaagtcg gggtcacctg ctgtctgtgg gctccaggcc   20100
ctgcctctgg gtctgagact gagtttctgg tactgttgct ctgagtcgtt tgttgtaatc   20160
tgagaagagg agaagtatag ggaccttcct gacatgaggg gagtccaatc tcagctccgc   20220
cttttattag atctgtcact ctaggcaact acttaacctc attgggtctc aggctttctg   20280
ttcatcagat gttgaagtcc tgtcttacat caaggctgta atatttgaat gagtttgatg   20340
actgaacctt gtaactgttc agtgtgattt gaaaaccttt ctcaagaaat ggtcagttat   20400
tttagttctt gcagagcagc cttctttctc attttcaaag ctctgaatct caaggtgtca   20460
attaaagagg ttccatttgg gataaaaatc actaaacctg gcttcctctc tcaggagcac   20520
ggtctgaatc tgcacagagc aagatgctga gtggagtcgg gggcttcgtg ctgggcctgc   20580
tcttccttgg ggccgggctg ttcatctact tcaggaatca gaaaggtgag gagcctttgg   20640
tagctggctg tctccatacg cttttctgga ggaggaacta tggctttgct gaagttggtt   20700
ctcagcatat gaatggccct ggataaagcc tctctactcc caaatgacct ccaatgttct   20760
gcaaatccag aaatcatcag tgcatggttg ctatgtcaaa gcataatagc ttgtggccta   20820
cagagataac agaaagatta acaggtatag gtgctttggt tgagatcgtg gagcaaatta   20880
aggaagagca actaaagcta atacaattac actggatcct gtgacagaca cttcacactt   20940
catgggtcac atggtctgtt tctgctcctc tctgccctgg ctggtgtggg ttgtggtgtc   21000
```

```
agagaactct caggtgggag atctggagct gggacattgt gttggaggac agatttgctt   21060
ccatatcctt taagtgtata tcttctcttt ttcctaggac actctggact tcagccaaca   21120
ggtaatacct tttcatcctc tttaagaaac agatttggag gccaggcgca gtggctcacg   21180
cctgtaatcc cagcactttg ggaggccgag gcgggcgaat catgaggtca ggagttcgag   21240
accagcctga ccaacgtggt gaaaccccgt ctctactaaa aatacaaaaa aaaatcagtc   21300
gggcgtggtg gtgtgcgcct gtaatcccag ctactcagga ggccaaggca ggagaatcgc   21360
tggaacccag gaggcagagg ttgcagtgag ccgagattgg gccactgcac tccagcctag   21420
gtgacagagt gagaccccat ctcaaaaaaa caaaaaaaag aaagaaagaa acagatttcc   21480
tttccctaga atgatggtag aggtaataag gcatgagaca gaagtaatag caaagacatt   21540
ggatccaaat ttctgatcag gcaatttaca ccagaactcc tcctctccac ttagaaaagg   21600
cctgtgctct gcaggagtat tgactcatgg agacttcaga acttgttttt cttcttcctg   21660
cagtgctctc atctgagtcc ttgaaagagg gcaaaataaa ctgttagtag agccaggtct   21720
gaaaacaaca ctttcttgcg tctctgcagg attcctgagc tgaagtgaag atgaccacat   21780
tcaaggaaga accttctgcc ccagctttgc aggatgaaac acttccccgc ttggctctca   21840
ttcttccaca agagagacct ttctccggac ctggttgcta ctggttcagc agctctgcag   21900
aaaatgtcct cccttgtggc tgcctcagct cgtacctttg gcctgaagtc ccagcattaa   21960
tggcagcccc tcatcttcca agttttgtgc tccccttttac ctaatgcttc ctgcctccca   22020
tgcatctgta ctcctgctgt gccacaaaca cattacatta ttaaatgttt ctcaaacatg   22080
gagttaaaaa tcgtctggtc atttggcccc aaggacaaaa aataaaaaga aagaaaaag    22140 tgaagattat ttcccgatag aataatggtt ttcatggata tgtcataagt atgtgagata   22200
gtgcatatgt taaataggtt gatttagaca ttttacacta caggcatata tcaaaacttc   22260
atgctgtatg acataaatgc acaattttta cttgtcaatt taaaaagtaa acctaacgtt   22320
taaaaaggtg atgcataaaa actgagaaca gactataaga actgaaacaa acttggcaaa   22380
catgagatga taaaccagct agcaagtcaa tcagaactct ttctcaaccc cgtctacaat   22440
attgtgtgtc tataactgta aattagtata tagttttttca ttcca                 22485
```

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cattgagaca gagcgcctgg cacagaagca g                                   31

<210> SEQ ID NO 6

```
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggatgacgtg agtaaacctg aatctttgga gtacgc                              36

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttcttcaacg ggacggagcg ggtg                                           24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctgcactgtg aagctctcac caac                                           24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctccaagccc tctcccagag                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atgtgcctta cagaggcccc                                                20

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Leu Ser Pro Thr Val Trp Leu Ser Val
1               5                   10

<210> SEQ ID NO 12
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Leu Ser Leu Leu Val Pro Phe Val
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Leu Ser Pro Phe Leu Pro Leu
1               5

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ala Gly Phe Phe Leu Leu Thr Arg Ile Leu Thr Ile Pro Gln Ser
1               5                   10                  15

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gly Leu Tyr Phe Pro Ala Gly Gly Ser Ser Ser Gly
1               5                   10

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Gln Trp Asn Ser Thr Thr Phe His Gln Thr Leu Gln Asp Pro Arg
1               5                   10                  15

Val Arg Gly Leu Tyr Phe Pro Ala Gly Gly
            20                  25

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 17

Thr Ser Leu Asn Phe Leu Gly Gly Thr Thr Val Cys Leu Gly Gln
1               5                   10                  15

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Leu Leu Val Pro Phe Val Gln Trp Phe Val Gly Leu Ser Pro Thr
1               5                   10                  15

Val Trp Leu Ser Val
            20

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Leu Ser Pro Thr Val Trp Leu Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Leu Ser Leu Leu Val Pro Val Phe
1               5
```

TRANSGENIC MICE HAVING A HUMAN MAJOR HISTOCOMPATIBILITY COMPLEX (MHC) PHENOTYPE, EXPERIMENTAL USES AND APPLICATIONS

CROSS-REFERENCE TO RELATED APPLICATIONS

This application is a continuation of application Ser. No. 10/566,386, filed Oct. 17, 2006, now abandoned, which is a U.S. National Stage Entry of PCT/IB2004/002374, filed Jul. 5, 2004, which claims the benefit of U.S. Provisional Application No. 60/490,945, filed Jul. 30, 2003, the entire disclosure of which is relied upon and incorporated by reference herein for all purposes.

BACKGROUND OF THE INVENTION

Many vaccines are currently being developed for human cancer immunotherapy and for treatment of infectious diseases, such as malaria, AIDS, hepatitis C virus, and SARS. Given the rapidity with which new emerging pathogens can appear, it is important to improve animal models that could be used to evaluate vaccination strategies and the protective capacity of different epitopes quickly and reliably. Furthermore, in vivo studies are already required to assess crucial variables of vaccine behavior that are not easily evaluated or impossible to measure in vitro, such as vaccine immunogenicity, vaccine formulation, route of administration, tissue distribution, and involvement of primary and secondary lymphoid organs. Because of their simplicity and flexibility, small animals, such as mice represent an attractive alternative to more cumbersome and expensive model systems, such as nonhuman primates, at least for initial vaccine development studies.

The moderate efficacy observed in several clinical trials of vaccines, which were found to be protective in wild-type animal studies (McMichael, A. J. & Hanke, T. *Nat Med* 9, 874-880 (2003)), may be partly explained by the different influence that human and animal MHC have on the outcome of the immune response, since animal MHC and human HLA molecules do not present the same optimal epitopes (Rotzschke, O. et al. *Nature* 348, 252-254 (1990)). Thus, despite some limitations, transgenic mice expressing human HLA should represent a useful improvement over wild-type mice as a preclinical model for testing vaccine candidates, evaluating the potential risk that the vaccines could induce autoimmune disorders, and devising better therapeutic strategies based on the human restriction element.

Cytotoxic T Cells

Cytotoxic T cells (CTL) play a crucial role in the eradication of infectious diseases and in some cases, cancer (P. Aichele, H. Hengartner, R. M. Zinkernagel and M. Schulz, J Exp Med 171 (1990), p. 1815; L. BenMohamed, H. Gras-Masse, A. Tartar, P. Daubersies, K Brahimi, M. Bossus, A. Thomas and P. Druhile, Eur J Immunol 27 (1997), p. 1242; D. J. Diamond, J. York, J. Sun, C. L. Wright and S. J. Forman, Blood 90 (1997), p. 1751). Recombinant protein vaccines do not reliably induce CTL responses (Habeshaw J A, Dalgleish A G, Bountiff L, Newell A L, Wilks, D, Walker L C, Manca F. 1990 November; 11(11): 418-25; Miller S B, Tse H, Rosenspire A J, King S R. Virology. 1992 December; 191 (2):9 73-7). The use of otherwise immunogenic vaccines consisting of attenuated pathogens in humans is hampered, in several important diseases, by overriding safety concerns. In the last few years, epitope-based approaches have been proposed as a possible strategy to develop novel prophylactic and immunotherapeutic vaccines (Melief C J, Offringa R, Toes R E, Kast W M. Curr Opin Immunol. 1996 October, 8(5):651-7; Chesnut R W, Design testing of peptide based cytotoxic T-cell mediated imrnunotherapeutic to treat infiction disease, cancer, in Ppowell, M F, Newman, M J (eds.): Vaccine Design: The Subunit, Adjuvant Approach, Plenum Press, New-York 1995, 847). This approach offers several advantages, including selection of naturally processed epitopes, which forces the immune system to focus on highly conserved and immunodominant epitopes of a pathogen (R. G. van der Most, A. Sette, C. Oseroff, J. Alexander, K. Murali-Krishna, L. L. Lau, S, Southwood, J. Sidney, R. W. Chesnut, M. Matioubian and R. Ahmed, J Immunol 157 (1996), p. 5543) and induction of multiepitopic responses to prevent escape by mutation such observed in HIV, hepatitis B virus (HBV) and hepatitis C virus (HCV) infections. It also allows the elimination of suppressive T cell determinants, which might preferably elicit a TH2 response, in conditions where a TH1 responses is desirable, or vice-versa (Pfeiffer C, Murray J, Madri J, Bottomly K. Immunol Rev. 1991 October; 123:65-84; P Chaturvedi, Q Yu, S Southwood, A Sette, and B Singh Int Immunol 1996 8: 745-755). It finally provides the possibility to get rid of autoimmune T cell determinants in antigens, which might induce undesirable autoimmune diseases. Protective antiviral or anti-tumoral immunity using CTL epitope-peptides has been achieved in several experimental models (D. J. Diamond, J. York, J. Sun, C. L. Wright and S. J. Forman, Blood 90 1997, p. 1751; J. E. J. Blaney, E. Nobusawa, M. A. Brehm, R. H. Bonneau, L. M. Mylin, T. M. Fu, Y. Kawaoka and S. S. Tevethia, J Virol 72 (1998), p. 9567).

CTL epitope definition based on the usage of human lymphocytes might be misleading due to environmental and genetic heterogeneity that lead to incomplete results, and due to technical difficulties in isolating CTL clones. HLA class I or class II transgenic mice described to date have proved to be a valuable tool to overcome these limitations as illustrated by the identification with such animal models of novel CTL and T helper epitopes (Hill A V. Annu Rev Immunol. 1998; 16:593-617; Carmon L, EI-Shami K M, Paz A., Pascolo S, Tzehoval E, Tirosb B, Koren R, Feldman M, Fridkin M, Lemonnier F A, Eisenbach L. Int J Cancer, 2000 Feb. 1; 85(3):391-7). These mice have also been used to demonstrate: i) good correlation between peptide HLA binding affinity and immunogenicity (Lustgarten J, Theobald M, Labadie C, LaFace D, Peterson P, Disis M L, Cheaver M A, Sherman L A. Hum Immunol. 1997 February; 52(2):109-18; Bakker A B, van der Burg S H, Huijbens R J, DRijfhout J W, Melief C J, Adema G J, Figdor C G. Int J Cancer. 1997 Jan. 27; 70(3):302-9), ii) significant overlap between the murine and human CTL system at the level of antigen processing (same epitopes generated), and iii) comparable mobilization against most antigens of the CTL repertoires in HLA transgenic mice and humans (Wentworth, P. A., A. Vifiello, J. Sidney, E. Keogh, P, W. Chesnut, H. Grey, A. Sette. 1996. Eur. J. Immunol. 26:97; Alexander, J., C. Oserof, J. Sidney, P. Wentworth, E. Keogh, G. Hermanson, F. V. Chisari R. T, Kubo, H. M, Grey, A, Sette, 1997. J. Immunol. 159:4753).

To date, synthetic peptide-based CTL epitope vaccines have been developed as immunotherapeutics against a number of human diseases [18-20]. However, only moderate efficacy was observed in several clinical trials (21). This may be partly explained by the failure of these vaccines to induce sufficiently strong CTL responses. Indeed, recent reports suggest the need for CD4+ T-cell help to obtain maximum CTL response (A. J. Zajac, K. Murali-Krishna, J. N. Blattman and R. Ahmed, Curr Opin Immunol 10 (1998), p. 444; Firat H, Garcia-Pons F, Tourdot S, Pascolo S, Scardino A, Garcia Z, Michel M L, Jack R W, Jung O, Kosmatopoulos K, Mateo L, Suhrbier A, Lemonnier F A, Langlade-Dernoyen P Eur J Irmnunol 29, 3112, 1999).

CTL are critical components of protective immunity against viral infections, but the requirements for in vivo priming of CTL are not completely understood. It is now accepted that Th cells are usually essential for CTL priming with synthetic peptides. With respect to synthetic CTL epitopic peptides, several studies point to a mandatory need for Th lymphocyte stimulation to induce optimal CTL responses (C. Fayolle, E. Deriaud and C. Leclerc, J Immunol 147 (1991), p, 4069; C. Widmann, P. Romero, J. L. Maryanski, G. Corradin and D. Valmori, J Immunol Meth 155 (1992), p. 95; M. Shirai, C. D. Pendkton, J. Ahlers, T. Takeshita, M. Newman and J. A. Berzofsky, J Immunol 152 (1994), p. 549; J. P. Sauet, H. Gras-Masse, J. G. Guillet and E. Gomard, Int Immunol 8 (1996). p. 457). Several of these studies showed that activation of a CD8+ T cell requires simultaneous interaction of a CD4+ T helper cell and a CD8+ T cell with the same antigen-presenting cell presenting their cognate epitopes (Ridge J P, Di Rosa F, Matzinger P. Nature. 1998 Jun. 4; 3 93 (6684):474-8). The relevance of this three-cell interaction for priming of CTLs is confirmed by studies with viral epitopes, and animal models, since in vivo induction of CTLs was most efficient when CTL and Th epitopes were physically linked rather than administered as an unlinked mixture (Shirai M, Pendleton C D, Ahlers J, Takeshita T, Newman M, Berzohky J A. J Immunol. 1994 Jan. 15; 152(2): 549-56; Oseroff C, Sette A, Wentworth P, Celis E, Maewal A, Dahlberg C, Fikes J, Kubo R T, Chesnut R W, Grey B X Alexander J. Vaccine. 1998 May; 16(8): 823-33). The capacity of CTL and Th antigenic peptides to efficiently induce CTL responses has been demonstrated both in experimental models (C. Fayolle, E. Deriaud and C. Leclerc, J Immunol 147 (1991), p, 4069; C. Widmann, P. Romero, J. L. Maryanski, G. Corradin and D. Valmori, J Immunol Meth 155 (1992), p. 95) and in humans (A. Vitiello, G. Ishioka, H. M. Grey, R. Rose, P. Famess, R. LaFond, L. Yuan, F. V. Chisari, J. Furze and R. Bartholomeuz, J Clin Invest 95 (1995), p. 341; B. Livingston, C. Crimi, H. Grey, G. Ishioka, F. V. Chisari, J. Fikes, H. M. Grey, R. Chesnut and A. Sette, J Immunol 159 (1997), p. 1383). Moreover, a potent Th response plays an important role not only for optimal induction of CTL responses, but also for maintenance of CTL memory (E. A. Walter, P. D. Greenberg, M. J. Gilbert, R. J. Finch, K-S. Watanabe, E. D. Tbomas and S. R. Riddell, N Engl J Med 333 (1995), p. 1038; Riddell S R, Greenberg P D, In Thomas E D, Blume K G, Forman S J (eds): Hematopoietic Cell Transplantation, 2nd edn. Malden, Mass.: Blackwell Science Inc., 1999). Finally, it has long been documented that CD4+ T "helper" cells are crucial in coordinating cellular and humoral immune responses against exogenous antigens.

Recently, a transgenic (Tg) mouse that expresses both HLA-A*0201 class I and HLA-DR1 class II molecules was established (BenMohamed L, Krishnan R, Longmate J, Auge C, Low L, Primus J, Diamond D J, Hum, Immunol. 2000 August; 61(8):764-79). The authors reported that both HLA-A*0201 and HLA-DR1 transgenes are functional in vivo, that both MHC class I and class II molecules were utilized as restriction elements, and that the product of the HLA-DR1 transgene enhances the HLA-A*0201-restricted antigen-specific CTL responses (BenMohamed L, Krishnan R, Longmate J, Auge C, Low L, Primus J, Diamond D J, Hum, Immunol. 2000 August; 61(8):764-79).

It is noteworthy that these HLA-A*0201/DR1 Tg mice expressed their own MHC H-2 class I and class II molecules. Because HLA class I transgenic mice expressing endogenous mouse MHC class I genes preferentially and often exclusively develop H-2 restricted CTL response (C Barra, H Gournier, Z Garcia, P N Marche, E Jouvin-Marche, P Briand, P Fillipi, and F A Lemonnier J Immunol 1993 150: 3681-3689; Epstein H, Hardy F., May J S, Johnson M H, Holmes N. Eur J Immunol. 1989 September; 19(9):1575-83; Le A X; E J Bernhard, M J Holterman, S Strub, P Parham, E Lacy, and V H Engelhard J Immunol 1989 142: 13 66-1371; Vitiello A, Marchesini D, Furze J, Sherman L A, Chesnut R W., J Exp Med. 1991 Apr. 1; 173(4):100715), and HLA class II transgenic mice expressing endogenous mouse MHC class II genes fail to induce reliable HLA class II restricted antigen-specific responses (Nishimura Y, Iwanaga T, Inamitsu T, Yanagawa Y, Yasunami M, Kimura A, Hirokawa K, Sasazuki T., J Immunol 1990 Jul. 1; 145(1):353-60), these HLA-A*0201/DR1 Tg mice are of limited utility to assess human-specific responses to antigen.

However, in HLA class I transgenic H-2 class I knock-out mice, or HLA class II transgenic H-2 class II knock-out mice, only HLA-restricted CTL immune responses occur (Pascolo S, Bervas N, Ure J M, Smith A G, Lemonnier F A, Perarnau, B., J Exp Med. 1997 Jun. 16; 185(12). 2043-51; Madsen L, Labrecque N, Engberg J, Dierich A, Svejgaard A, Benoist C, Mathis D, Fugger L., Proc Natl Acad Sci USA— 1999 Aug. 31; 96(18):10338-43). In fact, HLA-A2.1-transgenic H-2 class I-knock-out (KO) mice exhibit the ability to mount enhanced HLA-A2.1-restricted responses as compared to HLA-A2.1-transgenic mice that still express the endogenous murine H-2 class I molecules (Pascolo, S. et al. *J Exp Med* 185, 2043-2051 (1997); Ureta-Vidal, A., Firat, H., Perarnau, B. & Lemonnier, F. A. *J Immunol* 163, 2555-2560 (1999); Firat, H. et al., *Int Immunol* 14, 925-934 (2002); Rohrlich, P. S. et al., *Int Immunol* 15, 765-772 (2003)). The inventors have made similar observations with HLA-DR1-transgenic mice, depending on whether or not they are deficient in H-2 class II molecules (A. Pajot, unpublished results). Furthermore, in the absence of competition from murine MHC molecules, the HLA-A2.1-transgenic H-2 class I-KO or HLA-DRI-transgenic H-2 class II-KO mice generate only HLA-restricted immune responses (Pascolo, S. et al. *J Exp Med* 185, 2043-2051 (1997)) (A. Pajot, unpublished results), facilitating the monitoring of HLA-restricted CD8+ and CD4+ T cell responses. However, protective immune responses against pathogens, which often require collaboration between T helper and cytotoxic CD8+ T cells, cannot be studied in the single HLA class I- or HLA class II-transgenic mice, which do not allow the simultaneous assessment of HLA class I and II human responses in the same mouse.

Accordingly, there exists a need in the art for a convenient animal model system to test the immunogenicity of human vaccine candidates comprising constructs containing human CTL epitopes and, in some cases, with the inclusion of high potency CD4+ Th (helper T lymphocyte) epitopes to sustain antiviral and antitumoral CD8+ T-cell activity (A. J. Zajac, K. Murali-Krishna, J. N. Blattman and R. Ahmed, Curr Opin Immunol 10 (1998), p. 444; Firat H, Garcia-Pons F, Tourdot S, Pascolo S, Scardino A, Garcia Z, Michel M L, Jack R W, Jung O, Kosmatopoulos K, Mateo L, Suhrbier A, Lemonnier F A, Langlade-Dernoyen P, Eur J Irmnunol 29, 3112, 1999). There is also a need for a system that allows the simultaneous assessment of the mutual coordination between a CTL response, a TH response (in particular s TH$_1$ or TH$_2$ response), and, optionally, a humoral response.

SUMMARY OF THE INVENTION

The inventors have met this need and more by providing mice transgenic for both HLA-A2.1 and HLA-DR1 molecules, in a background that is deficient for both H-2 class I and class II molecules. Specifically, the invention provides mice comprising (1) mutated H-2 class I and class II molecules; and (2) expressing HLA class I transgenic molecules, or HLA class II transgenic molecules, or HLA class I transgenic molecules and HLA class II transgenic molecules. These mice provide a model useful in the development and optimization of vaccine constructs with maximum in vivo immunogenicity for human use. Specifically, such mice enable a complete analysis of the three components of the immune adaptive response (antibody, helper and cytolytic) in a single animal, as well as an evaluation of the protection specifically conferred by vaccination against an antigenic challenge.

Mice of the invention, which comprise a knock-out for both H-2 class I and class II molecules, and express HLA class I transgenic molecules and HLA class II transgenic molecules represent a completely humanized experimental mouse that can be used to simultaneously detect the presence of antigen-specific antibodies, an antigen-specific HLA-DRI restricted T cell response, and an antigen-specific HLA-A2 restricted T cell response. These mice will be useful to study how mutual coordination operates between a CTL response, a TH response (in particular a TH$_1$ or TH$_2$ response), and, optionally, a humoral response. These mice represent an optimized tool for basic and applied vaccinology studies.

A first embodiment of the invention provides a transgenic mouse comprising a disrupted H2 class I gene, a disrupted H2 class II gene, and a functional HLA class I or class II transgene.

A second embodiment of the invention provides a transgenic mouse comprising a disrupted H2 class I gene, a disrupted H2 class II gene, a functional HLA class I transgene, and a functional HLA class II transgene.

In some embodiments, the HLA class I transgene is an HLA-A2 transgene and the HLA class II transgene is an HLA-DR1 transgene. In other embodiments, the HLA-A2 transgene comprises the HLA-A2 sequence provided in the sequence listing and the HLA-DR1 transgene comprises the HLA-DR1 sequence provided in the sequence listing.

A further embodiment of the invention provides a transgenic mouse deficient for both H2 class I and class II molecules, wherein the transgenic mouse comprises a functional HLA class I transgene and a functional HLA class II transgene. In an embodiment, the mouse has the genotype HLA-A2$^+$HLA-DR1$^+$β2m°IAβ°. In some embodiments the HLA-A2 transgene comprises the HLA-A2 sequence provided in the sequence listing and the HLA-DR1 transgene comprises the HLA-DR1 sequence provided in the sequence listing.

Another embodiment of the invention provides a method of simultaneously identifying the presence of one or more epitopes in a candidate antigen or group of antigens, where the one or more epitopes elicits a specific humoral response, a TH HLA-DR1 restricted response, and/or a CTRL HLA-A2 restricted response. The method comprises administering the candidate antigen or group of candidate antigens to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$HLA-DR1$^+$β2m°IAβ°; assaying for a specific humoral response in the mouse to the antigen; assaying for a TH HLA-DR1 restricted response in the mouse to the antigen; and assaying for a CTRL HLA-A2 restricted response in the mouse to the antigen. Observation of a specific humoral response in the mouse to the antigen identifies an epitope that elicits a humoral response in the antigen. Observation of a TH HLA-DR1 restricted response in the mouse to the antigen identifies an epitope that elicits a TH HLA-DR1 restricted response in the antigen. Observation of a CTRL HLA-A2 restricted response in the mouse to the antigen identifies an epitope which elicits a CTRL HLA-A2 restricted response in the antigen.

In some embodiments, the method includes assaying for a Th1-specific response in the mouse to the antigen and assaying for a Th2-specific response in the mouse to the antigen. In this case, observation of a Th1-specific response in the mouse to the antigen identifies an epitope that elicits a Th1-specific response in the mouse to the antigen, and observation of a Th2-specific response in the mouse to the antigen identifies an epitope that elicits a Th2-specific response in the mouse to the antigen.

This invention also provides a method of identifying the presence of an HLA DR1-restricted T helper epitope in a candidate antigen or group of candidate antigens, the method comprising administering the candidate antigen or group of candidate antigens to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$HLA-DR1$^+$β2m°IAβ°; and assaying for a TH HLA-DR1 restricted T helper epitope response in the mouse to the antigen. Observation of a TH HLA-DR1 restricted T helper epitope response in the mouse to the antigen identifies an epitope that elicits a TH HLA-DR1 restricted T helper epitope response in the antigen.

In addition, this invention provides an isolated antigen comprising an HLA DR1-restricted T helper epitope identified by the method of the preceding paragraph. In some embodiments, the isolated antigen further includes an epitope that elicits a humoral response and/or an epitope that elicits a CTRL HLA-A2 restricted response. In some embodiments, the antigen comprising an HLA DR1-restricted T helper epitope comprises a polypeptide. In other embodiments, the antigen comprising an HLA DR1-restricted T helper epitope comprises a polynucleotide. In further embodiments, the antigen comprising an HLA DR1-restricted T helper epitope comprises DNA, RNA, or DNA and RNA.

Further, this invention provides a method of identifying the presence of an HLA-A2-restricted T cytotoxic (CTL) epitope in a candidate antigen or group of candidate antigens, the method comprising administering the candidate antigen or group of candidate antigens to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2⁺HLA-DR1⁺β2m°IAβ°; and assaying for an HLA-A2-restricted T cytotoxic (CTL) response in the mouse to the antigen or group of antigens. Observation of an HLA-A2-restricted T cytotoxic (CTL) response in the mouse to the antigen or group of antigens identifies an epitope that elicits a an HLA-A2-restricted T cytotoxic (CTL) response in the antigen or group of antigens.

This invention provides an isolated antigen comprising an HLA-A2-restricted T cytotoxic (CTL) epitope identified by the method of the preceding paragraph. In some embodiments, the antigen further comprises an epitope that elicits a humoral response and/or an epitope that elicits a TH HLA-DR1 restricted T helper epitope response. In some embodiments, the antigen comprising an HLA-A2-restricted T cytotoxic (CTL) epitope comprises a polypeptide. In other embodiments, the antigen comprising an HLA-A2-restricted T cytotoxic (CTL) epitope comprises a polynucleotide. In further embodiments, the antigen comprising an HLA-A2-restricted T cytotoxic (CTL) epitope comprises, DNA, RNA, or DNA and RNA.

This invention also provides a method of comparing the efficiency of the T-helper cell response induced by two or more vaccines. This method comprises administering a first candidate vaccine to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2⁺HLA-DR1⁺β2m°IAβ°, and measuring the T-helper cell response induced in the mouse by the first candidate vaccine; administering a second candidate vaccine to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2⁺HLA-DR1⁺β2m°IAβ°, and measuring the T-helper cell response induced in the mouse by the second candidate vaccine; administering each additional candidate vaccine to be compared to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2⁺HLA-DR1⁺β2m°IAβ°, and measuring the T-helper cell response induced in the mouse by the additional candidate vaccine, and determining the efficiency of each candidate vaccine to induce a T-helper cell response by comparing the T-helper cell responses to each of the vaccines to be compared with each other. In some embodiments the T-helper cell response is an HLA-DR1 restricted response.

In addition, this invention provides a method of comparing the efficiency of T cytotoxic cell responses induced by two or more vaccines. The method includes administering a first candidate vaccine to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2⁺HLA-DR1⁺β2m°IAβ°, and measuring the T cytotoxic cell response induced in the mouse by the first candidate vaccine; administering a second candidate vaccine to a mouse of a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2⁺HLA-DR1⁺β2m°IAβ°, and measuring the T cytotoxic cell response induced in the mouse by the second candidate vaccine; administering each additional candidate vaccine to be compared to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2⁺HLA-DR1⁺β2m°IAβ°, and measuring the T cytotoxic cell response induced in the mouse by the additional candidate vaccine; and determining the efficiency of each candidate vaccine to induce a T cytotoxic cell response by comparing the T cytotoxic cell responses to each of the vaccines to be compared with each other. In some embodiments the T cytotoxic cell response is an HLA-A2 restricted response.

Further, this invention provides a method of simultaneously comparing the efficiency of T-helper cell response and T cytotoxic cell response induced by two or more vaccines. The method comprises administering a first candidate vaccine to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2⁺HLA-DR1⁺β2m°IAβ°, and measuring the T-helper cell response and T cytotoxic cell response induced in the mouse by the first candidate vaccine; administering a second candidate vaccine to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2⁺HLA-DR1⁺β2m°IAβ°, and measuring the T-helper cell response and T cytotoxic cell response induced in the mouse by the second candidate vaccine; administering each additional candidate vaccine to be compared to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2⁺HLA-DR1⁺β2m°IAβ°, and measuring the T-helper cell response and T cytotoxic cell response induced in the mouse by each additional candidate vaccine; and determining the efficiency of each candidate vaccine to induce a T-helper cell response and T cytotoxic cell response by comparing the T-helper cell response and T cytotoxic cell response to each of the vaccines to be compared with each other. In some embodiments the T-helper cell response is an HLA-DR1 restricted response, and the T cytotoxic cell response is an HLA-A2 restricted response.

This invention also provides a method of simultaneously determining the humoral response, the T-helper cell response, and the T cytotoxic cell response of a mouse following its immunization with an antigen or a vaccine comprising one or more antigens. The method comprises administering the antigen or the vaccine comprising one or more antigens to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$HLA-DR1$^+$ $\beta$2m°IA$\beta$°, and assaying for a specific humoral response in the mouse to the antigen or vaccine comprising one or more antigens, assaying for a T-helper cell response in the mouse to the antigen or vaccine comprising one or more antigens, and assaying for a T cytotoxic cell response in the mouse to the antigen or vaccine comprising one or more antigens. In some embodiments the T-helper cell response is a TH HLA-DR1 restricted response. In some embodiments the T cytotoxic cell response is a CTRL HLA-A2 restricted response.

This invention also provides a method of optimizing two or more candidate vaccine compositions for administration to a human, based on preselected criteria. The method includes simultaneously determining the humoral response, the T-helper cell response, and the T cytotoxic cell response of a mouse following its immunization with the two or more candidate vaccine compositions, using a method comprising administering the antigen or the vaccine comprising one or more antigens to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$HLA-DR1$^+$ $\beta$2m°IA$\beta$°, assaying for a specific humoral response in the mouse to the antigen or vaccine comprising one or more antigens, assaying for a T-helper cell response in the mouse to the antigen or vaccine comprising one or more antigens, assaying for a T cytotoxic cell response in the mouse to the antigen or vaccine comprising one or more antigens, and selecting an optimized vaccine by applying preselected criteria to the results. In some embodiments, the two or more vaccine candidates differ only in the ratio of antigen to adjuvant present in the vaccine. In some embodiments, the two or more vaccine candidates differ only in the type of adjuvant present in the vaccine.

In another aspect, the invention provides a method of determining whether a vaccine poses a risk of induction of an autoimmune disease when administered to a human. The method comprises administering the vaccine to a transgenic mouse comprising a disrupted H2 class I gene, a disrupted H2 class II gene, a functional HLA-A2 transgene, and a functional HLA-DR1 transgene, or a transgenic mouse deficient for both H2 class I and class II molecules, wherein the transgenic mouse comprises a functional HLA class I transgene and a functional HLA class II transgene, and has the genotype HLA-A2$^+$HLA-DR1$^+$$\beta$2m°IA$\beta$°, and assaying for an autoimmune response in the mouse, where observation of an autoimmune response in the mouse indicates that the vaccine poses a risk of induction of an autoimmune disease when administered to a human.

This invention also provides an isolated transgenic mouse cell comprising a disrupted H2 class I gene, a disrupted H2 class II gene, and a functional HLA class I or class II transgene.

In addition, the invention provides an isolated transgenic mouse cell comprising a disrupted H2 class I gene, a disrupted H2 class II gene, a functional HLA class I transgene, and a functional HLA class II transgene.

In some embodiments, the HLA class I transgene is an HLA-A2 transgene and the HLA class II transgene is an HLA-DR1 transgene. In other embodiments, the HLA-A2 transgene comprises the HLA-A2 sequence provided in the sequence listing and the HLA-DR1 transgene comprises the HLA-DR1 sequence provided in the sequence listing.

Further, this invention provides an isolated transgenic mouse cell deficient for both H2 class I and class II molecules, wherein the transgenic mouse cell comprises a functional HLA class I transgene and a functional HLA class II transgene. In some embodiments, the transgenic mouse cell has the genotype HLA-A2$^+$HLA-DR1$^+$$\beta$2m°IA$\beta$°. In other embodiments, the HLA-A2 transgene comprises the HLA-A2 sequence provided in the sequence listing and the HLA-DR1 transgene comprises the HLA-DR1 sequence provided in the sequence listing.

BRIEF DESCRIPTION OF THE DRAWINGS

The invention will be more fully described with reference to the drawings in which:

(FIG. 1A) Splenocytes from HLA-DR1-transgenic H-2 class II-KO (DR1$^+$ CII$^-$, left panel), HLA-A2.1-/HLA-DR1-transgenic H-2 class I-/class II-KO (A2$^+$ DR1$^+$ CI$^-$ CII$^-$, central panel), and HLA-A2.1-transgenic H-2 class I-KO (A2$^+$ CI$^-$, right panel) mice were stained with either FITC-labeled W6/32 (anti-HLA-ABC, in abcissas) or biotinylated 28-8-6S (anti-H-2K$^b$/D$^b$, in ordinates) m.Ab, the latter revealed with PE-labeled anti-mouse IgG. (FIG. 1B) B220+ splenic B lymphocytes from the same strains of mice, were stained with FITC-labeled L243 (anti-HLA-DR1, upper panels) and PE-labeled AF6-120.1 (anti-H-2 IA$\beta^b$, lower panels) m.Ab.

(FIG. 2A) Splenocytes from HLA-DR1-transgenic H-2 class II-KO (DR1$^+$ CII$^-$, left panel), HLA-A2.1-/HLA-DR1-transgenic H-2 class I-/class II-KO (A2$^+$ DR1$^+$ CI$^-$ CII$^-$, central panel), and HLA-A2.1-transgenic H-2 class I-KO (A2$^+$ CI$^-$, right panel) mice were stained with PE-labeled CT-CD4 (anti-mouse CD4, in ordinates) and FITC-labeled 53-6.7 (anti-mouse CD8, in abcissas) m.Ab. Numbers correspond to percentages of CD4$^+$ (upper left square) or CD8$^+$ (lower right square) T cells in total splenocytes. (FIGS. 2B and 2C) Immunoscope RT-PCR analysis of purified splenic CD8$^+$ (b) and CD4$^+$ (c) T cells for BV segment family (1-20) usage using forward BV family (1-20) specific and reverse BC primers. A typical profile for a BV segment family productively rearranged includes a series of peaks with a Gaussian-like distribution differing in length by 3 nucleotides. The Figure illustrates the results obtained with a HLA-A2.1-/HLA-DR1-transgenic H-2 class I-/class II-KO representative mouse.

(FIG. 3A) Humoral (upper panel), cytolytic (middle panel) and proliferative (lower panel) responses and specificity controls of a representative HBsAg-DNA-immunized mouse. The antibody (IgG) titer against HBsAg particles containing both middle and small HBV envelope proteins and against the preS2$_{109\text{-}134}$ peptide were determined in an ELISA assay. Cytolytic activity at different effector/target (E/T) ratios was assessed using RMAS-HHD target cells pulsed with either relevant (HBsAg$_{348\text{-}357}$, HLA-A2.1-restricted ♦) or control (HBsAg$_{371\text{-}378}$, H-2 K$^b$-restricted ∆, and MAGE-3$_{271\text{-}279}$, HLA-A2.1-restricted [ ]) peptide. Proliferative responses were detected using either relevant (HBsAg$_{180\text{-}195}$, HLA-DR1-restricted) or control (HBsAg$_{126\text{-}138}$, H-2 IA$^b$-restricted and HIV 1 Gag$_{263\text{-}278}$, HLA-DR1-restricted) peptide. (FIG. 3B) Similar evaluation of the antibody (IgG, upper panel), cytolytic (middle panel) and proliferative (lower panel) responses of 6 (1-6) HBsAg-DNA-immunized mice as compared to mean responses of 6 naive mice (0). Cytolytic activity at a 30/1 E/T ratio was assessed on RMAS-HHD target cells pulsed with either HBsAg$_{348\text{-}357}$, immunodominant (filled bars) or HBsAg$_{335\text{-}343}$, subdominant (grey bars) peptide.

FIG. 6 shows the T CD4 proliferative response to HLA-DR1 restricted epitopes following immunization of HLA-A2+DR1+CI−CII− mice with pcmv S2-S.

SEQUENCES

Figure 1A:
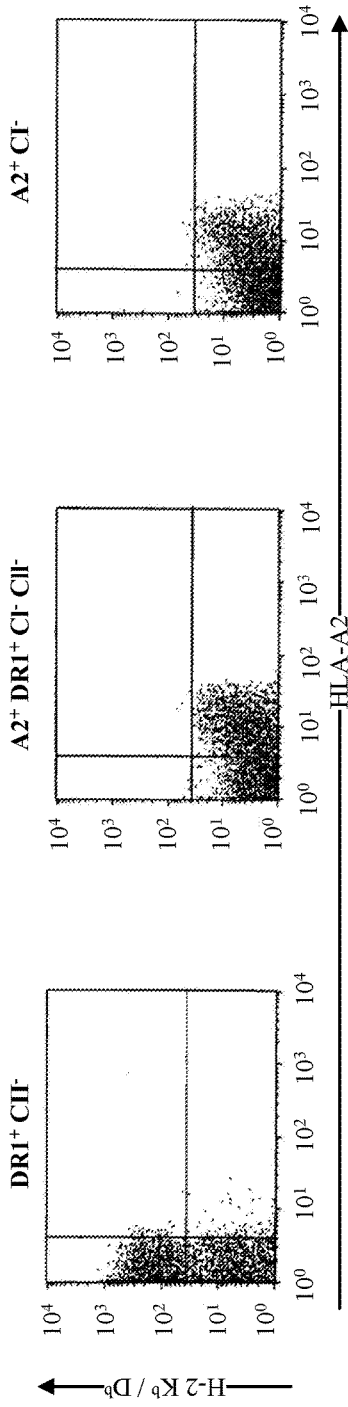
FIGS. 1A and 1B show a flow cytometric analysis of the cell-surface expression of the indicated transgenic molecules.

SEQ ID NO:1 contains the following subparts: Nucleotides 1-1205 comprise the HLA-A2 promoter; nucleotides 1206-1265 the HLA-A2 leader sequence; nucleotides 1266-1565 the human β2 microgobulin cDNA; nucleotides 1566-1610 a (Gly4Ser)$_3$ linker; nucleotides 1611-2440 a segment containing exon 2 and part of intron 3 of HLA-A2; and nucleotides 2441-4547 a segment containing part of intron 3, exons 4 to 8, and part of the 3' non-coding region of the H$_2$D$^b$ gene.

SEQ ID NO:2 is the nucleotide sequence of the DRA*0101 gene. Nucleotides 1-15279 are the promoter located 5' to the HLA-DR alpha gene, nucleotides 15280-15425 are exon 1, nucleotides 15344-15346 are the ATG start codon, nucleotides 17838-18083 are exon 2, nucleotides 18575-18866 are exon 3, nucleotides 19146-19311 are exon 4, and nucleotides 20008-20340 are exon 5.

SEQ ID NO:3 is the nucleotide sequence of the DRB1*010101 gene. Nucleotides 7391-7552 are exon 1, nucleotides 7453-7455 are the ATG start codon, nucleotides 15809-16079 are exon 2, nucleotides 19536-19817 are exon 3, nucleotides 20515-20624 are exon 4, nucleotides 21097-21121 are exon 5, and nucleotides 21750-22085 are exon 6.

DETAILED DESCRIPTION OF THE INVENTION

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

This invention provides mice comprising (1) mutated H-2 class I and class II molecules; and (2) expressing HLA class I transgenic molecules, or HLA class II transgenic molecules, or HLA class I transgenic molecules and HLA class II transgenic molecules. Mice of the invention, which comprise a knock-out for both H-2 class I and class II molecules, and express HLA class I transgenic molecules and HLA class II transgenic molecules represent a completely humanized experimental mouse that can be used to simultaneously detect the presence of antigen-specific antibodies, an antigen-specific HLA-DRI restricted T cell response, and an antigen-specific HLA-A2 restricted T cell response. These mice are useful to study how mutual coordination operates between a CTL response, a TH response (in particular a TH$_1$ or TH$_2$ response), and, optionally, a humoral response. These mice represent an optimized tool for basic and applied vaccinology studies.

The invention provides transgenic mouse comprising a disrupted H2 class I gene, a disrupted H2 class II gene, and a functional HLA class I or class II transgene. In some embodiments, the transgenic mouse comprises a disrupted H2 class I gene, a disrupted H2 class II gene, a functional HLA class I transgene, and a functional HLA class II transgene. Such a mouse can be said to be a completely humanized experimental mouse, because it can be used to simultaneously detect the presence of antigen-specific antibodies, an antigen-specific HLA-DRI restricted T cell response, and an antigen-specific HLA-A2 restricted T cell response.

As shown, in part, in the Examples provided herein, and as is generally clear to one of skill in the art from the disclosure, HLA-A2.1-/HLA-DR1-transgenic H-2 class I-/class II-KO mice have the capacity to develop HBsAg-specific antibody, CD4+ helper and CD8+ cytolytic T cell responses following DNA immunization. These responses, observed in every single mouse tested, were directed at the same immunodominant epitopes as human responses and conferred to the immunized animals specific protection against a HBsAg recombinant vaccinia virus.

T helper cells are essential for full maturation of antibody responses (Katz, D. H. & Benacerraf, B., *Adv Immunol* 15, 1-94 (1972)) CTL priming against many epitopes (von Boehmer, H. & Haas, W., *J Exp Med* 150, 1134-1142 (1979); Keene, J. A. & Forman, J., *J Exp Med* 155, 768-782 (1982)) and CTL long-term maintenance (Matloubian, M., Concepcion, R. J. & Ahmed, R., *J Virol* 68, 8056-8063 (1994)). Both antibodies (Lefrancois, L., *J Virol* 51, 208-214 (1984)) and CTL (Zinkernagel, R. M. & Welsh, R. M., *J Immunol* 117, 1495-1502 (1976)) are critical components of protective immunity against viral infections. Potent HBsAg-specific antibody and CTL responses were in fact observed in HLA-A2.1-/HLA-DR1-double transgenic, H-2 class I-/class II-KO mice, but not in HLA-A2.1-single transgenic, H-2 class I-/class II-KO mice. Thus, HBsAg-specific CD4+ T cell help is essential for generating efficient HBsAg-specific CTL and antibody responses. These results are consistent with studies on HBsAg-immunized mice (Milich, D. R., *Semin Liver Dis* 11, 93-112 (1991)) and HBsAg-vaccinated humans (Celis, E., Kung, P. C. & Chang, T. W., J Immunol 132, 1511-1516 (1984)), which suggest that production of an anti-HBs antibody response is dependent on CD4+ T cells.

Transgenic mice expressing both HLA-A2.1 class I and HLA-DR1 class II molecules have already been derived (BenMohamed, L. et al. *Hum Immunol* 61, 764-779 (2000)). The authors reported that both the HLA-A2.I and HLA-DR1 molecules are functional restriction elements in vivo and that the product of the HLA-DR1 transgene enhances the HLA-A2.1-restricted antigen-specific CTL responses. However, the human relevance of the immune responses in these mice is dwarfed by the fact that they still expressed their own H-2 class I and class II molecules, which are usually preferentially and often exclusively used as restricting elements in response to antigens (Ureta-Vidal, A., Firat, H., Perarnau, B. & Lemonnier, F. A., *J Immunol* 163, 2555-2560 (1999); Rohrlich, P. S. et al., *Int Immunol* 15, 765-772 (2003)) (A. Pajot, unpublished results). The invention described herein overcomes this limitation by providing HLA-A2.1/HLA-DR1-transgenic, H-2 class I-/class II-KO mice.

In some embodiments the HLA-A2.1-/HLA-DR1-transgenic, H-2 class I-/class II-KO mice express, in a β2m-KO context, a HLA-A2.1 monochain in which the human β2m is covalently linked by a peptidic arm to the HLA-A2.1 heavy chain. They further lack cell surface expression of conventional H-2 IA and IE class II molecules as a result of the inactivation of the H-2 IAβ$^b$ gene, since H-2 IEα is a pseudogene in the H-2$^b$ haplotype. The results provided herein demonstrate that such mice are deprived of cell surface expression of H-2 class I and class II molecules. However, it was reported in one case that a free class I heavy chain, in particular H-2 D$^b$, may exist on the surface of a β2m-KO mouse, and could induce an alloreactivity response. Even if this is so, because such mice are empty of peptide, they should not interfere in antigen-specific immune response (Bix, M. & Raulet, D., *J Exp Med* 176, 829-834 (1992)). This is supported by the report of Allen et al (Allen, H., Fraser, J., Flyer, D., Calvin, S. & Flavell, R., *Proc Natl Acad Sci USA* 83, 7447-7451 (1986)), in which they confirmed that H-2 D$^b$ is expressed at the cell surface even when there is no β2m present within the cell, but that such D$^b$ antigen is recognized by neither D$^b$-allospecific or D$^b$-restricted cytotoxic T lymphocytes. Furthermore, D$^b$ antigens are not recognized by most monoclonal antibodies of the native D$^b$.

Nonetheless, in HLA-DRα single transgenic mice, it was reported that unconventional HLA-DRα/H-2 IEβ$^b$ hybrid complexes may be expressed to some extent on the cell surface, at least in the absence of the HLA-DRβ chain (Lawrance, S. K. et al., *Cell* 58, 583-594 (1989)). In spite of this observation, these unconventional molecules were not detected serologically on cell surfaces in HLA-A2.1-/HLA-DR1-transgenic, H-2 class I-/class II-KO mice, even with mAb (17-3-3S), which is known to react with such hybrid molecules (Ozato, K., Mayer, N. & Sachs, D. H., *J Immunol* 124, 533-540 (1980)) (FIG. 1a and data not shown). In addition, the results obtained on studying HBsAg-specific and HIV 1-Gag-specific T cell responses of these mice were all indicative of exclusive usage of the HLA-A2.1 and HLA-DR1 molecules as restricting elements. This argues that the unconventional HLA-DRα/H-2 IEβ$^b$ hybrids were likely unstable compared to conventional HLA-DRα/HLA-DRβ molecules and that they may exist only in the absence of the HLA-DRβ chain. Mouse strains in which the entire (H-2 IAβ$^b$, IAα$^b$, IEβ$^b$) H-2 class II region has been deleted (Madsen, L. et al., *Proc Natl Acad Sci USA* 96, 10338-10343 (1999)), as well as the H-2 D$^b$ gene, are being analyzed to completely exclude this possibility. Preliminary analysis of splenocytes obtained from the first animals revealed a CD4+ T cell pool restoration similar to that observed in HLA-DR1-transgenic H-2 class II-KO (IAβ$^{b\circ}$) mice, suggesting that the HLA-DR1-restricted CD4+ T cell responses of these new mice should be equivalent to those of the HLA-A2.1-/HLA-DR1-transgenic, H-2 class I-/class II-KO mice.

The peripheral CD8+ T lymphocytes of HLA-A2.1-/HLA-DR1-transgenic, H-2 class I-/class II-KO mice, compared to parental HLA-A2.1-transgenic H-2 class I-KO mice, are quantitatively and qualitatively similar with full diversification, at least in terms of BV segment usage, of the TCR repertoire. Partial restoration compared to wild-type animals, especially of the CD8+ T cell pool, has been a constant observation in single HLA-transgenic mice expressing a chimeric (α3 domain of mouse origin) HLA-A2.1 molecule (Pascolo, S. et al., *J Exp Med* 185, 2043-2051 (1997)). Regardless of the α3 domain substitution, the interaction remains suboptimal between mouse CD8 and HLA-A2.1 molecules, since co-crystal analysis has documented that human CD8 also contacts the HLA-A2.1 heavy chain α2 domain (Gao, G. F. et al., *Nature* 387, 630-634 (1997)). Suboptimal cooperation might also occur in the endoplasmic reticulum where many molecules (TAP, tapasine, ERp 57) assist MHC class I molecule biosynthesis. However, at this stage, the only documented functional difference between these mice and human endoplasmic reticulum molecules, namely the efficient transport by human but not mouse TAP of COOH-terminus positively charged cytosolic peptides (Momburg, F., Neefjes, J. J. & Hammerling, G. J., *Curr Opin Immunol* 6, 32-37 (1994)), is not relevant for HLA-A2.1 molecules which bind peptides with a hydrophobic C-terminus, since these peptides are transported efficiently by mouse and human TAP. Even though the number of CD8+ T lymphocytes is lower in both single HLA-A2.1-transgenic, H-2 class I-KO mice and in HLA-A2.1-/HLA-DR1-transgenic H-2 class I-/class II-KO mice, they respond efficiently against HBsAg and, importantly, the latter mice develop antibody, helper and cytolytic cell responses similar to humans.

One of the difficulties hampering the design of T-epitope-based vaccines targeting T lymphocytes is HLA class I/class II molecule polymorphism. HLA-A2.1 and HLA-DR1 molecules are expressed by a significant proportion of individuals in human populations (30 to 50% for HLA-A2.1, 6 to 18% for HLA-DR1). Even though the functional clustering of HLA class I molecules in superfamilies is based on significant redundancy of the presented sets of peptides[34], individual analysis of the responses elicited by each HLA class I isotypic or allelic variant remains desirable to identify the optimal epitopes they present. This is particularly important to devise a new reagent, such as tetramer (HLA-class I or HLA-class II) to monitor the immune response. For the same reason, it would be helpful to obtain strains of mice co-expressing HLA-A2.1 with other HLA class II molecules, even if the binding of peptides to HLA class II molecules is less restrictive than to class I molecules. Based on the disclosure herein, additional HLA class I-/class II-transgenic, H-2 class I-/class II-KO mice can be constructed for these and other purposes.

Whereas HLA-transgenic H-2-KO mice enable a detailed analysis and optimization of the immunogenicity of antigenic peptides with excellent transposability to humans (Rohrlich, P. S. et al., Int Immunol 15, 765-772 (2003); Loirat, D., Lemonnier, F. A. & Michel, M. L., J Immunol 165, 4748-4755 (2000); Scardino, A. et al., Eur J Immunol 31, 3261-3270 (2001)) this is less evident for vaccine adjuvant-formulation studies. This could be due to differences between the two species in the various effectors that are mobilized early in response to an antigenic challenge. Increasing fundamental knowledge of innate immunity might, in the future, lead to a more complete humanization of the mouse immune system.

In conclusion, the disclosure herein describes an optimized, humanized transgenic mouse model, whose H-2 class I (mouse β2m) and class II (H-2 IAβ$^b$) genes have been deleted and replaced with equivalent human genes HHD (HLA-A*0201), HLA-DRA*0101 and HLA-DRB1*0101. Cellular immunity in the HLA-A2.1-/HLA-DR1-transgenic H-2 class I-/class II-KO mice is completely restricted by the human HLA molecules, with a complete absence of immune responses restricted by the murine MHC molecules. The absence of competition between murine MHC and human (transgenic) HLA immune responses allows for use of these mice to characterize epitopes in human vaccines that require collaboration between HLA-restricted CD4$^+$ T helper and HLA-restricted CD8$^+$ T cytolytic cells.

"HLA" is the human MHC complex, and "H-2" the mouse MHC complex. The human complex comprises three class I α-chain genes, HLA-A, HLA-B, and HLA-C, and three pairs of MHC class II α- and β-chain genes, HLA-DR, -DP, and -DQ. In many haplotypes, the HLA-DR cluster contains an extra β-chain gene whose product can pair with the DRα chain, and so the three sets of genes give rise to four types of MHC class II molecules. In the mouse, the three class I α-chain genes are H-2-L, H-2-D, and H-2-K. The mouse MHC class II genes are H-2-A and H-2-E.

It is known in the art that genetic diversity exists between the HLA genes of different individuals as a result of both polymorphic HLA antigens and distinct HLA alleles. Accordingly, embodiments of the invention disclosed herein may substitute one polymorphic HLA antigen for another or one HLA allele for another. Examples of HLA polymorphisms and alleles can be found, for example, at http://www.anthonynolan.org.uk/HIG/data.html and http://www.ebi.ac.uk/imgt/hla, and in Genetic diversity of HLA: Functional and Medical Implication, Dominique Charon (Ed.), EDK Medical and Scientific International Publisher, and The HLA FactsBook, Steven G. E. Marsh, Peter Parham and Linda Barber, AP Academic Press, 2000.

A "disrupted" gene is one that has been mutated using homologous recombination or other approaches known in the art. A disrupted gene can be either a hypomorphic allele of the gene or a null allele of the gene. One of skill in the art will recognize that the type of allele to be used can be selected for any particular context. In many embodiments of the invention, a null allele is preferred.

"Homologous recombination" is a general approach for targeting mutations to a preselected, desired gene sequence of a cell in order to produce a transgenic animal (Mansour, S. L. et al., Nature 336:348-352 (1988); Capecchi, M. R., Trends Genet. 5:70-76 (1989); Capecchi, M. R., Science 244:1288-1292 (1989); Capecchi, M. R. et al., In: Current Communications in Molecular Biology, Capecchi, M. R. (ed.), Cold Spring Harbor Press, Cold Spring Harbor, N.Y. (1989), pp. 45-52; Frohman, M. A. et al., Cell 56:145-147 (1989)).

It is now be feasible to deliberately alter any gene in a mouse (Capecchi, M. R., Trends Genet. 5:70-76 (1989); Frohman, M. A. et al., Cell 56:145-147 (1989)). Gene targeting involves the use of standard recombinant DNA techniques to introduce a desired mutation into a cloned DNA sequence of a chosen locus. That mutation is then transferred through homologous recombination to the genome of a pluripotent, embryo-derived stem (ES) cell. The altered stem cells are microinjected into mouse blastocysts and are incorporated into the developing mouse embryo to ultimately develop into chimeric animals. In some cases, germ line cells of the chimeric animals will be derived from the genetically altered ES cells, and the mutant genotypes can be transmitted through breeding.

Gene targeting has been used to produce chimeric and transgenic mice in which an nptII gene has been inserted into the β$_2$-microglobulin locus (Koller, B. H. et al., Proc. Natl. Acad. Sci. (U.S.A.) 86:8932-8935 (1989); Zijlstra, M. et al., Nature 342:435-438 (1989); Zijlstra, M. et al., Nature 344:742-746 (1989); DeChiaba et al., Nature 345:78-80 (1990)). Similar experiments have enabled the production of chimeric and transgenic animals having a c-abl gene which has been disrupted by the insertion of an nptII gene (Schwartzberg, P. L. et al., Science 246:799-803 (1989)). The technique has been used to produce chimeric mice in which the en-2 gene has been disrupted by the insertion of an nptII gene (Joyner, A. L. et al., Nature 338:153-155 (1989)).

In order to utilize the "gene targeting" method, the gene of interest must have been previously cloned, and the intron-exon boundaries determined. The method results in the insertion of a marker gene (e.g., an nptII gene) into a translated region of a particular gene of interest. Thus, use of the gene targeting method results in the gross destruction of the gene of interest.

Significantly, the use of gene targeting to alter a gene of a cell results in the formation of a gross alteration in the sequence of that gene. The efficiency of gene targeting depends upon a number of variables, and is different from construct to construct.

The chimeric or transgenic animal cells of the present invention are prepared by introducing one or more DNA molecules into a cell, which may be a precursor pluripotent cell, such as an ES cell, or equivalent (Robertson, E. J., In: Current Communications in Molecular Biology, Capecchi, M. R. (ed.), Cold Spring Harbor Press, Cold Spring Harbor, N.Y. (1989), pp. 39-44). The term "precursor" is intended to denote only that the pluripotent cell is a precursor to the desired ("transfected") pluripotent cell, which is prepared in accordance with the teachings of the present invention. The pluripotent (precursor or transfected) cell can be cultured in vivo in a manner known in the art (Evans, M. J. et al., Nature 292:154-156 (1981)) to form a chimeric or transgenic animal.

Any ES cell can be used in accordance with the present invention. It is, however, preferred to use primary isolates of ES cells. Such isolates can be obtained directly from embryos, such as the CCE cell line disclosed by Robertson, E. J., In: Current Communications in Molecular Biology, Capecchi, M. R. (ed.), Cold Spring Harbor Press, Cold Spring Harbor, N.Y. (1989), pp. 39-44), or from the clonal isolation of ES cells from the CCE cell line (Schwartzberg, P. A. et al., Science 246:799-803 (1989), which reference is incorporated herein by reference). Such clonal isolation can be accomplished according to the method of E. J. Robertson (In: Teratocarcinomas and Embryonic Stem Cells: A Practical Approach, (E. J. Robertson, Ed.), IRL Press, Oxford, 1987), which reference and method are incorporated herein by reference. The purpose of such clonal propagation is to obtain ES cells, which have a greater efficiency for differentiating into an animal. Clonally selected ES cells are approximately 10-fold more effective in producing transgenic animals than the progenitor cell line CCE. For the purposes of the recombination methods of the present invention, clonal selection provides no advantage.

An example of ES cell lines, which have been clonally derived from embryos, are the ES cell lines, AB1 (hprt$^+$) or AB2.1 (hprt$^-$). The ES cells are preferably cultured on stromal cells (such as STO cells (especially SNC4 STO cells) and/or primary embryonic fibroblast cells) as described by E. J. Robertson (In: Teratocarcinomas and Embryonic Stem Cells: A Practical Approach, (E. J. Robertson, Ed., IRL Press, Oxford, 1987, pp 71-112), which reference is incorporated herein by reference. Methods for the production and analysis of chimeric mice are disclosed by Bradley, A. (In: Teratocarcinomas and Embryonic Stem Cells: A Practical Approach, (E. J. Robertson, Ed.), IRL Press, Oxford, 1987, pp 113-151), which reference is incorporated herein by reference. The stromal (and/or fibroblast) cells serve to eliminate the clonal overgrowth of abnormal ES cells. Most preferably, the cells are cultured in the presence of leukocyte inhibitory factor ("lif") (Gough, N. M. et al., Reprod. Fertil. Dev. 1:281-288 (1989); Yamamori, Y. et al., Science 246:1412-1416 (1989), both of which references are incorporated herein by reference). Since the gene encoding lif has been cloned (Gough, N. M. et al., Reprod. Fertil. Dev. 1:281-288 (1989)), it is especially preferred to transform stromal cells with this gene, by means known in the art, and to then culture the ES cells on transformed stromal cells that secrete lif into the culture medium.

As used herein, the term "transgene" refers to a nucleic acid sequence, which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can be operably linked to one or more transcriptional regulatory sequences and any other nucleic acid, such as introns, that may be necessary for optimal expression of a selected nucleic acid. Exemplary transgenes of the present invention encode, for instance an H-2 polypeptide. Other exemplary transgenes are directed to disrupting one or more HLA genes by homologous recombination with genomic sequences of an HLA gene.

A "functional transgene" is one that produces an mRNA transcript, which in turn produces a properly processed protein in at least one cell of the mouse comprising the transgene. One of skill will realize that the diverse set of known transcriptional regulatory elements and sequences directing posttranscriptional processing provide a library of options from which to direct the expression of a transgene is a host mouse. In many embodiments of the invention, expression of an HLA transgene under the control of an H-2 gene regulatory element may be preferred.

In some embodiments, the HLA class I transgene is an HLA-A2 transgene and the HLA class II transgene is an HLA-DR1 transgene. An example of an HLA-A2 transgene is one that comprises the HLA-A2 sequence provided in the sequence listing. An example of an HLA-DR1 transgene is one that comprises the HLA-DR1 sequence provided in the sequence listing.

In an embodiment, the invention provides a transgenic mouse deficient for both H2 class I and class II molecules, wherein the transgenic mouse comprises a functional HLA class I transgene and a functional HLA class II transgene. In some embodiments, the mouse has the genotype HLA-A2$^+$ HLA-DR1$^+$β2m°IAβ°. In other embodiments the HLA-A2 transgene comprises the HLA-A2 sequence provided in the sequence listing and the HLA-DR1 transgene comprises the HLA-DR1 sequence provided in the sequence listing.

The invention also provides isolated transgenic mouse cells. In some cases the cell comprises a disrupted H2 class I gene, a disrupted H2 class II gene, and a functional HLA class I or class II transgene. In others, the cell comprises a disrupted H2 class I gene, a disrupted H2 class II gene, a functional HLA class I transgene, and a functional HLA class II transgene. The HLA class I transgene can be an HLA-A2 transgene and the HLA class II transgene can be an HLA-DR1 transgene. In some cases, the HLA-A2 transgene comprises the HLA-A2 sequence provided in the sequence listing and the HLA-DR1 transgene comprises the HLA-DR1 sequence provided in the sequence listing.

In an embodiment, the invention provides an isolated transgenic mouse cell deficient for both H2 class I and class II molecules, wherein the transgenic mouse comprises a functional HLA class I transgene and a functional HLA class II transgene. The isolated transgenic mouse cells can have the genotype HLA-A2$^+$HLA-DR1$^+$β2m°IAβ°. The HLA-A2 transgene can comprise the HLA-A2 sequence provided in the sequence listing and the HLA-DR1 transgene can comprise the HLA-DR1 sequence provided in the sequence listing.

The isolated transgenic mouse cells of the invention can have the genotype of any mouse of the invention. However, the set of genotypes of the isolated transgenic mouse cells of the invention, and the set of genotypes of the mice of the invention are not necessarily entirely overlapping.

The isolated mouse cells of the invention can be obtained from a mouse or mouse embryo. In one embodiment, the mouse or mouse embryo has the same genotype as the cell to be obtained. In another embodiment, the mouse or mouse embryo has a different genotype than the cell to be obtained. After the cell is obtained from the mouse or mouse embryo, a gene of the cell can be disrupted by, for example, homologous recombination. Additionally, a functional transgene can be introduced into the genome of the cell by, for example, transfection. One of skill in the art will recognize that any suitable method known in the art can be applied to modify the genome of the cell to thereby obtain an isolated mouse cell having the desired genotype.

An additional object of the invention is an isolated transgenic mouse cell deficient for both H2 class I and class II molecules, wherein the transgenic mouse cell comprises a functional HLA class I transgene and a functional HLA class II transgene. In some embodiments, the transgenic mouse cell has the genotype HLA-A2$^+$HLA-DR1$^+$β2m°IAβ°. In other embodiments, the HLA-A2 transgene comprises the HLA-A2 sequence provided in the sequence listing and the HLA-DR1 transgene comprises the HLA-DR1 sequence provided in the sequence listing.

T cells play a central role in many aspects of acquired immunity, carrying out a variety of regulatory and defensive functions. When some T cells encounter an infected or cancerous cell, they recognize it as foreign and respond by acting as killer cells, killing the host's own cells as part of the cell-mediated immune response. Other T cells, designated helper T cells, respond to perceived foreign antigens by stimulating B cells to produce antibodies, or by suppressing certain aspects of a humoral or cellular immune response.

T helper cells (Th) orchestrate much of the immune response via the production of cytokines. Although generally identifiable as bearing the CD4 cell surface marker, these cells are functionally divided into Th1 or Th2 subpopulations according to the profile of cytokines they produce and their effect on other cells of the immune system.

The Th1 cells detect invading pathogens or cancerous host cells through a recognition system referred to as the T cell antigen receptor. Termed cellular immunity, Th1-related processes generally involve the activation of non-B cells and are frequently characterized by the production of IFN-γ. Nevertheless, although the Th1 system is primarily independent from the production of humoral antibodies, Th1 cytokines do promote immunoglobulin class switching to the IgG$_{2a}$ isotype.

Upon detection of a foreign antigen, most mature Th1 cells direct the release of IL-2, IL-3, IFN-γ, TNF-β, GM-CSF, high levels of TNF-α, MIP-1α, MIP-1β, and RANTES. These cytokines promote delayed-type hypersensitivity and general cell-mediated immunity. IL-2, for instance, is a T cell growth factor that promotes the production of a clone of additional T cells sensitive to the particular antigen that was initially detected. The sensitized T cells attach to and attack cells or pathogens containing the antigen.

In contrast, mature Th2 cells tend to promote the secretion of IL-3, IL-4, IL-5, IL-6, IL-9, IL-10, IL-13, GM-CSF, and low levels of TNF-α. In addition, the Th2 response promotes humoral immunity by activating B cells, stimulating antibody production and secretion, and inducing class switching to IgA, IgG$_1$ and IgE isotypes.

As used herein, an "antigen" comprises: 1) at least one HTL epitope, or 2) at least one CTL epitope or, 3) at least one B cell epitope, or 4) at least one HTL epitope and at least one CTL epitope, or 5) at least one HTL epitope and at least one B cell epitope, or 6) at least one CTL epitope and at least one B cell epitope, or 7) at least one HTL epitope and at least one CTL epitope and at least one B cell epitope. A "candidate antigen" is a molecule that is under investigation to determine whether it functions as an antigen.

A "humoral immune response" is antibody-mediated specific immunity.

An "epitope" is a site on an antigen that is recognized by the immune system. An antibody epitope is a site on an antigen recognized by an antibody. A T-cell epitope is a site on an antigen that binds to an MHC molecule. A TH epitope is one that binds to an MHC class II molecule. A CTL epitope is one that binds to an MHC class I molecule.

The antigen can comprise a polypeptide sequence or a polynucleotide sequence, which can comprise RNA, DNA, or both. In one embodiment, the antigen comprises at least one polynucleotide sequence operationally encoding one or more antigenic polypeptides. Used in this context, the word "comprises" intends that at least one antigenic polypeptide is provided by the transcription and/or translation apparatus of a host cell acting upon an exogenous polynucleotide that encodes at least one antigenic polypeptide, as described, for example in U.S. Pat. Nos. 6,194,389 and 6,214,808.

Antigens of the invention can be any antigenic molecule. Antigenic molecules include: proteins, lipoproteins, and glycoproteins, including viral, bacterial, parasitic, animal, and fungal proteins such as albumins, tetanus toxoid, diphtheria toxoid, pertussis toxoid, bacterial outer membrane proteins (including meningococcal outer membrane protein), RSV-F protein, malarial derived peptide, B-lactoglobulin B, aprotinin, ovalbumin, lysozyme, and tumor associated antigens such as carcinoembryonic antigen (CEA), CA 15-3, CA 125, CA 19-9, prostrate specific antigen (PSA), and the TAA complexes of U.S. Pat. No. 5,478,556, which is incorporated herein by reference in its entirety; carbohydrates, including naturally-occurring and synthetic polysaccharides and other polymers such as ficoll, dextran, carboxymethyl cellulose, agarose, polyacrylamide and other acrylic resins, poly (lactide-co-glycolide), polyvinyl alcohol, partially hydrolyzed polyvinyl acetate, polyvinylpryrolidine, Group B Steptococcal and Pneumococcal capsular polysaccharides (including type III), *Pseudomonas aeruginosa* mucoexopolysaccharide, and capsular polysaccharides (including fisher type I), and *Haemophilus influenzae* polysaccharides (including PRP); haptens, and other moieties comprising low molecular weight molecules, such as TNP, saccharides, oligosaccharides, polysaccharides, peptides, toxins, drugs, chemicals, and allergens; and haptens and antigens derived from bacteria, rickettsiae, fungi, viruses, parasites, including Diphtheria, Pertussis, Tetanus, *H. influenzae, S. pneumoniae, E. coli, Klebsiella, S. aureus, S. epidermidis, N. meningiditis*, Polio, Mumps, measles, rubella, Respiratory Syncytial Virus, Rabies, Ebola, Anthrax, *Listeria*, Hepatitis A, B, C, Human Immunodeficiency Virus I and II, Herpes simplex types 1 and 2, CMV, EBV, Varicella Zoster, Malaria, Tuberculosis, *Candida albicans*, and other *candida, Pneumocystis carinii, Mycoplasma, Influenzae* virus A and B, Adenovirus, Group A *streptococcus*, Group B *streptococcus, Pseudomonas aeryinosa*, Rhinovirus, *Leishmania, Parainfluenzae*, types 1, 2 and 3, Coronaviruses, *Salmonella, Shigella, Rotavirus, Toxoplasma*, Enterovirusses, and *Chlamydia trachomatis* and *pneumoniae*.

As used herein, a pharmaceutical composition or vaccine comprises at least one immunological composition, which can be dissolved, suspended, or otherwise associated with a pharmaceutically acceptable carrier or vehicle. Any pharmaceutically acceptable carrier can be employed for administration of the composition. Suitable pharmaceutical carriers are described in Remington's Pharmaceutical Sciences, 18th Edition (A. Gennaro, ed., 1990) Mack Pub., Easton, Pa., which is incorporated herein by reference in its entirety.

Carriers can be sterile liquids, such as water, polyethylene glycol, dimethyl sulfoxide (DMSO), oils, including petroleum oil, animal oil, vegetable oil, peanut oil, soybean oil, mineral oil, sesame oil, and the like. Carriers can be in the form of mists, sprays, powders, waxes, creams, suppositories, implants, salves, ointments, patches, poultices, films, or cosmetic preparations.

Proper formulation of the pharmaceutical composition or vaccine is dependent on the route of administration chosen. For example, with intravenous administration by bolus injection or continuous infusion, the compositions are preferably water soluble, and saline is a preferred carrier. For transcutaneous, intranasal, oral, gastric, intravaginal, intrarectal, or other transmucosal administration, penetrants appropriate to the barrier to be permeated can be included in the formulation and are known in the art. For oral administration, the active ingredient can be combined with carriers suitable for inclusion into tablets, pills, dragees, capsules, liquids, gels, syrups, slurries, suspensions, and the like. Time-sensitive delivery systems are also applicable for the administration of the compositions of the invention. Representative systems include polymer base systems, such as poly(lactide-glycoside), copolyoxalates, polycaprolactones, polyesteramides, polyorthoesters, polyhydroxybutyric acid and polyanhydrides. These and like polymers can be formulated into microcapsules according to methods known in the art, for example, as taught in U.S. Pat. No. 5,075,109, which is incorporated herein by reference in its entirety. Alternative delivery systems appropriate for the administration of the disclosed immunostimulatory compounds of the invention include those disclosed in U.S. Pat. Nos. 6,194,389, 6,024,983, 5,817,637, 6,228,621, 5,804,212, 5,709,879, 5,703,055, 5,643,605, 5,643,574, 5,580,563, 5,239,660, 5,204,253, 4,748,043, 4,667,014, 4,452,775, 3,854,480, and 3,832,252 (each of which is incorporated herein by reference in its entirety).

Aqueous dextrose and glycerol solutions can also be employed as liquid carriers, particularly for injectable or aerosol solutions. For administration by aerosol, as by pressurized spray or nebulizer, suitable propellants can be added as understood by those familiar with the art. The immunological composition can also be formulated with solubilizing agents; emulsifiers; stabilizers; dispersants; flavorants; adjuvants; carriers; topical anesthetics, such as lidocaine, xylocaine, and the like; antibiotics; and known or suspected anti-viral, anti-fungal, anti-parasitic, or anti-tumor compounds.

An "adjuvant" is a composition that promotes or enhances an immune response to a target antigen. One of skill in the art can select an appropriate adjuvant for use in practicing the present invention in view of the disclosure herein.

The present invention encompasses methods of treating a patient in need of immune stimulation by administering a composition comprising one or more antigens of the invention. As used herein, treatment encompasses corrective, restorative, ameliorative, and preventive methods relating to any disease, condition, abnormality, or symptom. Treatment further encompasses the elicitation or suppression of an immune response in an experimental animal or ex vivo.

Thus, treatment comprises administering an immunostimulatory amount of any of the immunostimulatory compositions of the invention by any method familiar to those of ordinary skill in the art, commonly including oral and intranasal routes, and intravenous, intramuscular, and subcutaneous injections, but also encompassing, intraperitoneal, intracorporeal, intra-articular, intraventricular, intrathecal, topical, tonsillar, mucosal, transdermal, intravaginal administration and by gavage.

As is recognized by the skilled practitioner, choosing an appropriate administration method may contribute to the efficacy of a treatment, and local administration may be preferred for some applications. Acceptable routes of local administration include subcutaneous, intradermal, intraperitoneal, intravitreal, inhalation or lavage, oral, intranasal, and directed injection into a predetermined tissue, organ, joint, tumor, or cell mass. For example, mucosal application or injection into mucosal lymph nodes or Peyer's patches may promote a humoral immune response with substantial IgA class switching. Alternatively, targeted injection into a lesion, focus, or affected body site may be applicable for the treatment of solid tumors, localized infections, or other situs requiring immune stimulation.

Alternatively, cells of the immune system (e.g., T cells, B cells, NK cells, or oligodendrocytes) can be removed from a host and treated in vitro. The treated cells can be further cultured or reintroduced to a patient (or to a heterologous host) to provide immune stimulation to the patient or host. For example, bone marrow cells can be aspirated from a patient and treated with an HDR to stimulate global or specific immunity. High-dose radiation, or comparable treatments, can then be used to destroy the remaining immune cells in the patient. Upon re-implantation, the autologous stimulated cells will restore normal immune function in the patient. Alternatively, NK and/or T cells isolated from a patient suffering from cancer may be exposed in vitro to one or more antigens specific to the patient's cancer. Upon re-implantation into the patient, the antigen-stimulated cells will deploy a vigorous cellular immune response against the cancerous cells.

An immunostimulatory (efficacious) amount refers to that amount of vaccine that is able to stimulate an immune response in a patient, which is sufficient to prevent, ameliorate, or otherwise treat a pathogenic challenge, allergy, or immunologic abnormality or condition. An immunostimulatory amount is that amount, which provides a measurable increase in a humoral or cellular immune response to at least one epitope of the antigen as compared to the response obtained if the antigen is administered to the patient without prior treatment with the vaccine. Thus, for example, an immunostimulatory amount refers to that amount of an antigen-containing composition that is able to promote the production of antibodies directed against an antigenic epitope of interest or stimulate a detectable protective effect against a pathogenic or allergenic challenge or to promote a protective CTL response against an antigenic epitope of interest.

Treatment with an immunostimulatory amount of an antigen-containing composition of the invention comprises effecting any directly, indirectly, or statistically observable or measurable increase or other desired change in the immune response in a host, specifically including an ex vivo tissue culture host, comprising at least one cell of the immune system or cell line derived therefrom. Host cells can be derived from human or animal peripheral blood, lymph nodes or the like. Preferred tissue culture hosts include freshly isolated T cells, B cells, macrophages, oligodendrocytes, NK cells, and monocytes, each of which can be isolated or purified using standard techniques. Observable or measurable responses include, B or T cell proliferation or activation; increased antibody secretion; isotype switching; increased cytokine release, particularly the increased release of one or more of IL-1, IL-2, IL-3, IL-4, IL-5, IL-6, IL-9, IL-10, IL-12, IL-13, GM-CSF, IFN-γ, TNF-α, TNF-β, GM- CSF, MIP-1α, MIP-1β, or RANTES; increased antibody titer or avidity against a specific antigen; reduced morbidity or mortality rates associated with a pathogenic infection; promoting, inducing, maintaining, or reinforcing viral latency; suppressing or otherwise ameliorating the growth, metastasis, or effects of malignant and non-malignant tumors; and providing prophylactic protection from a disease or the effects of a disease.

Where the suppression of an immunological response is desired, for example, in the treatment of autoimmune disease or allergy, an effective amount also encompasses that amount sufficient to effect a measurable or observable decrease in a response associated with the condition or pathology to be treated.

The amount of an antigen-containing composition to be administered and the frequency of administration can be determined empirically and will take into consideration the age and size of the patient being treated, and the condition or disease to be addressed. An appropriate dose is within the range of 0.01 µg to 100 µg per inoculum, but higher and lower amounts may also be indicated. Secondary booster immunizations can be given at intervals ranging from one week to many months later.

The following examples demonstrate certain embodiments of the invention. One of ordinary skill in the art will recognize the numerous modifications and variations that may be performed without altering the spirit or scope of the present invention. Such modifications and variations are believed to be encompassed within the scope of the invention. The examples do not in any way limit the invention.

EXAMPLES

The following experimental techniques and reagents were used to demonstrate certain nonlimiting embodiments of the invention.

Transgenic Mice

The HLA-DR1-transgenic H-2 class II-KO (IA $\beta^{b\circ}$) mice were obtained at the Institut Pasteur of Lille by crossing HLA-DR1-transgenic mice (Altmann, D. M. et al., *J Exp Med* 181, 867-875 (1995)) with H-2 class II-KO (IA $\beta^{b\circ}$) mice (Rohrlich, P. S. et al., *Int Immunol* 15, 765-772 (2003)). The HLA-A2.1-transgenic mice, expressing a chimeric monochain (HHD molecule: α1-α2 domains of HLA-A2.1, α3 to cytoplasmic domains of H-2 $D^b$, linked at its N-terminus to the C terminus of human β2m by a 15 amino-acid peptide linker) were created (Pascolo, S. et al., J Exp Med 185, 2043-2051 (1997)). HLA-A2.1 (HHD)-transgenic H-2 class I-KO and HLA-DR1-transgenic H-2 class II-KO (IA $\beta^{b\circ}$) mice were intercrossed and progenies screened until HLA-A2.1$^{+/-}$/HLA-DR1$^{+/-}$ double transgenic H-2-class I (β2m$^\circ$)-/class II (IAβ$^\circ$)-KO animals were obtained and used for the experiments described herein. HLA-A2.1$^{+/-}$ single transgenic H-2-class I (β2m$^\circ$)-/class II (IAβ$^\circ$)-KO mice were used as controls in the protection assays. Mice were bred in the animal facilities at the Institut Pasteur, Paris; all protocols were reviewed by the Institut Pasteur competent authority for compliance with the French and European regulations on Animal Welfare and with Public Health Service recommendations.

Genotyping

The HLA-DRB1*0101, HLA-DRA*0101 and HLA-A*0201 transgenes were detected by PCR. Tail-DNA was extracted after overnight incubation at 56° C. in 100 mM NaCl, 50 mM Tris-HCl pH 7.2, 100 mM EDTA, 1% SDS and 0.5 mg/ml proteinase K, followed by the addition of 250 µl of saturated NaCl solution and isopropanol precipitation. The samples were washed (3×) in 70% ethanol and resuspended in 150 µl of 10 mM Tris-HCl, 1 mM EDTA pH 8. PCR conditions were: 1.5 mM $MgCl_2$, 1.25 U of Taq Polymerase, buffer supplied by the manufacturer (InVitrogen, Carlsbad, Calif.), 1 cycle (7 min, 94° C.), 40 cycles (30 sec, 94° C.; 30 sec, 60° C.; 1 min, 72° C.), 1 cycle (4 min, 72° C.), using as forward and reverse primers, for HHD: 5'CAT TGA GAC AGA GCG CTT GGC ACA GAA GCA G 3' and 5'GGA TGA CGT GAG TAA ACC TGA ATC TTT GGA GTA CGC 3', for HLA-DRB1*0101: 5' TTC TTC AAC GGG ACG GAG CGG GTG 3' and 5' CTG CAC TGT GAA GCT CTC ACC AAC 3', and for HLA-DRA*0101: 5' CTC CAA GCC CTC TCC CAG AG 3' and 5' ATG TGC CTT ACA GAG GCC CC 3'.

FACS Analysis

Cytofluorimetry studies were performed on red-blood cell-depleted, Lympholyte M-purified (Tebu-bio, Le Perray en Yvelines, France) splenocytes using FITC-conjugated W6/32 (anti-HLA-ABC, Sigma, St Louis, Mo.) and biotinilated anti-28-8-6S (anti-H-2 $K^b/D^b$, BD Biosciences, San Diego, Calif.) m.Ab. CD4$^+$ and CD8$^+$ T lymphocytes were stained using PE-labeled CT-CD4 anti-mouse CD4 (CALTAG, South San Francisco, Calif.) and FITC-labeled 53-6.7 anti-mouse CD8 m.Ab (BD Biosciences). Analysis of MHC class II molecule expression was performed on B220$^+$ B lymphocytes positively selected on MS columns (Miltenyi Biotec, Bergisch Gladbach, Germany). Following saturation of Fc receptors with 2.4G2 m.Ab, expression of HLA-DR1 and H-2 IA$^b$ was analyzed using FITC-labeled L243 (anti-HLA-DR) and PE-labeled AF6-120.1 (anti-H-2 IAβ$^b$) m.Ab (BD Biosciences). Paraformaldehyde fixed cells were analyzed with a FACSCalibur (Becton Dickinson, Bedford, Mass.).

Immunoscope Analyses

CD4$^+$ and CD8$^+$ T cells from naive mice were positively selected on Auto-Macs (Miltenyi Biotec), RNA prepared using RNA Easy Kit (Qiagen, Hilden, Germany) and used for cDNA synthesis. The cDNA was PCR-amplified using forward primers specific for each BV segment family and a reverse primer shared by the two BC segments. PCR-products were subjected to a run-off-elongation with internal BC FAM-tagged primer. The run-off products were loaded on a 6% acrylamide/8 M urea gel for separation (7 h, 35 W) with a 373A DNA sequencer (Perkin Elmer Applied Biosystem, Foster City, Calif.). Data were analyzed using immunoscope software (Pannetier, C. et al., *Proc Natl Acad Sci USA* 90, 4319-4323 (1993)).

Peptides

The HLA-A2 binding peptides $HBsAg_{348-357}$ GLSPT-VWLSV and $HBsAg_{335-343}$ WLSLLVPFV, the H-2 K$^b$ binding peptide $HBsAg_{371-378}$ ILSPFLPL, the HLA-DR1 binding peptide $HBsAg_{180-195}$ QAGFFLLTRILTIPQS, the H-2 IA$^b$ binding peptide $HBsAg_{126-138}$ RGLYFPAGGSSSG and the preS2 peptide $HBsAg_{109-134}$ MQWNSTTFHQTLQD-PRVRGLYFPAGG were synthesized by Neosystem (Strasbourg, France) and dissolved in PBS-10% DMSO at a concentration of 1 mg/ml. The numbering of the amino acid sequence of peptides starts from the first methionine of the HBV ayw subtype preS1 domain.

Immunization with DNA Encoding the S2-S Proteins of HBV

The pCMV-S2.S plasmid vector (Michel, M. L. et al., *Proc Natl Acad Sci USA* 92, 5307-5311 (1995)) coding for the preS2 and the S HBV surface antigens expressed under the control of the human CMV immediate early gene promotor was purified on Plasmid Giga Kit columns under endotoxin free conditions (Qiagen). Anesthesized mice were injected (50 µg each side) into regenerating tibialis anterior muscles, as previously described (Davis, H. L., Michel, M. L. & Whalen, R. G., *Hum Mol Genet* 2, 1847-1851 (1993)).

T Cell Proliferation Assay

Twelve days after the last immunization, red-blood cell-depleted, Ficoll-purified splenocytes ($5 \cdot 10^6$ cells/25 cm$^2$ culture flask (Techno Plastic Products (TPP), Trasadingen, Switzerland)) were co-cultured with peptide-pulsed (20 µg/ml), γ-irradiated (180 Gy) LPS-blasts ($5 \cdot 10^6$ cells/culture flask) in RPMI medium supplemented with 10% FCS, 10 mM HEPES, 1 mM sodium pyruvate, $5 \times 10^{-5}$ M 2-mercaptoethanol, 100 I.U/ml penicillin and 100 µg streptomycin, as described (Loirat, D., Lemonnier, F. A. & Michel, M. L., *J Immunol* 165, 4748-4755 (2000)). On day 7, for proliferation assays, cells were plated ($5 \times 10^5$ cells/well of flat bottomed 96 well microplates, (TPP)) with peptide-pulsed irradiated LPS-Blasts ($2 \times 10^5$ cells/well) for 72 h in complete RPMI medium supplemented with 3% FCS. Cells were pulsed for the final 16 h with 1 µCi of ($^3$H)-thymidine per well before being harvested on filtermates with a TOMTEC collector (Perkin Elmer Applied Biosystem), and incorporated radioactivity was measured on a micro-β counter (Perkin Elmer Applied Biosystem). Results are given as stimulation index (SI)=cpm with specific peptide/cpm with irrelevant peptide.

Measurement of CTL Activity

Cytotoxicity assays were performed on the same immune splenocyte populations as the proliferation assays. Responder cells ($5 \cdot 10^6$ cells/25 cm$^2$ culture flask, TPP) and stimulating peptide-pulsed (20 µg/ml), γ-irradiated (180 Gy) LPS-blasts ($5 \cdot 10^6$ cells/culture flask) were co-cultured for 7 days in the same supplemented RPMI medium as for proliferation assays. Cytolytic activity was tested in a standard 4 h $^{51}$Cr assay against RMA-S HHD target cells pulsed with 10 µg/ml of the experimental or control peptides. Specific lysis, in %, was calculated in duplicates, according to: [experimental−spontaneous release]/[maximal−spontaneous release]×100, substracting the non-specific lysis observed with the control peptide.

Measurement of In Vivo Antibody Production

At various times before and after DNA injection, blood was collected from mice by retrobulbar puncture with heparinized glass pipettes, and sera recovered by centrifugation were assayed for anti-HBs and anti-preS2 by specific ELISA. Purified recombinant particles containing HBV small S protein (1 ug/ml) or preS2 (120-145) synthetic peptide (1 ug/ml) were used as the solid phase. After blocking with PBST (PBS containing 0.1% Tween 20) supplemented with 10% FCS, serial dilutions were added. After extensive washing, the bound antibodies were detected with anti mouse Ig (total IgG) labeled with horseradish peroxidase (Amersham, Little Chalfont, UK). Antibody titers were determined by the serial end-point dilution method. Mouse sera were tested individually, and titers were the mean of at least three determinations. Serum dilutions below 1/100 were considered negative.

Antibody Titration

Sera from immunized mice were individually assayed by ELISA (Michel, M. L. et al., *Proc Natl Acad Sci USA* 92, 5307-5311 (1995)) on either purified HBV middle and small proteins or preS2 synthetic HBs$_{109\text{-}134}$ peptide, After blocking with PBS 1× supplemented with 0.1% Tween 20, 10% FCS and washings (×3), bound antibodies were detected with horseradish peroxidase-labeled anti-mouse IgG (Amersham, Little Chalfont, UK). Antibody titers (means of at least 3 determinations) were determined by the serial end-point dilution method. Titers below 1/100 were considered negative.

Vaccinia Challenge and Plaque Assay

DNA-injected mice were challenged intraperitoneally 12 days post last injection with 10$^7$ PFU of recombinant vaccinia virus (Western Reserve strain) expressing either the HbsAg (Smith, G. L., Mackett, M. & Moss, B., *Nature* 302, 490-495 (1983)) or the HBx protein (Schek, N., Bartenschlager, R., Kuhn, C. & Schaller, H., *Oncogene* 6, 1735-1744. (1991)) kindly provided, respectively, by Dr B. Moss and Dr H. Schaller. Four days later, ovaries were assayed for rVV titers by plaque assay on BHK 21 cells (Buller, R. M. & Wallace, G. D., *Lab Anim Sci* 35, 473-476 (1985).

Example 1: Cell Surface Expression of MHC Molecules

Figure 1B:
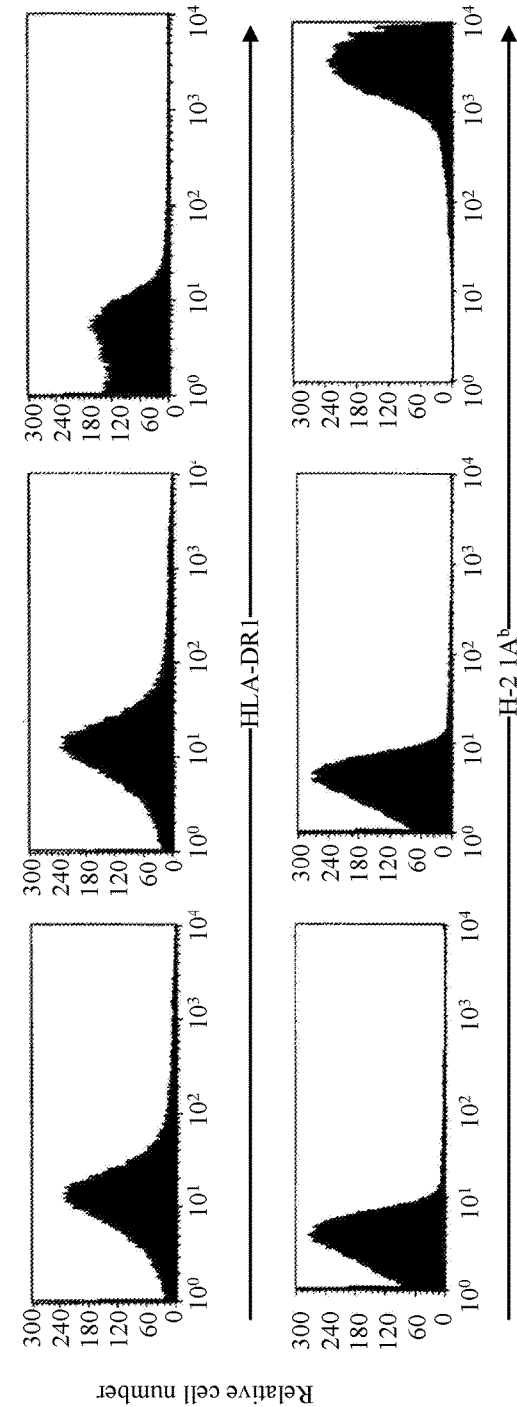

Cell surface expression of the HLA-A2.1, H-2 K$^b$/D$^b$, HLA-DR1, and H-2 IA$^b$ molecules was evaluated on splenocytes by flow cytometry. As illustrated in FIG. 1*a*, a similar level of HLA-A2.1 expression was observed in HLA-A2.1-/HLA-DR1-transgenic, H-2 class I-/class II-KO mice and HLA-A2.1-transgenic, H-2 class I-KO mice, while HLA-A2.1 was absent and H-2 K$^b$/D$^b$ expressed exclusively in HLA-DR1-transgenic, H-2 class II-KO mice. Cell surface expression of HLA-DR1 and H-2 IA$^b$ was measured on B220$^+$-enriched B cells. As shown in FIG. 1*b*, a similar level of HLA-DR1 expression was observed in HLA-A2.1-/HLA-DR1-transgenic, H-2 class I-/class II-KO mice and HLA-DR1-transgenic, H-2 class II-KO mice, whereas no expression was detected in HLA-A2.1-transgenic, H-2 class I-KO mice. Cell surface expression of the transgenic molecules (especially HLA-DR1) was, however, lower than the expression of endogenous H-2 class I and class II molecules.

Example 2: Peripheral CD4$^+$ and CD8$^+$ T Cells

Figure 2A:
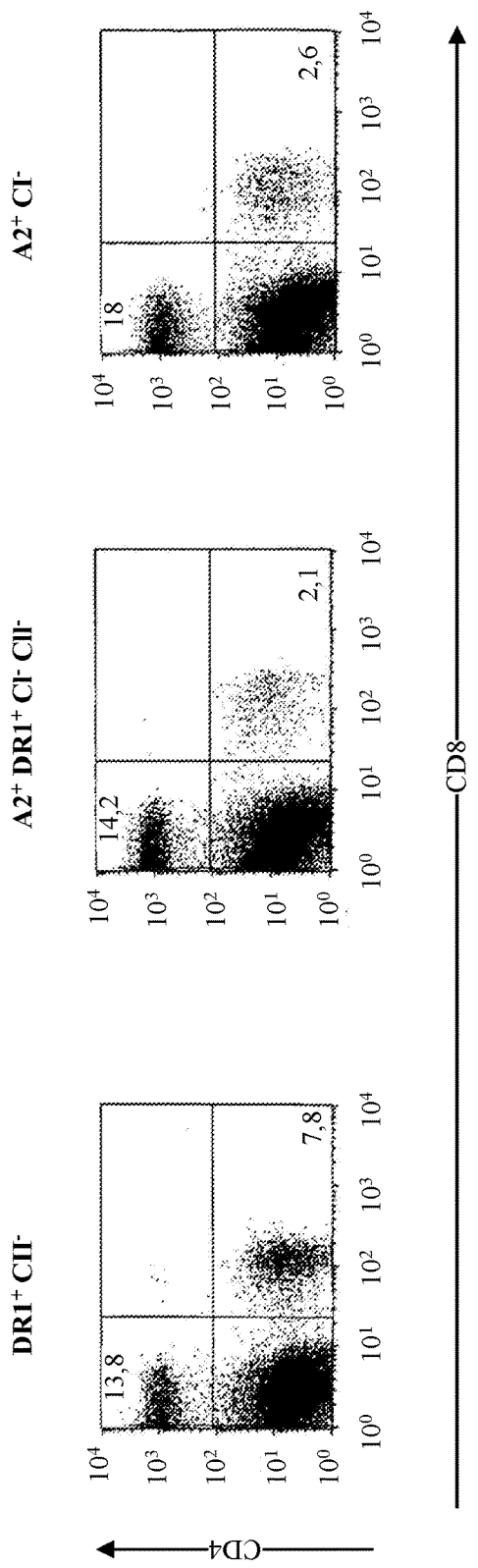
FIGS. 2A, 2B, and 2C show CD8$^+$ and CD4$^+$ splenic T cell numbers and BV segment usage (based on an immunoscope analysis) in mice of the indicated genotypes.

CD4$^+$ and CD8$^+$ splenic T cell numbers were determined by immunostaining and flow cytometry analysis as illustrated in FIG. 2*a*.

CD4$^+$ T cells represented 13-14% of the splenocyte population in both HLA-A2.1-/HLA-DR1-transgenic, H-2 class I/class II-KO mice and HLA-DR1-transgenic, H-2 class II-KO mice. In contrast, only 2-3% of the cells were CD4$^+$ in H-2 class II-KO mice (data not shown), in agreement with the initial report on mice lacking MHC class II molecules (Cosgrove, D. et al., *Cell* 66, 1051-1066 (1991)). As expected, expression of transgenic HLA-A2.1 molecules led to an increase in the size of the peripheral CD8$^+$ T cell population, which reached 2-3% of the total splenocytes in both HLA-A2.1-/HLA-DR1-transgenic, H-2 class I/class II-KO mice and HLA-A2.1-transgenic, H-2 class I-KO mice, compared to 0.6-1% in the β2 microglobulin (β2m)-KO MHC class I-deficient mice (Pascolo, S. et al., *J Exp Med* 185, 2043-2051 (1997)).

The results presented in Examples 1 and 2 show that:

(1) In the HLA-A2$^+$HLA-DR1$^+$ β2m°IAβ° mouse, the expression of HLA-A2 molecules, the absence of expression of H2-K$^b$ molecules, the number of CD8$^+$ peripheral T-lymphocytes, and the diversity of the CD8$^+$ T repertoire are generally comparable to the HLA-A2$^+$ β2m° mouse;

(2) In the HLA-A2$^+$HLA-DR1$^+$ β2m°IAβ° mouse, the expression of HLA-DR1 molecules, the absence of expression of H2-IA$^b$ molecules, the number of CD4$^+$ T-lymphocytes, and the diversity of the CD4+ repertoire are generally comparable to the HLA-DR1+IAβ° mouse; and (3) The HLA-A2+HLA-DR1+ β2m°IAβ° mouse has all the characteristic advantages found in HLA-A2+β2m° mice, and the HLA-DR1+IA β° mice.

Example 3: TCR BV Segment Usage

Figure 2B:
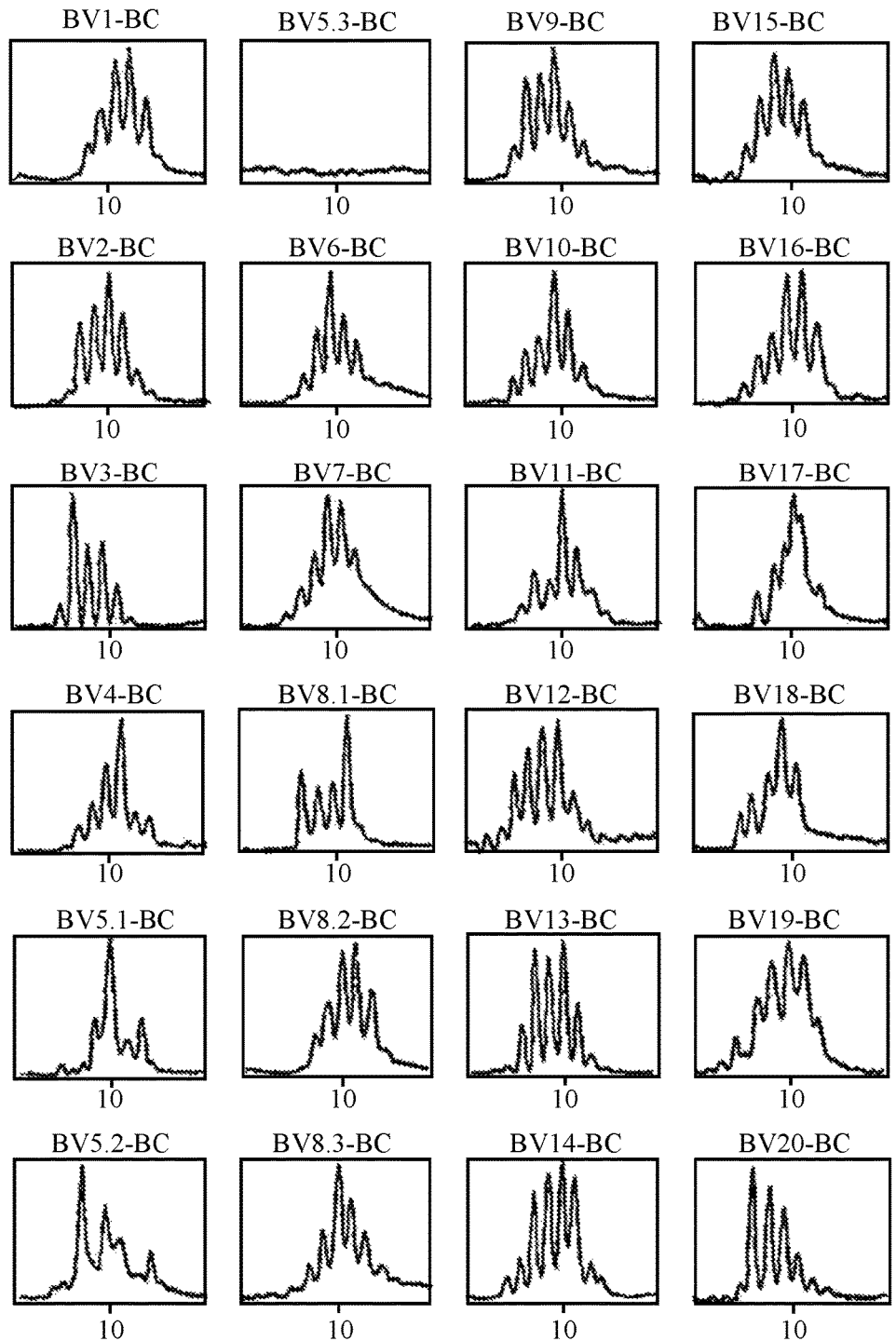
Figure 2C:
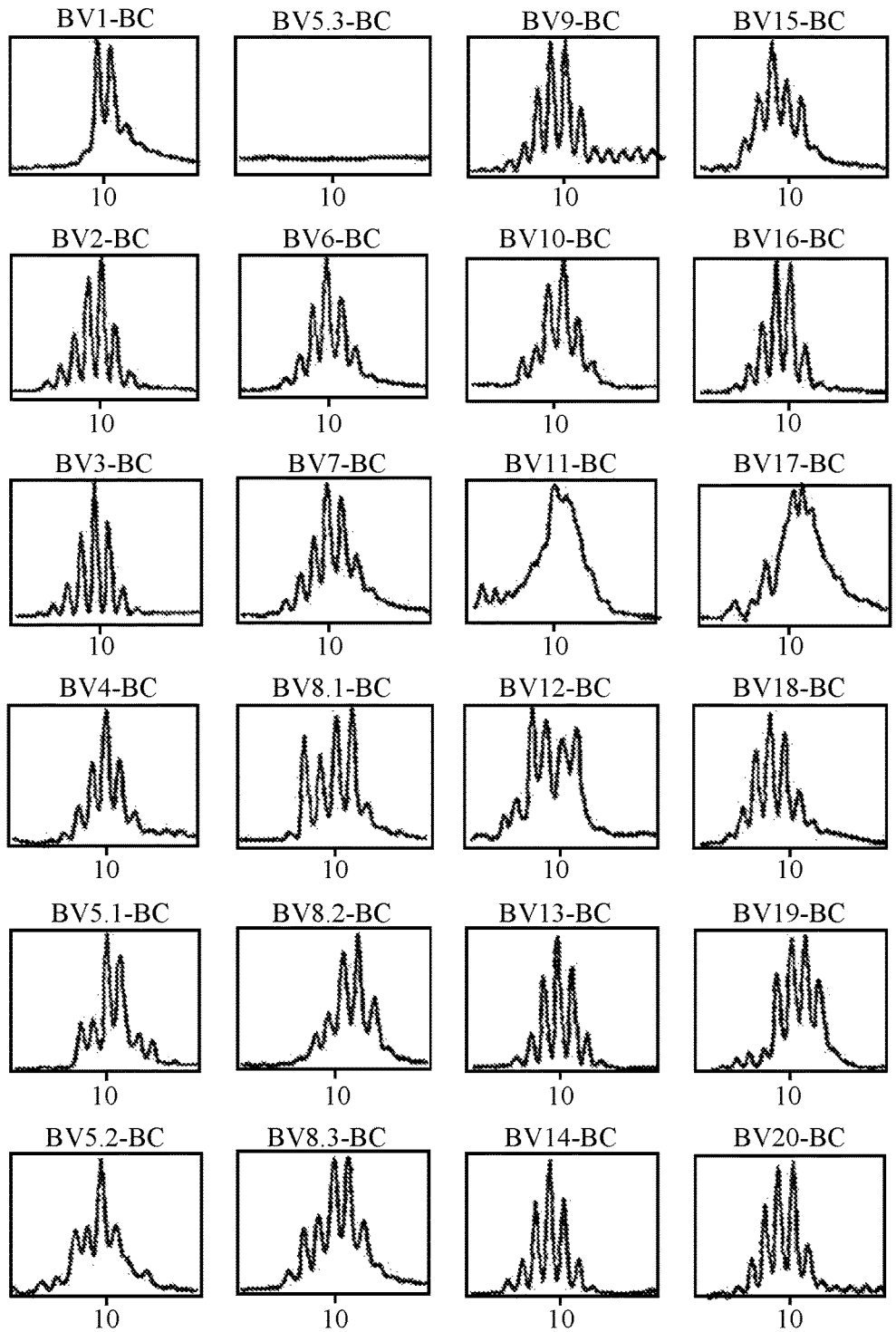

As the presence of a single MHC class I and single MHC class II molecule could diminish the size and diversity of the TCR repertoire, the expression of the various BV families and the CDR3 length diversity was studied as previously described (Cochet, M. et al., *Eur J Immunol* 22, 2639-2647 (1992)) by the RT-PCR-based immunoscope technique, on purified splenic CD4+ or CD8+ T cells. Peaks of significant magnitude with a Gaussian-like distribution were observed for most BV families (15 out of the 20 analyzed) in both CD8+ (FIG. 2b) and CD4+ (FIG. 2c) populations of T cells. Such profiles observed on peripheral T lymphocytes are typical of functionally rearranged BV segments with a 3 nucleotide length variation of the CDR3 subregions from one peak to the next (Cochet, M. et al., *Eur J Immunol* 22, 2639-2647 (1992)).

Absence of expansion (or profoundly altered profile) as observed for BV 5.3 and 17 were expected since these two BV segments are pseudogenes in C57BL/6 mice (Wade, T., Bill, J., Marrack, P. C., Palmer, E. & Kappler, J. W., *J Immunol* 141, 2165-2167 (1988)); Chou, H. S. et al., *Proc Natl Acad Sci USA* 84, 1992-1996 (1987). However, the altered profiles observed for BV 5.1, 5.2 and 11 segments were due to a small subpopulation of corresponding BV-expressing T cells (they represent lower than 5% in C57BL/6 mice, and around 2% in HLA-DR1-transgenic H-2 class II-KO mice) (data not shown). Other than these instances, both CD4+ and CD8+ T cells in HLA-A2.1-/HLA-DR1-transgenic, H-2 class I-/class II-KO mice display, respectively, a pattern of TCR BV chain usage and CDR3 diversity, which is similar to that of non-transgenic C57BL/6 mice.

Example 4: Functional Characterization

Figure 5:
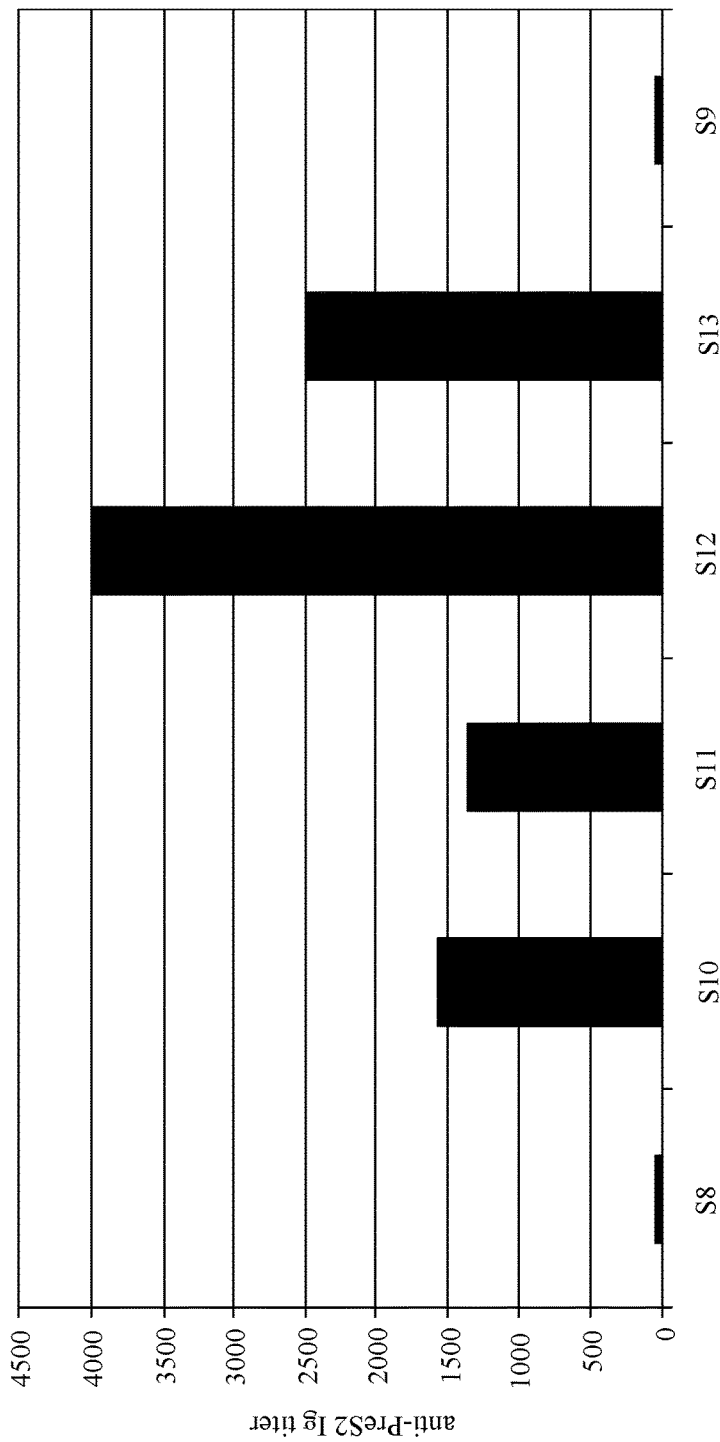
FIG. 5 shows the AC anti-Pre S2 response in HLA-A2+DR1+CI−CII− mice following a pcmv S2/S immunization.
Figure 7:
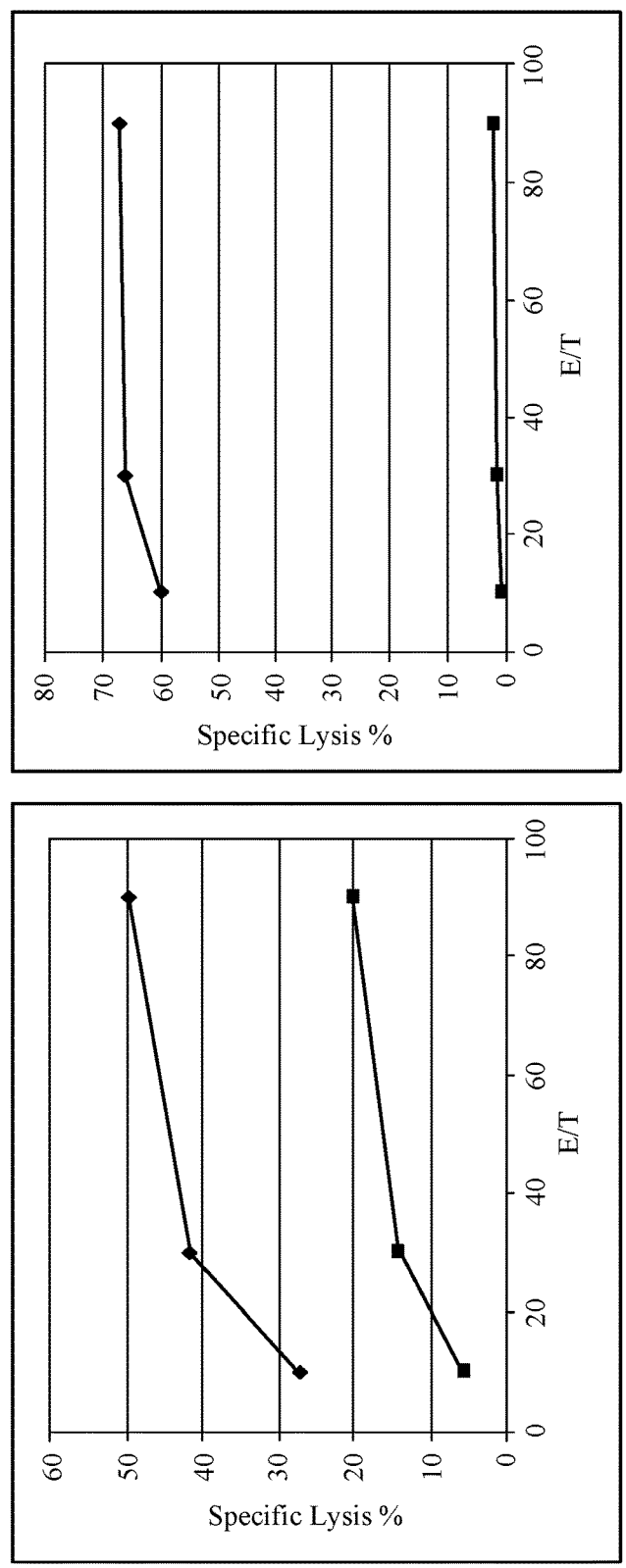
FIG. 7 shows the T CD8 cytotoxic response to the HLA-A2 restricted HBS (348-357) peptide following an immunization of HLA-A2+DR1+CI−CII− mice with pcmv S2/S.

HLA-A2+HLA-DR1+ β2m°IAβ° mice immunized with Ag HBs (hepatitis B envelope protein) were analyzed. FIG. 5 shows the specific humoral response, as indicated by the production of HBs S2 antibodies. FIG. 6 shows the specific DR1-restricted CD4+ T proliferation response of HBs$_{348-357}$. And FIG. 7 shows the specific HLA-A2-restricted CD8+ cytolytic T response of the HBs$_{348-357}$ or HBs$_{335-343}$.

These results show that the HLA-A2+HLA-DR1+ β2m°IAβ° mouse allows for simultaneous analysis of the specific humoral response, of the Ag-specific HLA-DR1-restricted response of CD4+ T helper cells, and of the cytolitic response of Ag-specific HLA-A2-restricted CD8+ T cells in an immunized individual.

Additional data obtained from these mice is provided in the following Tables 1-3.

TABLE 1

Proliferative responses of T CD4+ against HBV virus envelope HLA-DR1 epitopes from HLA-A2+DR1+H-2 CI-CII- transgenic mice injected with pcmv S2-S

| position | Amino Acid sequence | Responder/ tested mice | Stimulation index |
|---|---|---|---|
| 109-134 | MQWNSTTFHQTLQDPRVRGLYFPAGG | (12/12) | 3-4 |
| 200-214 | TSLNFLGGTTVCLGQ | (6/12) | 3-4 |
| 16/31 | QAGFFLLTRILTIPQS | (12/12) | 3-6 |
| 337/357 | SLLVPFVQWFVGLSPTVWLSV | (5/12) | 4-5 |

TABLE 2

Cytolytic response to HLA-A2+DR1+H-2 CI-CII- transgenic mice injected with pcmv S2-S

| position | Amino Acid sequence | Responder/ tested mice | Maximal lysis |
|---|---|---|---|
| 348-357 | GLSPTVWLS | (12/12) | 20-70% |
| 335-343 | WLSLLVPVF | (4/12) | 30% |

TABLE 3

Anti-PreS2 Antibody response anti of HLA-A2+DR1+H-2 CI-CII transgenic mice injected with pcmv S2-S

| position | Amino Acid sequence | Responder/ tested mice |
|---|---|---|
| preS2 | MQWNSTTFHQTLQDPRVRGLYFPAGG | (9/12) |

Example 5: Immune Response to HBsAg-DNA-Vaccine

To evaluate the immunological potential of HLA-A2.1-/HLA-DR1-transgenic, H-2 class I-/class II-KO mice, and to compare their humoral, CD4+ and CD8+ T cell responses to those of humans, mice were immunized with an HBsAg-DNA plasmid. This plasmid encodes two hepatitis B virus envelope proteins (preS2/S middle and S/small) that self-assemble in particles carrying hepatitis B surface antigen. The currently used vaccine against hepatitis B comprises these two proteins.

Figure 3A:
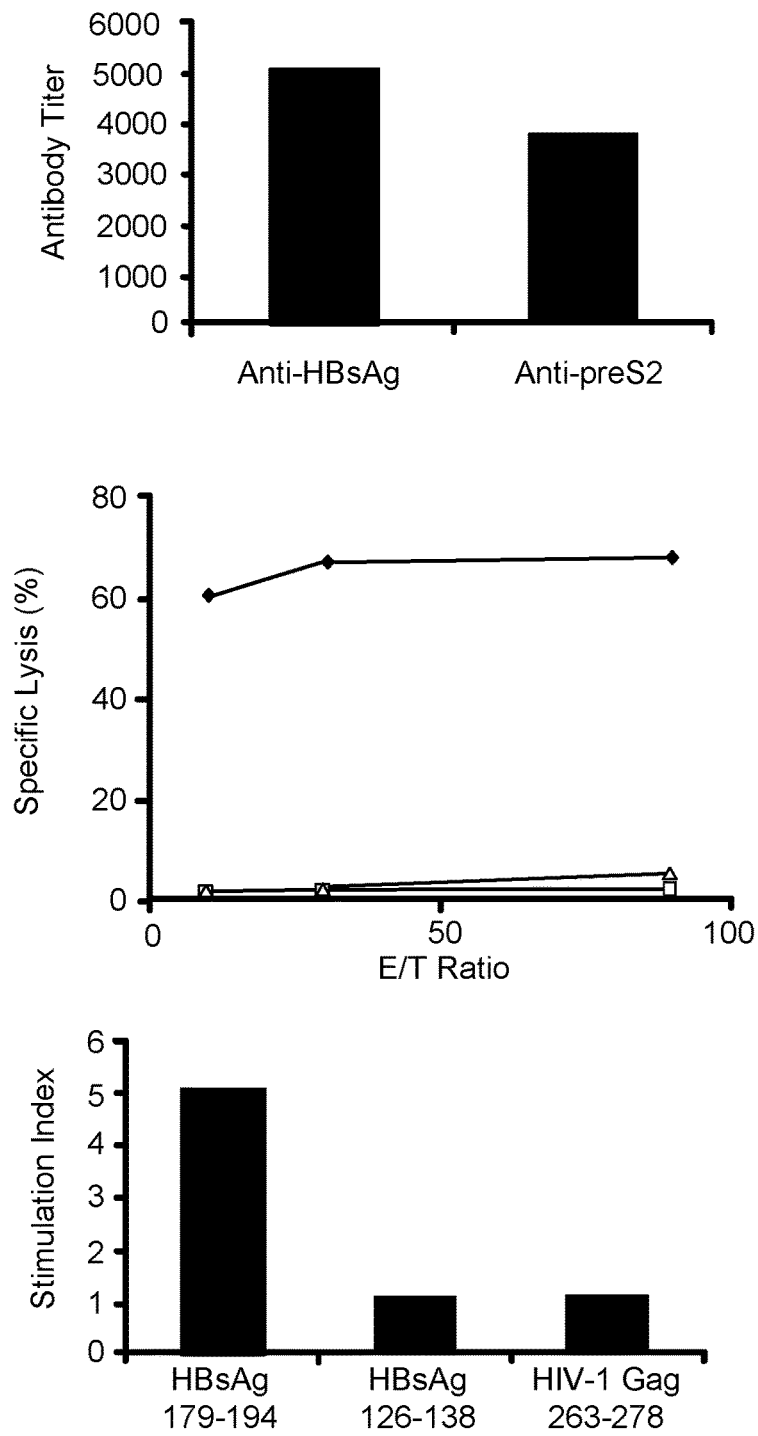
FIGS. 3A and 3B show HBs-specific antibody, cytolytic and proliferative responses. HLA-A2.1-/HLA-DR1-transgenic H-2 class I-/class II-KO mice were or not immunized by intramuscular injection of HBsAg-encoding plasmid-DNA and then individually tested.

As illustrated in FIG. 3a for a representative mouse, HBsAg-specific antibodies were first detected at day 12 after injection of the HBsAg-DNA-vaccine (FIG. 3a, upper panel), and the titer of these antibodies increased up to day 24 (12 days after the second DNA immunization, data non shown). This early antibody response was specific for the preS2-B cell epitope (HBs$_{109-134}$) carried by the middle HBV envelope protein and for HBsAg particles, in agreement with a similar response reported in HBsAg-DNA-immunized mice (Michel, M. L. et al., Proc Natl Acad Sci USA 92, 5307-5311 (1995)) and in HBsAg vaccinated humans (Moulia-Pelat, J. P. et al., Vaccine 12, 499-502 (1994)).

The CD8$^+$ CTL response to HBsAg was examined to determine whether the CD8$^+$ T cells in the periphery of the HLA-A2.1-/HLA-DR1-transgenic, H-2 class I-/class II-KO mouse were functionally restricted by the transgenic human class I molecules. In HBV-infected HLA-A2.1$^+$ humans, the immunodominant HLA-A2.1-restricted HBsAg-specific CTL response is directed at the HBsAg$_{348-357}$ (Maini, M. K. et al., Gastroenterology 117, 1386-1396 (1999)) and at the HBsAg$_{335-343}$ (Nayersina, R. et al., J Immunol 150, 4659-4671 (1993)) peptide (i.e., a multi-epitopic response is observed). In C57BL/6 mice, the H-2 K$^b$-restricted HBsAg-specific CTL response is directed at the HBsAg$_{371-378}$ peptide (Schirmbeck, R., Wild, J. & Reimann, J., Eur J Immunol 28, 4149-4161 (1998)). To evaluate whether the humanized mouse may respond as humans, splenic T cells were restimulated for 7 days, as described herein, with either relevant (HBsAg$_{348-357}$, HLA-A2.1-restricted), or control (HBsAg$_{371-378}$, H-2 K$^b$-restricted; MAGE-3$_{271-279}$, HLA-A2.1-restricted) peptide. FIG. 3a (middle panel) shows that HBsAg-DNA-immunization elicited a strong HBsAg$_{348-357}$-specific CTL response, but no response to either HBsAg$_{371-378}$ or the MAGE-3$_{271-279}$ peptide.

To determine whether the CD4$^+$ T cells in the periphery of this HLA-A2.1-/HLA-DR1-transgenic, H-2 class I-/class II-KO mouse may be functionally restricted by the transgenic human class II molecules, the CD4$^+$ T cell response to the HBsAg protein was examined. In HBsAg-vaccinated or HBV-infected HLA-DR1$^+$ humans, an immunodominant HLA-DR1-restricted HBsAg-specific CD4$^+$ T cell response is directed at the HBsAg$_{180-195}$ peptide (Mm, W. P. et al., Hum Immunol 46, 93-99 (1996)). In C57BL/6 mice, the H-2 IA$^b$-restricted HBsAg-specific CD4$^+$ T cell response is directed at the HBsAg$_{126-138}$ peptide (Milich, D. R., Semin Liver Dis 11, 93-112 (1991)). To compare the humanized mouse with humans and wild-type mice, splenic T cells were restimulated in vitro with either relevant (HBsAg$_{180-195}$, HLA-DR1-restricted) or control (HBsAg$_{126-138}$, H-2 IA$^b$-restricted; HIV 1 Gag$_{263-278}$, HLA-DR1-restricted) peptides. FIG. 3a (lower panel) shows a strong proliferative response directed against the HLA-DR1-restricted HBsAg$_{180-195}$ peptide, while the H-2 IA$^\square$-restricted peptide was not efficient at stimulating a response, as expected. Similarly, no response was induced by the HIV 1 Gag$_{263-278}$ peptide. Moreover, an additional in vitro recall with the HBsAg$_{180-195}$ peptide increased several-fold the specific proliferative index (data not shown).

Figure 3B:
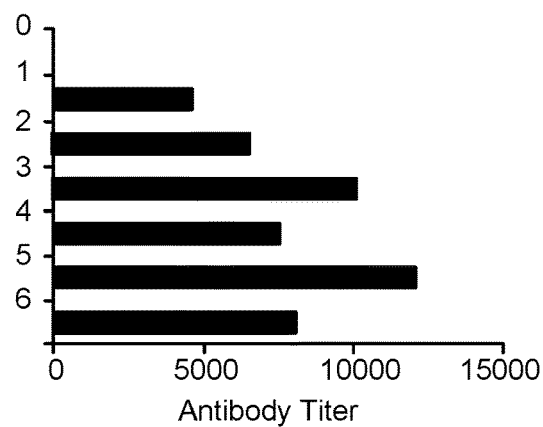
Figure 3B:
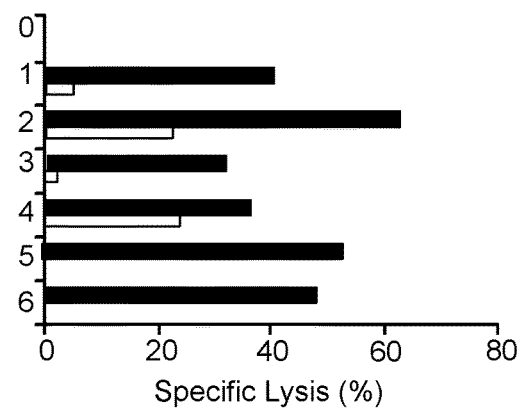
Figure 3B:
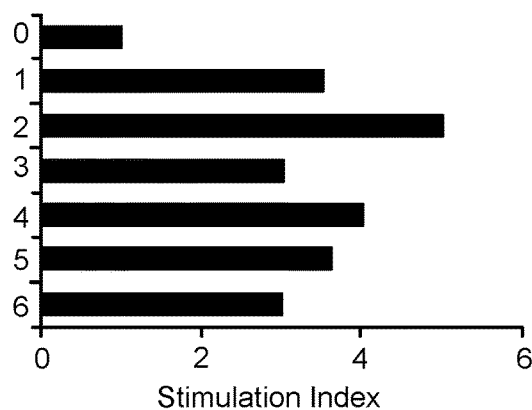

Having documented in a first HBsAg-DNA-immunized HLA-A2.1-/HLA-DR1-transgenic H-2 class I-/class II-KO mouse the development and the specificity of the HBsAg-specific antibody, proliferative and cytolytic T cell responses, 6 additional HBsAg-DNA-immunized and 6 naive control HLA-A2.1-/HLA-DR1-transgenic H-2 class I-/class II-KO mice were also tested individually for the same three responses. As illustrated in FIG. 3b, the three responses were simultaneously documented in the 6 immunized animals tested and not in control naive mice. Interestingly, 2 immunized mice were able to develop CTL responses against both HBsAg$_{348-357}$ and HBsAg$_{335-343}$ HLA-A2.1 restricted peptides (FIG. 3b, middle panel).

Example 6: Protection Assays

The above examples document the induction of HBsAg-specific humoral, CD4$^+$ and CD8$^+$ T cell responses in HLA-A2.1-/HLA-DR1-transgenic, H-2 class I-/class II-KO mice, and show that they are directed at the same immunodominant epitopes as those of naturally-infected or HBsAg-vaccinated humans. This example tested whether these responses conferred protection to vaccinated animals. Since mice are not permissive to HBV, a HBsAg-recombinant vaccinia virus (rVV-HBsAg) was used for these experiments. Mice were immunized twice intramuscularly with 100 μg of HBsAg-DNA. Twelve days after the last immunization, mice were challenged intraperitoneally with 10$^7$ PFU of rVV-HBsAg. Four days later, virus titers were determined according to published methods and recorded as rVV PFU/ovary (Buller, R. M. & Wallace, G. D., Lab Anim Sci 35, 473-476 (1985)).

Figure 4:
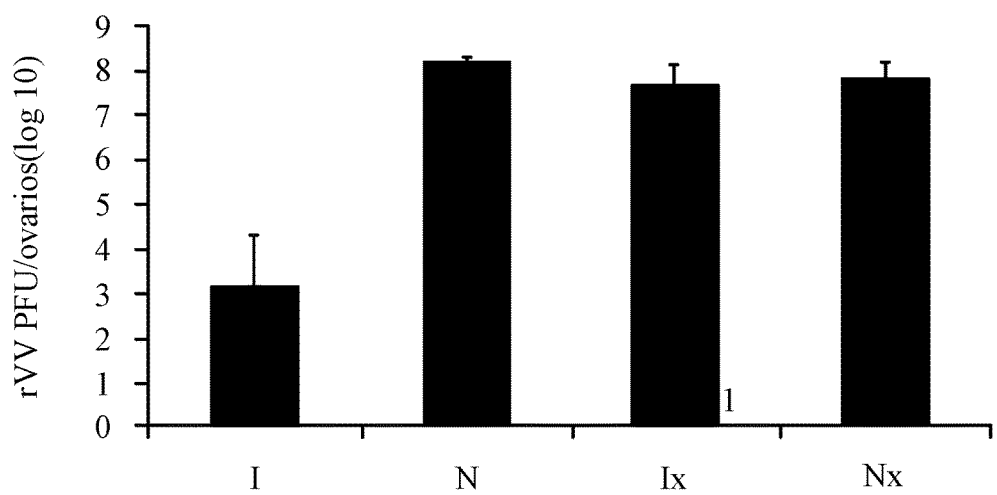
FIG. 4 shows results of protection assays. HLA-A2.1-/HLA-DR1-transgenic H-2 class I-/class II-/KO mice were or not immunized twice with plasmid DNA encoding HBsAg. Fifteen days after the last immunization, they were challenged intraperitoneally with $10^7$ PFU of rVV expressing either the HBsAg or the HBx protein. Four days later, animals were tested individually for viral titers in ovaries. The results (rVV PFU/ovary in log 10) are given for the HBsAg-DNA-immunized mice challenged with rVV-HBsAg (I, n=10), naive mice challenged with rVV-HBsAg (N, n=6), HBsAg-immune mice challenged with rVV-HBx (Ix, n=6) and naive mice challenged with rVV-HBx (Nx, n=6).

The results are illustrated in FIG. 4. Naive animals that had not been immunized with HBsAg-DNA showed evidence of rVV-HBsAg replication after challenge. In contrast, the virus titers in mice immunized with HBsAg-DNA were more than 4 orders of magnitude lower. These results strongly suggest that vaccination with HBsAg-DNA induced protective HBsAg-specific immune responses that controlled the infection with rVV-HBsAg.

The specificity of the protection conferred by HBsAg-DNA-vaccination was documented by challenging HBsAg-DNA-immunized mice with another HBx-recombinant VV (encoding hepatitis B×protein). No reduction of rVV-HBx replication was observed in HBsAg-DNA-immunized mice compared to unimmunized controls.

Example 7: HLA-DR1-Restricted CD4$^+$ T Cells are Critical for Antibody and CTL Responses and Protection Against Viral Infection To evaluate whether HLA-DR1-restricted T helper lymphocytes contribute to antibody and CTL responses in the humanized mice, the immune response and the efficiency of viral infection were compared in single (HLA-A2.1) and double (HLA-A2.1/HLA-DR1) transgenic, H-2 class I-/class II-KO mice. As shown in Table 4, a potent HBsAg$_{348-357}$-specific CTL response was observed in HLA-A2.1-/HLA-DR1-double transgenic, H-2 class I-/class II-KO mice, but not in HLA-A2.1-single transgenic H-2 class I-/class II-KO mice. Furthermore, anti-HBs antibodies could not be detected in HBsAg-DNA-vaccinated HLA-A2.1-single transgenic H-2 class I-/class II-KO mice. As a consequence, HBsAg-DNA-immunized HLA-A2.1-single transgenic H-2 class I-/class II-KO mice were not protected against rVV-HBsAg infection.

TABLE 4

Antibody, cytolytic, and proliferative responses of HBsAg-DNA-immunized mice, and protection against rVV-HBsAg-challenge

| | | Specific Lysis (%) | | Proliferation (SI) | Antibody Titer | rVV-HBsAg PFU/ovary (log10) |
|---|---|---|---|---|---|---|
| | Mice | 348-357 | 335-343 | 179-194 | | |
| A | 1 | 0 | 0 | 1 | 0 | 2.5 · 10$^8$ |
| | 2 | 0 | 0 | 1 | 0 | 2.5 · 10$^8$ |

TABLE 4-continued

Antibody, cytolytic, and proliferative responses of HBsAg-DNA-immunized mice, and protection against rVV-HBsAg-challenge

| | Mice | Specific Lysis (%) 348-357 | Specific Lysis (%) 335-343 | Proliferation (SI) 179-194 | Antibody Titer | rVV-HBsAg PFU/ovary (log10) |
|---|---|---|---|---|---|---|
|   | 3  | 0  | 0  | 1   | 0     | $10^8$        |
|   | 4  | 0  | 0  | 1   | 0     | $2.5 \cdot 10^8$ |
|   | 5  | 0  | 0  | 1   | 0     | $10^8$        |
|   | 6  | 0  | 0  | 1   | 0     | $1.5 \cdot 10^8$ |
| B | 1  | 30 | 15 | 4.7 | 2000  | $10^4$        |
|   | 2  | 14 | 0  | 3.9 | 3000  | $3 \cdot 10^3$ |
|   | 3  | 30 | 11 | 4   | 7500  | $4 \cdot 10^3$ |
|   | 4  | 5  | 0  | 2.5 | 6500  | $7.5 \cdot 10^3$ |
|   | 5  | 50 | 30 | 6.3 | 13000 | $7.5 \cdot 10^2$ |
|   | 6  | 40 | 18 | 4   | 16000 | $5 \cdot 10^2$ |
|   | 7  | 6  | 7  | 2.9 | 1500  | $2 \cdot 10^4$ |
|   | 8  | 5  | 5  | 3   | 2500  | $1.5 \cdot 10^4$ |
|   | 9  | 24 | 36 | 4.5 | 3000  | $<10^2$       |
|   | 10 | 23 | 14 | 5   | 15000 | $5 \cdot 10^3$ |
| C | 1  | 0  | 0  | 1   | 0     | $10^8$        |
|   | 2  | 0  | 0  | 1   | 0     | $2 \cdot 10^8$ |
|   | 3  | 0  | 0  | 1   | 0     | $1.5 \cdot 10^8$ |
|   | 4  | 0  | 0  | 1   | 0     | $10^8$        |
|   | 5  | 0  | 0  | 1   | 0     | $2.5 \cdot 10^8$ |
|   | 6  | 0  | 0  | 1   | 0     | $10^8$        |

Naive HLA-A2.1-/HLA-DR1-double transgenic H-2 class I-/class II-KO mice (A 1-6), HBsAg-DNA-immunized HLA-A2.1-/HLA-DR1-double transgenic H-2 class I-/class II-KO mice (B 1-10) and HBsAg-DNA-immunized HLA-A2.1-single transgenic H-2 class I-/class II-KO mice (C 1-6) were challenged intraperitoneally with $10^7$ PFU of rVV-HBsAg. Four days later, PFU per ovary, cytolytic and proliferative splenic T cell responses and serum antibody titers were assessed individually using either $HBsAg_{348-357}$, (immunodominant) or $HBsAg_{335-343}$ (subdominant), HLA-A2.1-restricted peptides-loaded RMAS-HHD target cells (E/T ratio 30/1) for cytolytic assays, $HBsAg_{179-194}$ HLA-DR1-restricted peptide for proliferation assays and $preS2_{109-134}$ peptide for the determination of antibody (IgG) titers.

The entire contents of all references, patents and published patent applications cited throughout this application are herein incorporated by reference in their entirety.

What is claimed is:

1. A method of simultaneously identifying the presence of one or more epitopes in a candidate antigen or group of antigens, wherein the epitope elicits a specific humoral response, a TH HLA-DR1 restricted response, and/or a CTRL HLA-A2 restricted response, the method comprising:
   a) administering the candidate antigen or group of candidate antigens to a transgenic mouse comprising:
      1) a disrupted H2 class I gene;
      2) a disrupted H2 class II gene;
      3) a functional HLA-A2 transgene; and
      4) a functional HLA-DR1 transgene,
      wherein the transgenic mouse has the genotype HLA-A2⁺HLA-DR1¹ß2m°IAß° and the phenotypes of (i) complete restriction by the HLA transgenes, and (ii) complete absence of immune responses restricted by the H2 genes;
   b) assaying for a specific humoral response in the mouse to the antigen;
   c) assaying for a TH HLA-DR1 restricted response in the mouse to the antigen; and
   d) assaying for a CTRL HLA-A2 restricted response in the mouse to the antigen;
   wherein,
   observation of a specific humoral response in the mouse to the antigen identifies an epitope in the antigen that elicits a humoral response; observation of a TH HLA-DR1 restricted response in the mouse to the antigen identifies an epitope in the antigen that elicits a TH HLA DR1 restricted response; and observation of a CTRL HLA-A2 restricted response in the mouse to the antigen identifies an epitope in the antigen that elicits a CTRL HLA-A2 restricted response.

2. The method of claim 1, further comprising assaying for a Th1-specific response in the mouse to the antigen and assaying for a Th2-specific response in the mouse to the antigen; wherein
   observation of a Th1-specific response in the mouse to the antigen identifies an epitope that elicits a Th1-specific response in the mouse to the antigen; and
   observation of a Th2-specific response in the mouse to the antigen identifies an epitope that elicits a Th2-specific response in the mouse to the antigen.

3. A method of identifying the presence of an HLA DR1-restricted T helper epitope In a candidate antigen or group of candidate antigens, the method comprising:

a) administering the candidate antigen or group of candidate antigens to a transgenic mouse comprising:
   1) a disrupted H2 class I gene;
   2) a disrupted H2 class II gene;
   3) a functional HLA-A2 transgene; and
   4) a functional HLA-DR1 transgene,
   wherein the transgenic mouse has the genotype HLA-A2$^+$HLA-DR1$^1$ß2m°IAß° and the phenotypes of (i) complete restriction by the HLA transgenes, and (ii) complete absence of immune responses restricted by the H2 genes; and
b) assaying for a TH HLA-DR1 restricted T helper epitope response in the mouse to the antigen; wherein, observation of a TH HLA-DR1 restricted T helper epitope response in the mouse to the antigen identifies an epitope in the antigen that elicits a TH HLA-DR1 restricted T helper epitope response.

4. A method of Identifying the presence of an HLA-A2-restricted T cytotoxic (CTL) epitope in a candidate antigen or group of candidate antigens, the method comprising:

a) administering the candidate antigen or group of candidate antigens to a transgenic mouse comprising:
   1) a disrupted H2 class I gene;
   2) a disrupted H2 class II gene;
   3) a functional HLA-A2 transgene; and
   4) a functional HLA-DR1 transgene,
   wherein the transgenic mouse has the genotype HLA-A2$^+$HLA-DR1$^1$ß2m°IAß° and the phenotypes of (i) complete restriction by the HLA transgenes, and (ii) complete absence of immune responses restricted by the H2 genes; and
b) assaying for an HLA-A2-restricted T cytotoxic (CTL) response in the mouse to the antigen or group of antigens; wherein,
observation of an HLA-A2-restricted T cytotoxic (CTL) response in the mouse to the antigen or group of antigens identifies an epitope in the antigen group of antigens that elicits an HLA-A2-restricted T cytotoxic (CTL) response.

* * * * *